United States Patent
Raj et al.

(10) Patent No.: US 10,308,983 B2
(45) Date of Patent: Jun. 4, 2019

(54) METHOD FOR DETECTING CHROMOSOME STRUCTURE AND GENE EXPRESSION SIMULTANEOUSLY IN SINGLE CELLS

(75) Inventors: Arjun Raj, Wynnewood, PA (US); Marshall J. Levesque, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 285 days.

(21) Appl. No.: 13/982,974

(22) PCT Filed: Feb. 6, 2012

(86) PCT No.: PCT/US2012/023974
§ 371 (c)(1), (2), (4) Date: Oct. 7, 2013

(87) PCT Pub. No.: WO2012/106711
PCT Pub. Date: Aug. 9, 2012

(65) Prior Publication Data
US 2014/0024032 A1    Jan. 23, 2014

Related U.S. Application Data

(60) Provisional application No. 61/439,623, filed on Feb. 4, 2011.

(51) Int. Cl.
*C12Q 1/68* (2018.01)
*C07H 21/00* (2006.01)
*C12Q 1/6841* (2018.01)

(52) U.S. Cl.
CPC ..... *C12Q 1/6841* (2013.01); *C12Q 2600/158* (2013.01)

(58) Field of Classification Search
CPC ............................ C12Q 1/68; C07H 21/00
See application file for complete search history.

(56) References Cited

U.S. PATENT DOCUMENTS

| | | | | |
|---|---|---|---|---|
| 5,925,517 A * | 7/1999 | Tyagi | ............... | C12Q 1/6816 435/6.1 |
| 6,528,802 B1 | 3/2003 | Koenig et al. | | |
| 2007/0026381 A1* | 2/2007 | Huang | ............... | B01L 3/502746 435/4 |
| 2011/0082049 A1* | 4/2011 | Endress et al. | ............... | 506/9 |

FOREIGN PATENT DOCUMENTS

| WO | 0068692 A1 | 11/2000 |
|---|---|---|
| WO | WO 2008084405 | 7/2008 |
| WO | 2009102446 A2 | 8/2009 |
| WO | WO2011011527 A2 | 1/2011 |

OTHER PUBLICATIONS

Dirks et al.Visualizing RNA molecules inside the nucleus of living cells. Methods 29: 51 (2003).*
Rapp et al., Bicolor fluorescence in situ hybridization to intron and exon mRNA sequences. Experimental Cell Research 197(2) : 319 (1991). Abstract Only.*
Herman et al., In Situ Hybridization Analysis of Arginine Vasopressin Gene Transcription Using Intron-Specific Probes. Molecular Endocrinology 5 (10) : 1447 (1991).*
Levsky et al., The Spatial Order of Transcription in Mammalian Cells. Journal of Cellular Biochemistry 102 : 609 (2007).*
Grand et al., Genes, Chromosomes & Cancer 23: 109 (1998). (Year: 1998).*
Search Report—Chinese Application No. 201280016912.7 dated Apr. 3, 2015.
Tanke et al., "FISH and Immunocytochemistry: towards visualizing single target molecules in living cells." 2004, Current Opinion in Biotechnology 16:49-54.
Raj et al., "Imaging individual mRNA molecules using multiple singly labeled probes." 2008, Nat Methods 5(10): 877-879.
Levsky et al., "Single-Cell Gene Expression Profiling." 2002, Science 297: 836-840.
Dekker et al., "Capturing Chomosome Conformation." 2002, Science 295: 1306-1311.
Femino et al., "Visualization of Single RNA Transcripts in Situ." 1998, Science 280: 585-590.
Alberts, et al., "Molecular Biology of the Cell", 4th edition, Newtown Press, Dec. 20, 2004, 327-331.
Office Action for Japanese Patent Application No. 2013-552715 dated Jan. 25, 2016.
Japanese Patent Application No. 2013-552715—Notice for Reasons of Rejection dated Sep. 9, 2016.
Levesque, et al., Single-chromosome transcriptional profiling reveals chromosomal gene expression regulation, Nat Methods. 10(3) ,Mar. 2013 ,246-248.

* cited by examiner

*Primary Examiner* — Ethan C Whisenant
(74) *Attorney, Agent, or Firm* — Saul Ewing Arnstein & Lehr LLP; Kathryn Doyle

(57) ABSTRACT

The present invention relates to systems and methods for measuring chromosome structure and gene expression. In one embodiment, the present invention includes an assay for determining the spatial organization of gene expression in the nucleus. The present invention also includes a method based on fluorescence in situ hybridization (FISH) that simultaneously yields information on the physical position and expression of individual genes. By lighting up a large number of targets on a particular chromosome using a bar-coding scheme, the large scale structure of an entire chromosome can be determined.

23 Claims, 10 Drawing Sheets
(7 of 10 Drawing Sheet(s) Filed in Color)
Specification includes a Sequence Listing.

SEQUENCE LISTING

<160> NUMBER OF SEQ ID NOS: 451

<210> SEQ ID NO 1
<211> LENGTH: 20
<212> TYPE: DNA
<213> ORGANISM: Artificial Sequence
<220> FEATURE:
<223> OTHER INFORMATION: Chemically synthesized

<400> SEQUENCE: 1
ctagtaccgc gttggttcta                                                     20

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
cagagtgcaa aatcccttc                                                      20

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized

<400> SEQUENCE: 3
taccgtacca gcatgtaact                                                     20

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized

<400> SEQUENCE: 4
cacaccaaga atcagtcctc                                                     20

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
gcccattcca gaaagcttta                                                     20

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized

<400> SEQUENCE: 6
cctcccatat cctcccttaa                                                     20

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized

<400> SEQUENCE: 7
tctaaattca agaaccgccc                                           20

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized

<400> SEQUENCE: 8
atctcctttc agatccggtc                                           20

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized

<400> SEQUENCE: 9
ggctccagaa acagatttca                                           20

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized

<400> SEQUENCE: 10
taaatcccag actcaggact                                           20

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized

<400> SEQUENCE: 11
aagggccaag tcaagttaag                                           20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized

<400> SEQUENCE: 12
ataactgcat tgcccattga                                           20

<210> SEQ ID NO 13
<211> LENGTH: 20
<212> TYPE: DNA
<213> ORGANISM: Artificial Sequence
<220> FEATURE:
<223> OTHER INFORMATION: Chemically synthesized

<400> SEQUENCE: 13
tgactcttat gagggagctc                                           20

```
<210> SEQ ID NO 14
<211> LENGTH: 20
<212> TYPE: DNA
<213> ORGANISM: Artificial Sequence
<220> FEATURE:
<223> OTHER INFORMATION: Chemically synthesized

<400> SEQUENCE: 14
agtgaatttg gcccaagaag                                                   20

<210> SEQ ID NO 15
<211> LENGTH: 20
<212> TYPE: DNA
<213> ORGANISM: Artificial Sequence
<220> FEATURE:
<223> OTHER INFORMATION: Chemically synthesized

<400> SEQUENCE: 15
cagagatagt ctgggaggag                                                   20

<210> SEQ ID NO 16
<211> LENGTH: 20
<212> TYPE: DNA
<213> ORGANISM: Artificial Sequence
<220> FEATURE:
<223> OTHER INFORMATION: Chemically synthesized

<400> SEQUENCE: 16
gctaagtgtt gcctctactg                                                   20

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized

<400> SEQUENCE: 17
gaatccacgg tccattttgg                                                   20

<210> SEQ ID NO 18
<211> LENGTH: 20
<212> TYPE: DNA
<213> ORGANISM: Artificial Sequence
<220> FEATURE:
<223> OTHER INFORMATION: Chemically synthesized

<400> SEQUENCE: 18
cttgctgtat ttggggatca                                                   20

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
catcgagatg cacagctttg                                                   20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized
```

<400> SEQUENCE: 20
gtgacatccg tctctggagg                                       20

<210> SEQ ID NO 21
<211> LENGTH: 20
<212> TYPE: DNA
<213> ORGANISM: Artificial Sequence
<220> FEATURE:
<223> OTHER INFORMATION: Chemically synthesized

<400> SEQUENCE: 21
aaggagcaag aaccacacag                                       20

<210> SEQ ID NO 22
<211> LENGTH: 20
<212> TYPE: DNA
<213> ORGANISM: Artificial Sequence
<220> FEATURE:
<223> OTHER INFORMATION: Chemically synthesized

<400> SEQUENCE: 22
aatgcacggt taaagttcct                                       20

<210> SEQ ID NO 23
<211> LENGTH: 20
<212> TYPE: DNA
<213> ORGANISM: Artificial Sequence
<220> FEATURE:
<223> OTHER INFORMATION: Chemically synthesized

<400> SEQUENCE: 23
caggcacaga tttacaggaa                                       20

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
agccagttct cattagcaag                                       20

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized

<400> SEQUENCE: 25
acacactaaa gaacacaccc                                       20

<210> SEQ ID NO 26
<211> LENGTH: 20
<212> TYPE: DNA
<213> ORGANISM: Artificial Sequence
<220> FEATURE:
<223> OTHER INFORMATION: Chemically synthesized

<400> SEQUENCE: 26
gatccttgtg cacggaagtt                                       20

<210> SEQ ID NO 27

<210> SEQ ID NO 27
<211> LENGTH: 20
<212> TYPE: DNA
<213> ORGANISM: Artificial Sequence
<220> FEATURE:
<223> OTHER INFORMATION: Chemically synthesized

<400> SEQUENCE: 27
aatgaactga tggcgttcat                                               20

<210> SEQ ID NO 28
<211> LENGTH: 20
<212> TYPE: DNA
<213> ORGANISM: Artificial Sequence
<220> FEATURE:
<223> OTHER INFORMATION: Chemically synthesized

<400> SEQUENCE: 28
cacacctcac ttgaacaagt                                               20

<210> SEQ ID NO 29
<211> LENGTH: 20
<212> TYPE: DNA
<213> ORGANISM: Artificial Sequence
<220> FEATURE:
<223> OTHER INFORMATION: Chemically synthesized

<400> SEQUENCE: 29
gtgagggttc ctctgactca                                               20

<210> SEQ ID NO 30
<211> LENGTH: 20
<212> TYPE: DNA
<213> ORGANISM: Artificial Sequence
<220> FEATURE:
<223> OTHER INFORMATION: Chemically synthesized

<400> SEQUENCE: 30
tttcacaaat ccagctggaa                                               20

<210> SEQ ID NO 31
<211> LENGTH: 20
<212> TYPE: DNA
<213> ORGANISM: Artificial Sequence
<220> FEATURE:
<223> OTHER INFORMATION: Chemically synthesized

<400> SEQUENCE: 31
cccaaagacc caaatcagaa                                               20

<210> SEQ ID NO 32
<211> LENGTH: 20
<212> TYPE: DNA
<213> ORGANISM: Artificial Sequence
<220> FEATURE:
<223> OTHER INFORMATION: Chemically synthesized

<400> SEQUENCE: 32
ggggttgaac caaatatcca                                               20

<210> SEQ ID NO 33
<211> LENGTH: 20
<212> TYPE: DNA
<213> ORGANISM: Artificial Sequence
<220> FEATURE:
<223> OTHER INFORMATION: Chemically synthesized

<400> SEQUENCE: 33
attactacgc ctgccacatc         20

<210> SEQ ID NO 34
<211> LENGTH: 20
<212> TYPE: DNA
<213> ORGANISM: Artificial Sequence
<220> FEATURE:
<223> OTHER INFORMATION: Chemically synthesized

<400> SEQUENCE: 34
cggcagaaaa tcgatctcaa         20

<210> SEQ ID NO 35
<211> LENGTH: 20
<212> TYPE: DNA
<213> ORGANISM: Artificial Sequence
<220> FEATURE:
<223> OTHER INFORMATION: Chemically synthesized

<400> SEQUENCE: 35
ctttgctcgt tctgccattc         20

<210> SEQ ID NO 36
<211> LENGTH: 20
<212> TYPE: DNA
<213> ORGANISM: Artificial Sequence
<220> FEATURE:
<223> OTHER INFORMATION: Chemically synthesized

<400> SEQUENCE: 36
ctttgtacat ctgggagtca         20

<210> SEQ ID NO 37
<211> LENGTH: 20
<212> TYPE: DNA
<213> ORGANISM: Artificial Sequence
<220> FEATURE:
<223> OTHER INFORMATION: Chemically synthesized

<400> SEQUENCE: 37
acacctcgtg tctcaataag         20

<210> SEQ ID NO 38
<211> LENGTH: 20
<212> TYPE: DNA
<213> ORGANISM: Artificial Sequence
<220> FEATURE:
<223> OTHER INFORMATION: Chemically synthesized

<400> SEQUENCE: 38
cgagcaagaa gcttcatcat         20

<210> SEQ ID NO 39
<211> LENGTH: 20
<212> TYPE: DNA
<213> ORGANISM: Artificial Sequence
<220> FEATURE:
<223> OTHER INFORMATION: Chemically synthesized

<400> SEQUENCE: 39
acgtaaggga tgaatcctct         20

<210> SEQ ID NO 40
<211> LENGTH: 20
<212> TYPE: DNA

```
<213> ORGANISM: Artificial Sequence
<220> FEATURE:
<223> OTHER INFORMATION: Chemically synthesized

<400> SEQUENCE: 40
actaaagtct catttggggc                                                 20

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized

<400> SEQUENCE: 41
tgagtgtcaa cagatttcct                                                 20

<210> SEQ ID NO 42
<211> LENGTH: 20
<212> TYPE: DNA
<213> ORGANISM: Artificial Sequence
<220> FEATURE:
<223> OTHER INFORMATION: Chemically synthesized

<400> SEQUENCE: 42
ggaaccaccg ttaataggtg                                                 20

<210> SEQ ID NO 43
<211> LENGTH: 20
<212> TYPE: DNA
<213> ORGANISM: Artificial Sequence
<220> FEATURE:
<223> OTHER INFORMATION: Chemically synthesized

<400> SEQUENCE: 43
gaatcttgcc agcctaacac                                                 20

<210> SEQ ID NO 44
<211> LENGTH: 20
<212> TYPE: DNA
<213> ORGANISM: Artificial Sequence
<220> FEATURE:
<223> OTHER INFORMATION: Chemically synthesized

<400> SEQUENCE: 44
gttcagtcca aacgaaccag                                                 20

<210> SEQ ID NO 45
<211> LENGTH: 20
<212> TYPE: DNA
<213> ORGANISM: Artificial Sequence
<220> FEATURE:
<223> OTHER INFORMATION: Chemically synthesized

<400> SEQUENCE: 45
ctcgtgattt ccaggaacac                                                 20

<210> SEQ ID NO 46
<211> LENGTH: 20
<212> TYPE: DNA
<213> ORGANISM: Artificial Sequence
<220> FEATURE:
<223> OTHER INFORMATION: Chemically synthesized

<400> SEQUENCE: 46
gaaagagacg ttgccaagtc                                                 20
```

<210> SEQ ID NO 47
<211> LENGTH: 20
<212> TYPE: DNA
<213> ORGANISM: Artificial Sequence
<220> FEATURE:
<223> OTHER INFORMATION: Chemically synthesized

<400> SEQUENCE: 47
ggactgaacc tcactcattc                                                 20

<210> SEQ ID NO 48
<211> LENGTH: 20
<212> TYPE: DNA
<213> ORGANISM: Artificial Sequence
<220> FEATURE:
<223> OTHER INFORMATION: Chemically synthesized

<400> SEQUENCE: 48
agatattgta ggagtggggg                                                 20

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized

<400> SEQUENCE: 49
aactgcctaa accttctgtg                                                 20

<210> SEQ ID NO 50
<211> LENGTH: 20
<212> TYPE: DNA
<213> ORGANISM: Artificial Sequence
<220> FEATURE:
<223> OTHER INFORMATION: Chemically synthesized

<400> SEQUENCE: 50
gtccccacaa gtaagcatac                                                 20

<210> SEQ ID NO 51
<211> LENGTH: 20
<212> TYPE: DNA
<213> ORGANISM: Artificial Sequence
<220> FEATURE:
<223> OTHER INFORMATION: Chemically synthesized

<400> SEQUENCE: 51
atcaggtgca cacattaagg                                                 20

<210> SEQ ID NO 52
<211> LENGTH: 20
<212> TYPE: DNA
<213> ORGANISM: Artificial Sequence
<220> FEATURE:
<223> OTHER INFORMATION: Chemically synthesized

<400> SEQUENCE: 52
aaagtcaaga accactgtgg                                                 20

<210> SEQ ID NO 53
<211> LENGTH: 20
<212> TYPE: DNA
<213> ORGANISM: Artificial Sequence
<220> FEATURE:

<223> OTHER INFORMATION: Chemically synthesized

<400> SEQUENCE: 53
gaatgtcagc agctctcatg                                           20

<210> SEQ ID NO 54
<211> LENGTH: 20
<212> TYPE: DNA
<213> ORGANISM: Artificial Sequence
<220> FEATURE:
<223> OTHER INFORMATION: Chemically synthesized

<400> SEQUENCE: 54
gacagacagc aacagagaac                                           20

<210> SEQ ID NO 55
<211> LENGTH: 20
<212> TYPE: DNA
<213> ORGANISM: Artificial Sequence
<220> FEATURE:
<223> OTHER INFORMATION: Chemically synthesized

<400> SEQUENCE: 55
gatggactag aaacatgggc                                           20

<210> SEQ ID NO 56
<211> LENGTH: 20
<212> TYPE: DNA
<213> ORGANISM: Artificial Sequence
<220> FEATURE:
<223> OTHER INFORMATION: Chemically synthesized

<400> SEQUENCE: 56
ccacccatga agacaatgat                                           20

<210> SEQ ID NO 57
<211> LENGTH: 20
<212> TYPE: DNA
<213> ORGANISM: Artificial Sequence
<220> FEATURE:
<223> OTHER INFORMATION: Chemically synthesized

<400> SEQUENCE: 57
cagaagcaga acccaagatg                                           20

<210> SEQ ID NO 58
<211> LENGTH: 20
<212> TYPE: DNA
<213> ORGANISM: Artificial Sequence
<220> FEATURE:
<223> OTHER INFORMATION: Chemically synthesized

<400> SEQUENCE: 58
gctcagctat caagtaacgg                                           20

<210> SEQ ID NO 59
<211> LENGTH: 20
<212> TYPE: DNA
<213> ORGANISM: Artificial Sequence
<220> FEATURE:
<223> OTHER INFORMATION: Chemically synthesized

<400> SEQUENCE: 59
gtattccgtg gatcagcaaa                                           20

<210> SEQ ID NO 60
<211> LENGTH: 20
<212> TYPE: DNA
<213> ORGANISM: Artificial Sequence
<220> FEATURE:
<223> OTHER INFORMATION: Chemically synthesized

<400> SEQUENCE: 60
gtccccaacc acatagaaag                                               20

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized

<400> SEQUENCE: 61
tccttacttc cctaggacaa                                               20

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized

<400> SEQUENCE: 62
cccatctaaa agcgggaaag                                               20

<210> SEQ ID NO 63
<211> LENGTH: 20
<212> TYPE: DNA
<213> ORGANISM: Artificial Sequence
<220> FEATURE:
<223> OTHER INFORMATION: Chemically synthesized

<400> SEQUENCE: 63
gagtacagga gagagtccag                                               20

<210> SEQ ID NO 64
<211> LENGTH: 20
<212> TYPE: DNA
<213> ORGANISM: Artificial Sequence
<220> FEATURE:
<223> OTHER INFORMATION: Chemically synthesized

<400> SEQUENCE: 64
cagaacgact aagaagcacg                                               20

<210> SEQ ID NO 65
<211> LENGTH: 20
<212> TYPE: DNA
<213> ORGANISM: Artificial Sequence
<220> FEATURE:
<223> OTHER INFORMATION: Chemically synthesized

<400> SEQUENCE: 65
gattctctcg cttctaggcc                                               20

<210> SEQ ID NO 66
<211> LENGTH: 20
<212> TYPE: DNA
<213> ORGANISM: Artificial Sequence
<220> FEATURE:
<223> OTHER INFORMATION: Chemically synthesized

```
<400> SEQUENCE: 66
cgaagagact gagtggtacc                                        20

<210> SEQ ID NO 67
<211> LENGTH: 20
<212> TYPE: DNA
<213> ORGANISM: Artificial Sequence
<220> FEATURE:
<223> OTHER INFORMATION: Chemically synthesized

<400> SEQUENCE: 67
aaggaaacct taaggcaatt                                        20

<210> SEQ ID NO 68
<211> LENGTH: 20
<212> TYPE: DNA
<213> ORGANISM: Artificial Sequence
<220> FEATURE:
<223> OTHER INFORMATION: Chemically synthesized

<400> SEQUENCE: 68
atgtccacct gaacactctg                                        20

<210> SEQ ID NO 69
<211> LENGTH: 20
<212> TYPE: DNA
<213> ORGANISM: Artificial Sequence
<220> FEATURE:
<223> OTHER INFORMATION: Chemically synthesized

<400> SEQUENCE: 69
tcctgaatgt ctctgctact                                        20

<210> SEQ ID NO 70
<211> LENGTH: 20
<212> TYPE: DNA
<213> ORGANISM: Artificial Sequence
<220> FEATURE:
<223> OTHER INFORMATION: Chemically synthesized

<400> SEQUENCE: 70
tcagtcactg cagcttgtac                                        20

<210> SEQ ID NO 71
<211> LENGTH: 20
<212> TYPE: DNA
<213> ORGANISM: Artificial Sequence
<220> FEATURE:
<223> OTHER INFORMATION: Chemically synthesized

<400> SEQUENCE: 71
taggatgcct cctcaacctc                                        20

<210> SEQ ID NO 72
<211> LENGTH: 20
<212> TYPE: DNA
<213> ORGANISM: Artificial Sequence
<220> FEATURE:
<223> OTHER INFORMATION: Chemically synthesized

<400> SEQUENCE: 72
aagctctaaa ctccactgga                                        20

<210> SEQ ID NO 73
<211> LENGTH: 20
```

<212> TYPE: DNA
<213> ORGANISM: Artificial Sequence
<220> FEATURE:
<223> OTHER INFORMATION: Chemically synthesized

<400> SEQUENCE: 73
ttcttatccc agacctctcg                                          20

<210> SEQ ID NO 74
<211> LENGTH: 20
<212> TYPE: DNA
<213> ORGANISM: Artificial Sequence
<220> FEATURE:
<223> OTHER INFORMATION: Chemically synthesized

<400> SEQUENCE: 74
gctctatcca ggtagtgaat                                          20

<210> SEQ ID NO 75
<211> LENGTH: 20
<212> TYPE: DNA
<213> ORGANISM: Artificial Sequence
<220> FEATURE:
<223> OTHER INFORMATION: Chemically synthesized

<400> SEQUENCE: 75
cagccacctt atggagcaag                                          20

<210> SEQ ID NO 76
<211> LENGTH: 20
<212> TYPE: DNA
<213> ORGANISM: Artificial Sequence
<220> FEATURE:
<223> OTHER INFORMATION: Chemically synthesized

<400> SEQUENCE: 76
agacagagag ctagacactt                                          20

<210> SEQ ID NO 77
<211> LENGTH: 20
<212> TYPE: DNA
<213> ORGANISM: Artificial Sequence
<220> FEATURE:
<223> OTHER INFORMATION: Chemically synthesized

<400> SEQUENCE: 77
ctagttgctg caatgggagt                                          20

<210> SEQ ID NO 78
<211> LENGTH: 20
<212> TYPE: DNA
<213> ORGANISM: Artificial Sequence
<220> FEATURE:
<223> OTHER INFORMATION: Chemically synthesized

<400> SEQUENCE: 78
gctgcattgt tcaggatact                                          20

<210> SEQ ID NO 79
<211> LENGTH: 20
<212> TYPE: DNA
<213> ORGANISM: Artificial Sequence
<220> FEATURE:
<223> OTHER INFORMATION: Chemically synthesized

<400> SEQUENCE: 79

-continued ctagtcttgc acaccaagag                                               20

<210> SEQ ID NO 80
<211> LENGTH: 20
<212> TYPE: DNA
<213> ORGANISM: Artificial Sequence
<220> FEATURE:
<223> OTHER INFORMATION: Chemically synthesized

<400> SEQUENCE: 80
ctcctgtccc aacttccttg                                               20

<210> SEQ ID NO 81
<211> LENGTH: 20
<212> TYPE: DNA
<213> ORGANISM: Artificial Sequence
<220> FEATURE:
<223> OTHER INFORMATION: Chemically synthesized

<400> SEQUENCE: 81
gacctgctgg aatcagaatc                                               20

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized

<400> SEQUENCE: 82
cctattagac ggcctcaatg                                               20

<210> SEQ ID NO 83
<211> LENGTH: 20
<212> TYPE: DNA
<213> ORGANISM: Artificial Sequence
<220> FEATURE:
<223> OTHER INFORMATION: Chemically synthesized

<400> SEQUENCE: 83
ctcctgccca atatccaaaa                                               20

<210> SEQ ID NO 84
<211> LENGTH: 20
<212> TYPE: DNA
<213> ORGANISM: Artificial Sequence
<220> FEATURE:
<223> OTHER INFORMATION: Chemically synthesized

<400> SEQUENCE: 84
cagatgcctg aatccaaact                                               20

<210> SEQ ID NO 85
<211> LENGTH: 20
<212> TYPE: DNA
<213> ORGANISM: Artificial Sequence
<220> FEATURE:
<223> OTHER INFORMATION: Chemically synthesized

<400> SEQUENCE: 85
caagcctgat tcccaaaaca                                               20

<210> SEQ ID NO 86
<211> LENGTH: 20
<212> TYPE: DNA
<213> ORGANISM: Artificial Sequence
<220> FEATURE:
<223> OTHER INFORMATION: Chemically synthesized

<400> SEQUENCE: 86
ggtggaaatc ttaatcccca					20

<210> SEQ ID NO 87
<211> LENGTH: 20
<212> TYPE: DNA
<213> ORGANISM: Artificial Sequence
<220> FEATURE:
<223> OTHER INFORMATION: Chemically synthesized

<400> SEQUENCE: 87
cgagcttgtt aagtctcgtc					20

<210> SEQ ID NO 88
<211> LENGTH: 20
<212> TYPE: DNA
<213> ORGANISM: Artificial Sequence
<220> FEATURE:
<223> OTHER INFORMATION: Chemically synthesized

<400> SEQUENCE: 88
gagtggtttc agcagaatct					20

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized

<400> SEQUENCE: 89
accaccgaga aggattctaa					20

<210> SEQ ID NO 90
<211> LENGTH: 20
<212> TYPE: DNA
<213> ORGANISM: Artificial Sequence
<220> FEATURE:
<223> OTHER INFORMATION: Chemically synthesized

<400> SEQUENCE: 90
ttctcacaca gatgagtgcg					20

<210> SEQ ID NO 91
<211> LENGTH: 20
<212> TYPE: DNA
<213> ORGANISM: Artificial Sequence
<220> FEATURE:
<223> OTHER INFORMATION: Chemically synthesized

<400> SEQUENCE: 91
taggaaaaca gaccctttgg					20

<210> SEQ ID NO 92
<211> LENGTH: 20
<212> TYPE: DNA
<213> ORGANISM: Artificial Sequence
<220> FEATURE:
<223> OTHER INFORMATION: Chemically synthesized

<400> SEQUENCE: 92
tcaagagatc cccaaacacg					20

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized

<400> SEQUENCE: 93
atcacagacc agaatgcctg                                               20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized

<400> SEQUENCE: 94
cattctacca cacatggagg                                               20

<210> SEQ ID NO 95
<211> LENGTH: 20
<212> TYPE: DNA
<213> ORGANISM: Artificial Sequence
<220> FEATURE:
<223> OTHER INFORMATION: Chemically synthesized

<400> SEQUENCE: 95
gagctaacac ctgacaactt                                               20

<210> SEQ ID NO 96
<211> LENGTH: 20
<212> TYPE: DNA
<213> ORGANISM: Artificial Sequence
<220> FEATURE:
<223> OTHER INFORMATION: Chemically synthesized

<400> SEQUENCE: 96
ctcactcagg ctaaaatcct                                               20

<210> SEQ ID NO 97
<211> LENGTH: 20
<212> TYPE: DNA
<213> ORGANISM: Artificial Sequence
<220> FEATURE:
<223> OTHER INFORMATION: Chemically synthesized

<400> SEQUENCE: 97
atgctttgga aaaggctaca                                               20

<210> SEQ ID NO 98
<211> LENGTH: 20
<212> TYPE: DNA
<213> ORGANISM: Artificial Sequence
<220> FEATURE:
<223> OTHER INFORMATION: Chemically synthesized

<400> SEQUENCE: 98
actgacttcg ttcctacact                                               20

<210> SEQ ID NO 99
<211> LENGTH: 20
<212> TYPE: DNA
<213> ORGANISM: Artificial Sequence
<220> FEATURE:
<223> OTHER INFORMATION: Chemically synthesized

```
<400> SEQUENCE: 99
ggacaagcaa actgaaaagc                                                  20

<210> SEQ ID NO 100
<211> LENGTH: 20
<212> TYPE: DNA
<213> ORGANISM: Artificial Sequence
<220> FEATURE:
<223> OTHER INFORMATION: Chemically synthesized

<400> SEQUENCE: 100
gagcacaact gaagaaccaa                                                  20

<210> SEQ ID NO 101
<211> LENGTH: 20
<212> TYPE: DNA
<213> ORGANISM: Artificial Sequence
<220> FEATURE:
<223> OTHER INFORMATION: Chemically synthesized

<400> SEQUENCE: 101
tatcgctcgt gtgtaaaagc                                                  20

<210> SEQ ID NO 102
<211> LENGTH: 20
<212> TYPE: DNA
<213> ORGANISM: Artificial Sequence
<220> FEATURE:
<223> OTHER INFORMATION: Chemically synthesized

<400> SEQUENCE: 102
tgcacaattc agaatgatgc                                                  20

<210> SEQ ID NO 103
<211> LENGTH: 20
<212> TYPE: DNA
<213> ORGANISM: Artificial Sequence
<220> FEATURE:
<223> OTHER INFORMATION: Chemically synthesized

<400> SEQUENCE: 103
agcccaacgt tcatctttta                                                  20

<210> SEQ ID NO 104
<211> LENGTH: 20
<212> TYPE: DNA
<213> ORGANISM: Artificial Sequence
<220> FEATURE:
<223> OTHER INFORMATION: Chemically synthesized

<400> SEQUENCE: 104
agaggctgga gtttcttaga                                                  20

<210> SEQ ID NO 105
<211> LENGTH: 20
<212> TYPE: DNA
<213> ORGANISM: Artificial Sequence
<220> FEATURE:
<223> OTHER INFORMATION: Chemically synthesized

<400> SEQUENCE: 105
aattcagtct gaccacaacc                                                  20

<210> SEQ ID NO 106
```

<211> LENGTH: 20
<212> TYPE: DNA
<213> ORGANISM: Artificial Sequence
<220> FEATURE:
<223> OTHER INFORMATION: Chemically synthesized

<400> SEQUENCE: 106
atcctcaatc agcatgccta                                               20

<210> SEQ ID NO 107
<211> LENGTH: 20
<212> TYPE: DNA
<213> ORGANISM: Artificial Sequence
<220> FEATURE:
<223> OTHER INFORMATION: Chemically synthesized

<400> SEQUENCE: 107
tggttgtcac ctactgagaa                                               20

<210> SEQ ID NO 108
<211> LENGTH: 20
<212> TYPE: DNA
<213> ORGANISM: Artificial Sequence
<220> FEATURE:
<223> OTHER INFORMATION: Chemically synthesized

<400> SEQUENCE: 108
cacagaatct ctgtggcttg                                               20

<210> SEQ ID NO 109
<211> LENGTH: 20
<212> TYPE: DNA
<213> ORGANISM: Artificial Sequence
<220> FEATURE:
<223> OTHER INFORMATION: Chemically synthesized

<400> SEQUENCE: 109
cttatgaccc ctgcagtcag                                               20

<210> SEQ ID NO 110
<211> LENGTH: 20
<212> TYPE: DNA
<213> ORGANISM: Artificial Sequence
<220> FEATURE:
<223> OTHER INFORMATION: Chemically synthesized

<400> SEQUENCE: 110
acgtgaagtt tatgcccaat                                               20

<210> SEQ ID NO 111
<211> LENGTH: 20
<212> TYPE: DNA
<213> ORGANISM: Artificial Sequence
<220> FEATURE:
<223> OTHER INFORMATION: Chemically synthesized

<400> SEQUENCE: 111
tctatctagc catccatcca                                               20

<210> SEQ ID NO 112
<211> LENGTH: 20
<212> TYPE: DNA
<213> ORGANISM: Artificial Sequence
<220> FEATURE:
<223> OTHER INFORMATION: Chemically synthesized

<400> SEQUENCE: 112
gctttggatc caatggaaga					20

<210> SEQ ID NO 113
<211> LENGTH: 20
<212> TYPE: DNA
<213> ORGANISM: Artificial Sequence
<220> FEATURE:
<223> OTHER INFORMATION: Chemically synthesized

<400> SEQUENCE: 113
gaccttgaag aagccagaaa					20

<210> SEQ ID NO 114
<211> LENGTH: 20
<212> TYPE: DNA
<213> ORGANISM: Artificial Sequence
<220> FEATURE:
<223> OTHER INFORMATION: Chemically synthesized

<400> SEQUENCE: 114
cctgaagctg agaagttgat					20

<210> SEQ ID NO 115
<211> LENGTH: 20
<212> TYPE: DNA
<213> ORGANISM: Artificial Sequence
<220> FEATURE:
<223> OTHER INFORMATION: Chemically synthesized

<400> SEQUENCE: 115
caagggaaaa gggcttgaaa					20

<210> SEQ ID NO 116
<211> LENGTH: 20
<212> TYPE: DNA
<213> ORGANISM: Artificial Sequence
<220> FEATURE:
<223> OTHER INFORMATION: Chemically synthesized

<400> SEQUENCE: 116
gagaaagctt ccagcagatt					20

<210> SEQ ID NO 117
<211> LENGTH: 20
<212> TYPE: DNA
<213> ORGANISM: Artificial Sequence
<220> FEATURE:
<223> OTHER INFORMATION: Chemically synthesized

<400> SEQUENCE: 117
aggtcaaggg gtctagaaat					20

<210> SEQ ID NO 118
<211> LENGTH: 20
<212> TYPE: DNA
<213> ORGANISM: Artificial Sequence
<220> FEATURE:
<223> OTHER INFORMATION: Chemically synthesized

<400> SEQUENCE: 118
agatgaataa aggctgagcc					20

<210> SEQ ID NO 119
<211> LENGTH: 20
<212> TYPE: DNA

<213> ORGANISM: Artificial Sequence
<220> FEATURE:
<223> OTHER INFORMATION: Chemically synthesized

<400> SEQUENCE: 119
ctggaagtat ggggtaggaa                                               20

<210> SEQ ID NO 120
<211> LENGTH: 20
<212> TYPE: DNA
<213> ORGANISM: Artificial Sequence
<220> FEATURE:
<223> OTHER INFORMATION: Chemically synthesized

<400> SEQUENCE: 120
tcctaggaat cagagaaggg                                               20

<210> SEQ ID NO 121
<211> LENGTH: 20
<212> TYPE: DNA
<213> ORGANISM: Artificial Sequence
<220> FEATURE:
<223> OTHER INFORMATION: Chemically synthesized

<400> SEQUENCE: 121
ggaatggtgg aaagtgacaa                                               20

<210> SEQ ID NO 122
<211> LENGTH: 20
<212> TYPE: DNA
<213> ORGANISM: Artificial Sequence
<220> FEATURE:
<223> OTHER INFORMATION: Chemically synthesized

<400> SEQUENCE: 122
tgatcagaga cacaggagat                                               20

<210> SEQ ID NO 123
<211> LENGTH: 20
<212> TYPE: DNA
<213> ORGANISM: Artificial Sequence
<220> FEATURE:
<223> OTHER INFORMATION: Chemically synthesized

<400> SEQUENCE: 123
gcaggtcttt ggaagtgatc                                               20

<210> SEQ ID NO 124
<211> LENGTH: 20
<212> TYPE: DNA
<213> ORGANISM: Artificial Sequence
<220> FEATURE:
<223> OTHER INFORMATION: Chemically synthesized

<400> SEQUENCE: 124
tggggagaag tctaggattg                                               20

<210> SEQ ID NO 125
<211> LENGTH: 20
<212> TYPE: DNA
<213> ORGANISM: Artificial Sequence
<220> FEATURE:
<223> OTHER INFORMATION: Chemically synthesized

<400> SEQUENCE: 125
gatctgcaag atgaggaagg                                               20

<210> SEQ ID NO 126
<211> LENGTH: 20
<212> TYPE: DNA
<213> ORGANISM: Artificial Sequence
<220> FEATURE:
<223> OTHER INFORMATION: Chemically synthesized

<400> SEQUENCE: 126
actccaaatt ggagttctgg                                              20

<210> SEQ ID NO 127
<211> LENGTH: 20
<212> TYPE: DNA
<213> ORGANISM: Artificial Sequence
<220> FEATURE:
<223> OTHER INFORMATION: Chemically synthesized

<400> SEQUENCE: 127
attgtagtga ccaaggaaca                                              20

<210> SEQ ID NO 128
<211> LENGTH: 20
<212> TYPE: DNA
<213> ORGANISM: Artificial Sequence
<220> FEATURE:
<223> OTHER INFORMATION: Chemically synthesized

<400> SEQUENCE: 128
ctgaatcgag taagccttgg                                              20

<210> SEQ ID NO 129
<211> LENGTH: 20
<212> TYPE: DNA
<213> ORGANISM: Artificial Sequence
<220> FEATURE:
<223> OTHER INFORMATION: Chemically synthesized

<400> SEQUENCE: 129
caaccgggga gataagagac                                              20

<210> SEQ ID NO 130
<211> LENGTH: 20
<212> TYPE: DNA
<213> ORGANISM: Artificial Sequence
<220> FEATURE:
<223> OTHER INFORMATION: Chemically synthesized

<400> SEQUENCE: 130
cctacttgga gcaagtcatg                                              20

<210> SEQ ID NO 131
<211> LENGTH: 20
<212> TYPE: DNA
<213> ORGANISM: Artificial Sequence
<220> FEATURE:
<223> OTHER INFORMATION: Chemically synthesized

<400> SEQUENCE: 131
aattaggatg gcaggccttc                                              20

<210> SEQ ID NO 132
<211> LENGTH: 20
<212> TYPE: DNA
<213> ORGANISM: Artificial Sequence
<220> FEATURE:

<223> OTHER INFORMATION: Chemically synthesized

<400> SEQUENCE: 132
aaaatgagag gcggaggaag					20

<210> SEQ ID NO 133
<211> LENGTH: 20
<212> TYPE: DNA
<213> ORGANISM: Artificial Sequence
<220> FEATURE:
<223> OTHER INFORMATION: Chemically synthesized

<400> SEQUENCE: 133
cgtcctctta ggacacctaa					20

<210> SEQ ID NO 134
<211> LENGTH: 20
<212> TYPE: DNA
<213> ORGANISM: Artificial Sequence
<220> FEATURE:
<223> OTHER INFORMATION: Chemically synthesized

<400> SEQUENCE: 134
gctcctaaac ttggctagtc					20

<210> SEQ ID NO 135
<211> LENGTH: 20
<212> TYPE: DNA
<213> ORGANISM: Artificial Sequence
<220> FEATURE:
<223> OTHER INFORMATION: Chemically synthesized

<400> SEQUENCE: 135
tatcctggtc aatgggagga					20

<210> SEQ ID NO 136
<211> LENGTH: 20
<212> TYPE: DNA
<213> ORGANISM: Artificial Sequence
<220> FEATURE:
<223> OTHER INFORMATION: Chemically synthesized

<400> SEQUENCE: 136
gcttagcaaa tccctcaacc					20

<210> SEQ ID NO 137
<211> LENGTH: 20
<212> TYPE: DNA
<213> ORGANISM: Artificial Sequence
<220> FEATURE:
<223> OTHER INFORMATION: Chemically synthesized

<400> SEQUENCE: 137
catcccataa ccaggaatgt					20

<210> SEQ ID NO 138
<211> LENGTH: 20
<212> TYPE: DNA
<213> ORGANISM: Artificial Sequence
<220> FEATURE:
<223> OTHER INFORMATION: Chemically synthesized

<400> SEQUENCE: 138
cctctttaat caccactccc					20

<210> SEQ ID NO 139
<211> LENGTH: 20
<212> TYPE: DNA
<213> ORGANISM: Artificial Sequence
<220> FEATURE:
<223> OTHER INFORMATION: Chemically synthesized

<400> SEQUENCE: 139
aacagaccta aagggaggat                                                 20

<210> SEQ ID NO 140
<211> LENGTH: 20
<212> TYPE: DNA
<213> ORGANISM: Artificial Sequence
<220> FEATURE:
<223> OTHER INFORMATION: Chemically synthesized

<400> SEQUENCE: 140
gtttggcagg ttacccagtg                                                 20

<210> SEQ ID NO 141
<211> LENGTH: 20
<212> TYPE: DNA
<213> ORGANISM: Artificial Sequence
<220> FEATURE:
<223> OTHER INFORMATION: Chemically synthesized

<400> SEQUENCE: 141
tataccagga acctaggagg                                                 20

<210> SEQ ID NO 142
<211> LENGTH: 20
<212> TYPE: DNA
<213> ORGANISM: Artificial Sequence
<220> FEATURE:
<223> OTHER INFORMATION: Chemically synthesized

<400> SEQUENCE: 142
tccccagcat catatctcat                                                 20

<210> SEQ ID NO 143
<211> LENGTH: 20
<212> TYPE: DNA
<213> ORGANISM: Artificial Sequence
<220> FEATURE:
<223> OTHER INFORMATION: Chemically synthesized

<400> SEQUENCE: 143
tatagcaact ggtgtctcca                                                 20

<210> SEQ ID NO 144
<211> LENGTH: 20
<212> TYPE: DNA
<213> ORGANISM: Artificial Sequence
<220> FEATURE:
<223> OTHER INFORMATION: Chemically synthesized

<400> SEQUENCE: 144
cctgtttcac atctggatcc                                                 20

<210> SEQ ID NO 145
<211> LENGTH: 20
<212> TYPE: DNA
<213> ORGANISM: Artificial Sequence
<220> FEATURE:
<223> OTHER INFORMATION: Chemically synthesized

```
<400> SEQUENCE: 145
gaatgcgaaa catctccagc                                                 20

<210> SEQ ID NO 146
<211> LENGTH: 20
<212> TYPE: DNA
<213> ORGANISM: Artificial Sequence
<220> FEATURE:
<223> OTHER INFORMATION: Chemically synthesized

<400> SEQUENCE: 146
aaacttctca ggaaaacgga                                                 20

<210> SEQ ID NO 147
<211> LENGTH: 20
<212> TYPE: DNA
<213> ORGANISM: Artificial Sequence
<220> FEATURE:
<223> OTHER INFORMATION: Chemically synthesized

<400> SEQUENCE: 147
ctcttctgac accacagact                                                 20

<210> SEQ ID NO 148
<211> LENGTH: 20
<212> TYPE: DNA
<213> ORGANISM: Artificial Sequence
<220> FEATURE:
<223> OTHER INFORMATION: Chemically synthesized

<400> SEQUENCE: 148
gggggaaggt ggatagaaag                                                 20

<210> SEQ ID NO 149
<211> LENGTH: 20
<212> TYPE: DNA
<213> ORGANISM: Artificial Sequence
<220> FEATURE:
<223> OTHER INFORMATION: Chemically synthesized

<400> SEQUENCE: 149
gaacacagcc tcagttactg                                                 20

<210> SEQ ID NO 150
<211> LENGTH: 20
<212> TYPE: DNA
<213> ORGANISM: Artificial Sequence
<220> FEATURE:
<223> OTHER INFORMATION: Chemically synthesized

<400> SEQUENCE: 150
ctgaaactgg caaactcaca                                                 20

<210> SEQ ID NO 151
<211> LENGTH: 20
<212> TYPE: DNA
<213> ORGANISM: Artificial Sequence
<220> FEATURE:
<223> OTHER INFORMATION: Chemically synthesized

<400> SEQUENCE: 151
gtgctttcca gtaagttgga                                                 20

<210> SEQ ID NO 152
<211> LENGTH: 20
```

```
<212> TYPE: DNA
<213> ORGANISM: Artificial Sequence
<220> FEATURE:
<223> OTHER INFORMATION: Chemically synthesized

<400> SEQUENCE: 152
cacgttccaa gacaaagaca                                              20

<210> SEQ ID NO 153
<211> LENGTH: 20
<212> TYPE: DNA
<213> ORGANISM: Artificial Sequence
<220> FEATURE:
<223> OTHER INFORMATION: Chemically synthesized

<400> SEQUENCE: 153
ccacttgact gcaacttgaa                                              20

<210> SEQ ID NO 154
<211> LENGTH: 20
<212> TYPE: DNA
<213> ORGANISM: Artificial Sequence
<220> FEATURE:
<223> OTHER INFORMATION: Chemically synthesized

<400> SEQUENCE: 154
cgctagagaa agctcagaag                                              20

<210> SEQ ID NO 155
<211> LENGTH: 20
<212> TYPE: DNA
<213> ORGANISM: Artificial Sequence
<220> FEATURE:
<223> OTHER INFORMATION: Chemically synthesized

<400> SEQUENCE: 155
cggagaagca aagtgagaag                                              20

<210> SEQ ID NO 156
<211> LENGTH: 20
<212> TYPE: DNA
<213> ORGANISM: Artificial Sequence
<220> FEATURE:
<223> OTHER INFORMATION: Chemically synthesized

<400> SEQUENCE: 156
aactccagat tccagaccaa                                              20

<210> SEQ ID NO 157
<211> LENGTH: 20
<212> TYPE: DNA
<213> ORGANISM: Artificial Sequence
<220> FEATURE:
<223> OTHER INFORMATION: Chemically synthesized

<400> SEQUENCE: 157
tgacagcaag aaccgaagag                                              20

<210> SEQ ID NO 158
<211> LENGTH: 20
<212> TYPE: DNA
<213> ORGANISM: Artificial Sequence
<220> FEATURE:
<223> OTHER INFORMATION: Chemically synthesized

<400> SEQUENCE: 158
```

-continued taggctggat tctatccagg                                        20

<210> SEQ ID NO 159
<211> LENGTH: 20
<212> TYPE: DNA
<213> ORGANISM: Artificial Sequence
<220> FEATURE:
<223> OTHER INFORMATION: Chemically synthesized

<400> SEQUENCE: 159
tcaaccagta aatgcccatc                                        20

<210> SEQ ID NO 160
<211> LENGTH: 20
<212> TYPE: DNA
<213> ORGANISM: Artificial Sequence
<220> FEATURE:
<223> OTHER INFORMATION: Chemically synthesized

<400> SEQUENCE: 160
ccctttcctc acatgctgag                                        20

<210> SEQ ID NO 161
<211> LENGTH: 20
<212> TYPE: DNA
<213> ORGANISM: Artificial Sequence
<220> FEATURE:
<223> OTHER INFORMATION: Chemically synthesized

<400> SEQUENCE: 161
gttgggtgca acaagagaag                                        20

<210> SEQ ID NO 162
<211> LENGTH: 20
<212> TYPE: DNA
<213> ORGANISM: Artificial Sequence
<220> FEATURE:
<223> OTHER INFORMATION: Chemically synthesized

<400> SEQUENCE: 162
ctatgctgcg cgacttattc                                        20

<210> SEQ ID NO 163
<211> LENGTH: 20
<212> TYPE: DNA
<213> ORGANISM: Artificial Sequence
<220> FEATURE:
<223> OTHER INFORMATION: Chemically synthesized

<400> SEQUENCE: 163
tttcatctgc ttctcacagc                                        20

<210> SEQ ID NO 164
<211> LENGTH: 20
<212> TYPE: DNA
<213> ORGANISM: Artificial Sequence
<220> FEATURE:
<223> OTHER INFORMATION: Chemically synthesized

<400> SEQUENCE: 164
tatgtaccac agcgttaagc                                        20

<210> SEQ ID NO 165
<211> LENGTH: 20
<212> TYPE: DNA
<213> ORGANISM: Artificial Sequence

```
<220> FEATURE:
<223> OTHER INFORMATION: Chemically synthesized

<400> SEQUENCE: 165
ccatagagcc gtttgattct                                              20

<210> SEQ ID NO 166
<211> LENGTH: 20
<212> TYPE: DNA
<213> ORGANISM: Artificial Sequence
<220> FEATURE:
<223> OTHER INFORMATION: Chemically synthesized

<400> SEQUENCE: 166
agtccaggtt ctcctatctc                                              20

<210> SEQ ID NO 167
<211> LENGTH: 20
<212> TYPE: DNA
<213> ORGANISM: Artificial Sequence
<220> FEATURE:
<223> OTHER INFORMATION: Chemically synthesized

<400> SEQUENCE: 167
agctggagat ctggacataa                                              20

<210> SEQ ID NO 168
<211> LENGTH: 20
<212> TYPE: DNA
<213> ORGANISM: Artificial Sequence
<220> FEATURE:
<223> OTHER INFORMATION: Chemically synthesized

<400> SEQUENCE: 168
cctttgacag caaggaaacc                                              20

<210> SEQ ID NO 169
<211> LENGTH: 20
<212> TYPE: DNA
<213> ORGANISM: Artificial Sequence
<220> FEATURE:
<223> OTHER INFORMATION: Chemically synthesized

<400> SEQUENCE: 169
gttcaggaag ggaacaatgg                                              20

<210> SEQ ID NO 170
<211> LENGTH: 20
<212> TYPE: DNA
<213> ORGANISM: Artificial Sequence
<220> FEATURE:
<223> OTHER INFORMATION: Chemically synthesized

<400> SEQUENCE: 170
ttttactgtg aacctgaccc                                              20

<210> SEQ ID NO 171
<211> LENGTH: 20
<212> TYPE: DNA
<213> ORGANISM: Artificial Sequence
<220> FEATURE:
<223> OTHER INFORMATION: Chemically synthesized

<400> SEQUENCE: 171
aaaccacctc tgaaactgac                                              20
```

<210> SEQ ID NO 172
<211> LENGTH: 20
<212> TYPE: DNA
<213> ORGANISM: Artificial Sequence
<220> FEATURE:
<223> OTHER INFORMATION: Chemically synthesized

<400> SEQUENCE: 172
aatctttggt caagtccagg                                              20

<210> SEQ ID NO 173
<211> LENGTH: 20
<212> TYPE: DNA
<213> ORGANISM: Artificial Sequence
<220> FEATURE:
<223> OTHER INFORMATION: Chemically synthesized

<400> SEQUENCE: 173
ggtttacaga tgcagaggtg                                              20

<210> SEQ ID NO 174
<211> LENGTH: 20
<212> TYPE: DNA
<213> ORGANISM: Artificial Sequence
<220> FEATURE:
<223> OTHER INFORMATION: Chemically synthesized

<400> SEQUENCE: 174
aactgcaatc caaacgtttg                                              20

<210> SEQ ID NO 175
<211> LENGTH: 20
<212> TYPE: DNA
<213> ORGANISM: Artificial Sequence
<220> FEATURE:
<223> OTHER INFORMATION: Chemically synthesized

<400> SEQUENCE: 175
agaactagga caagacctca                                              20

<210> SEQ ID NO 176
<211> LENGTH: 20
<212> TYPE: DNA
<213> ORGANISM: Artificial Sequence
<220> FEATURE:
<223> OTHER INFORMATION: Chemically synthesized

<400> SEQUENCE: 176
catcttcttt caccctgagg                                              20

<210> SEQ ID NO 177
<211> LENGTH: 20
<212> TYPE: DNA
<213> ORGANISM: Artificial Sequence
<220> FEATURE:
<223> OTHER INFORMATION: Chemically synthesized

<400> SEQUENCE: 177
tctggatcgc actaacagag                                              20

<210> SEQ ID NO 178
<211> LENGTH: 20
<212> TYPE: DNA
<213> ORGANISM: Artificial Sequence
<220> FEATURE:
<223> OTHER INFORMATION: Chemically synthesized -continued

```
<400> SEQUENCE: 178
catcctaaac cgtggtaccc                                                20

<210> SEQ ID NO 179
<211> LENGTH: 20
<212> TYPE: DNA
<213> ORGANISM: Artificial Sequence
<220> FEATURE:
<223> OTHER INFORMATION: Chemically synthesized

<400> SEQUENCE: 179
ggagaaagtc aagcatgtga                                                20

<210> SEQ ID NO 180
<211> LENGTH: 20
<212> TYPE: DNA
<213> ORGANISM: Artificial Sequence
<220> FEATURE:
<223> OTHER INFORMATION: Chemically synthesized

<400> SEQUENCE: 180
tttgaacctc agtccccaaa                                                20

<210> SEQ ID NO 181
<211> LENGTH: 20
<212> TYPE: DNA
<213> ORGANISM: Artificial Sequence
<220> FEATURE:
<223> OTHER INFORMATION: Chemically synthesized

<400> SEQUENCE: 181
gtacaaagag aggctggaac                                                20

<210> SEQ ID NO 182
<211> LENGTH: 20
<212> TYPE: DNA
<213> ORGANISM: Artificial Sequence
<220> FEATURE:
<223> OTHER INFORMATION: Chemically synthesized

<400> SEQUENCE: 182
cctcaacaca actatgctgt                                                20

<210> SEQ ID NO 183
<211> LENGTH: 20
<212> TYPE: DNA
<213> ORGANISM: Artificial Sequence
<220> FEATURE:
<223> OTHER INFORMATION: Chemically synthesized

<400> SEQUENCE: 183
ctaccccata tcccaaatgc                                                20

<210> SEQ ID NO 184
<211> LENGTH: 20
<212> TYPE: DNA
<213> ORGANISM: Artificial Sequence
<220> FEATURE:
<223> OTHER INFORMATION: Chemically synthesized

<400> SEQUENCE: 184
cacgattcag tcatctccac                                                20

<210> SEQ ID NO 185
```

```
<211> LENGTH: 20
<212> TYPE: DNA
<213> ORGANISM: Artificial Sequence
<220> FEATURE:
<223> OTHER INFORMATION: Chemically synthesized

<400> SEQUENCE: 185
aagaccaaaa cagtgggaaa                                                 20

<210> SEQ ID NO 186
<211> LENGTH: 20
<212> TYPE: DNA
<213> ORGANISM: Artificial Sequence
<220> FEATURE:
<223> OTHER INFORMATION: Chemically synthesized

<400> SEQUENCE: 186
gaagtatggt ttgtgccagg                                                 20

<210> SEQ ID NO 187
<211> LENGTH: 20
<212> TYPE: DNA
<213> ORGANISM: Artificial Sequence
<220> FEATURE:
<223> OTHER INFORMATION: Chemically synthesized

<400> SEQUENCE: 187
gaaagagctc agaggagaca                                                 20

<210> SEQ ID NO 188
<211> LENGTH: 20
<212> TYPE: DNA
<213> ORGANISM: Artificial Sequence
<220> FEATURE:
<223> OTHER INFORMATION: Chemically synthesized

<400> SEQUENCE: 188
caagtggtga cacaaccaag                                                 20

<210> SEQ ID NO 189
<211> LENGTH: 20
<212> TYPE: DNA
<213> ORGANISM: Artificial Sequence
<220> FEATURE:
<223> OTHER INFORMATION: Chemically synthesized

<400> SEQUENCE: 189
tcgaatgtca catcacacaa                                                 20

<210> SEQ ID NO 190
<211> LENGTH: 20
<212> TYPE: DNA
<213> ORGANISM: Artificial Sequence
<220> FEATURE:
<223> OTHER INFORMATION: Chemically synthesized

<400> SEQUENCE: 190
aaaaacttgg agtaccaagt                                                 20

<210> SEQ ID NO 191
<211> LENGTH: 20
<212> TYPE: DNA
<213> ORGANISM: Artificial Sequence
<220> FEATURE:
<223> OTHER INFORMATION: Chemically synthesized

<400> SEQUENCE: 191
```
ttcatctgtc tctggtttcc 20

<210> SEQ ID NO 192
<211> LENGTH: 20
<212> TYPE: DNA
<213> ORGANISM: Artificial Sequence
<220> FEATURE:
<223> OTHER INFORMATION: Chemically synthesized

<400> SEQUENCE: 192
aaaccacctg taagcaaaat 20

<210> SEQ ID NO 193
<211> LENGTH: 20
<212> TYPE: DNA
<213> ORGANISM: Artificial Sequence
<220> FEATURE:
<223> OTHER INFORMATION: Chemically synthesized

<400> SEQUENCE: 193
gcttactcat ggaaactcgg 20

<210> SEQ ID NO 194
<211> LENGTH: 20
<212> TYPE: DNA
<213> ORGANISM: Artificial Sequence
<220> FEATURE:
<223> OTHER INFORMATION: Chemically synthesized

<400> SEQUENCE: 194
tcatagtcag tatctgcccc 20

<210> SEQ ID NO 195
<211> LENGTH: 20
<212> TYPE: DNA
<213> ORGANISM: Artificial Sequence
<220> FEATURE:
<223> OTHER INFORMATION: Chemically synthesized

<400> SEQUENCE: 195
atccgatctc gcgagaataa 20

<210> SEQ ID NO 196
<211> LENGTH: 20
<212> TYPE: DNA
<213> ORGANISM: Artificial Sequence
<220> FEATURE:
<223> OTHER INFORMATION: Chemically synthesized

<400> SEQUENCE: 196
gagagaagtg tgagcgtaag 20

<210> SEQ ID NO 197
<211> LENGTH: 20
<212> TYPE: DNA
<213> ORGANISM: Artificial Sequence
<220> FEATURE:
<223> OTHER INFORMATION: Chemically synthesized

<400> SEQUENCE: 197
atagagtaca tgggcacctt 20

<210> SEQ ID NO 198
<211> LENGTH: 20
<212> TYPE: DNA

<213> ORGANISM: Artificial Sequence
<220> FEATURE:
<223> OTHER INFORMATION: Chemically synthesized

<400> SEQUENCE: 198
gtaccaaatt tagggacgg          20

<210> SEQ ID NO 199
<211> LENGTH: 20
<212> TYPE: DNA
<213> ORGANISM: Artificial Sequence
<220> FEATURE:
<223> OTHER INFORMATION: Chemically synthesized

<400> SEQUENCE: 199
tggaatcaca aaaccttcct          20

<210> SEQ ID NO 200
<211> LENGTH: 20
<212> TYPE: DNA
<213> ORGANISM: Artificial Sequence
<220> FEATURE:
<223> OTHER INFORMATION: Chemically synthesized

<400> SEQUENCE: 200
cgtactggca caacaactag          20

<210> SEQ ID NO 201
<211> LENGTH: 20
<212> TYPE: DNA
<213> ORGANISM: Artificial Sequence
<220> FEATURE:
<223> OTHER INFORMATION: Chemically synthesized

<400> SEQUENCE: 201
gggagaatga acctcacaag          20

<210> SEQ ID NO 202
<211> LENGTH: 20
<212> TYPE: DNA
<213> ORGANISM: Artificial Sequence
<220> FEATURE:
<223> OTHER INFORMATION: Chemically synthesized

<400> SEQUENCE: 202
gacacaactc tcatcactgg          20

<210> SEQ ID NO 203
<211> LENGTH: 20
<212> TYPE: DNA
<213> ORGANISM: Artificial Sequence
<220> FEATURE:
<223> OTHER INFORMATION: Chemically synthesized

<400> SEQUENCE: 203
aaggctggtt ccatttatcc          20

<210> SEQ ID NO 204
<211> LENGTH: 20
<212> TYPE: DNA
<213> ORGANISM: Artificial Sequence
<220> FEATURE:
<223> OTHER INFORMATION: Chemically synthesized

<400> SEQUENCE: 204
tttcctactt cacaagtgcc          20

<210> SEQ ID NO 205
<211> LENGTH: 20
<212> TYPE: DNA
<213> ORGANISM: Artificial Sequence
<220> FEATURE:
<223> OTHER INFORMATION: Chemically synthesized

<400> SEQUENCE: 205
acctaagaaa cagggcaaag                                              20

<210> SEQ ID NO 206
<211> LENGTH: 20
<212> TYPE: DNA
<213> ORGANISM: Artificial Sequence
<220> FEATURE:
<223> OTHER INFORMATION: Chemically synthesized

<400> SEQUENCE: 206
aggcctatct ttagctctgg                                              20

<210> SEQ ID NO 207
<211> LENGTH: 20
<212> TYPE: DNA
<213> ORGANISM: Artificial Sequence
<220> FEATURE:
<223> OTHER INFORMATION: Chemically synthesized

<400> SEQUENCE: 207
gcccagaaat tccacttcat                                              20

<210> SEQ ID NO 208
<211> LENGTH: 20
<212> TYPE: DNA
<213> ORGANISM: Artificial Sequence
<220> FEATURE:
<223> OTHER INFORMATION: Chemically synthesized

<400> SEQUENCE: 208
aaccctgtta tcaccatcac                                              20

<210> SEQ ID NO 209
<211> LENGTH: 20
<212> TYPE: DNA
<213> ORGANISM: Artificial Sequence
<220> FEATURE:
<223> OTHER INFORMATION: Chemically synthesized

<400> SEQUENCE: 209
gaggactcac tgagcgaaag                                              20

<210> SEQ ID NO 210
<211> LENGTH: 20
<212> TYPE: DNA
<213> ORGANISM: Artificial Sequence
<220> FEATURE:
<223> OTHER INFORMATION: Chemically synthesized

<400> SEQUENCE: 210
tgcatttttc caggaactaa                                              20

<210> SEQ ID NO 211
<211> LENGTH: 20
<212> TYPE: DNA
<213> ORGANISM: Artificial Sequence
<220> FEATURE:

-continued

```
<223> OTHER INFORMATION: Chemically synthesized

<400> SEQUENCE: 211
tgagcccgta ttctcattga                                           20

<210> SEQ ID NO 212
<211> LENGTH: 20
<212> TYPE: DNA
<213> ORGANISM: Artificial Sequence
<220> FEATURE:
<223> OTHER INFORMATION: Chemically synthesized

<400> SEQUENCE: 212
aattaaaact cacaggaggc                                           20

<210> SEQ ID NO 213
<211> LENGTH: 20
<212> TYPE: DNA
<213> ORGANISM: Artificial Sequence
<220> FEATURE:
<223> OTHER INFORMATION: Chemically synthesized

<400> SEQUENCE: 213
atgccaagct aacaatgctc                                           20

<210> SEQ ID NO 214
<211> LENGTH: 20
<212> TYPE: DNA
<213> ORGANISM: Artificial Sequence
<220> FEATURE:
<223> OTHER INFORMATION: Chemically synthesized

<400> SEQUENCE: 214
gtgtccatcg ttaccagggc                                           20

<210> SEQ ID NO 215
<211> LENGTH: 20
<212> TYPE: DNA
<213> ORGANISM: Artificial Sequence
<220> FEATURE:
<223> OTHER INFORMATION: Chemically synthesized

<400> SEQUENCE: 215
taggcaaaga ggtagagccc                                           20

<210> SEQ ID NO 216
<211> LENGTH: 20
<212> TYPE: DNA
<213> ORGANISM: Artificial Sequence
<220> FEATURE:
<223> OTHER INFORMATION: Chemically synthesized

<400> SEQUENCE: 216
aaggactgca gagtgtcaat                                           20

<210> SEQ ID NO 217
<211> LENGTH: 20
<212> TYPE: DNA
<213> ORGANISM: Artificial Sequence
<220> FEATURE:
<223> OTHER INFORMATION: Chemically synthesized

<400> SEQUENCE: 217
acaaagtaga gacctatcca                                           20
```

<210> SEQ ID NO 218
<211> LENGTH: 20
<212> TYPE: DNA
<213> ORGANISM: Artificial Sequence
<220> FEATURE:
<223> OTHER INFORMATION: Chemically synthesized

<400> SEQUENCE: 218
cacctggggt gggaaaagag                                               20

<210> SEQ ID NO 219
<211> LENGTH: 20
<212> TYPE: DNA
<213> ORGANISM: Artificial Sequence
<220> FEATURE:
<223> OTHER INFORMATION: Chemically synthesized

<400> SEQUENCE: 219
gagagggcag catggaatgg                                               20

<210> SEQ ID NO 220
<211> LENGTH: 20
<212> TYPE: DNA
<213> ORGANISM: Artificial Sequence
<220> FEATURE:
<223> OTHER INFORMATION: Chemically synthesized

<400> SEQUENCE: 220
cagtttgagc aggttgaggg                                               20

<210> SEQ ID NO 221
<211> LENGTH: 20
<212> TYPE: DNA
<213> ORGANISM: Artificial Sequence
<220> FEATURE:
<223> OTHER INFORMATION: Chemically synthesized

<400> SEQUENCE: 221
aaaggacact cagtctacct                                               20

<210> SEQ ID NO 222
<211> LENGTH: 20
<212> TYPE: DNA
<213> ORGANISM: Artificial Sequence
<220> FEATURE:
<223> OTHER INFORMATION: Chemically synthesized

<400> SEQUENCE: 222
ctgtgggcaa ggaacagatc                                               20

<210> SEQ ID NO 223
<211> LENGTH: 20
<212> TYPE: DNA
<213> ORGANISM: Artificial Sequence
<220> FEATURE:
<223> OTHER INFORMATION: Chemically synthesized

<400> SEQUENCE: 223
caaacagaat gccccgcacc                                               20

<210> SEQ ID NO 224
<211> LENGTH: 20
<212> TYPE: DNA
<213> ORGANISM: Artificial Sequence
<220> FEATURE:
<223> OTHER INFORMATION: Chemically synthesized

<400> SEQUENCE: 224
gtgaatagag ggtgccccat                                          20

<210> SEQ ID NO 225
<211> LENGTH: 20
<212> TYPE: DNA
<213> ORGANISM: Artificial Sequence
<220> FEATURE:
<223> OTHER INFORMATION: Chemically synthesized

<400> SEQUENCE: 225
tctcttgaga caatctggga                                          20

<210> SEQ ID NO 226
<211> LENGTH: 20
<212> TYPE: DNA
<213> ORGANISM: Artificial Sequence
<220> FEATURE:
<223> OTHER INFORMATION: Chemically synthesized

<400> SEQUENCE: 226
cctttgcttg acttcgactt                                          20

<210> SEQ ID NO 227
<211> LENGTH: 20
<212> TYPE: DNA
<213> ORGANISM: Artificial Sequence
<220> FEATURE:
<223> OTHER INFORMATION: Chemically synthesized

<400> SEQUENCE: 227
tgttatctca ctggacctga                                          20

<210> SEQ ID NO 228
<211> LENGTH: 20
<212> TYPE: DNA
<213> ORGANISM: Artificial Sequence
<220> FEATURE:
<223> OTHER INFORMATION: Chemically synthesized

<400> SEQUENCE: 228 cttttttag ggggtggtgg                                           20

<210> SEQ ID NO 229
<211> LENGTH: 20
<212> TYPE: DNA
<213> ORGANISM: Artificial Sequence
<220> FEATURE:
<223> OTHER INFORMATION: Chemically synthesized

<400> SEQUENCE: 229
ctctgatcca accaaagtgg                                          20

<210> SEQ ID NO 230
<211> LENGTH: 20
<212> TYPE: DNA
<213> ORGANISM: Artificial Sequence
<220> FEATURE:
<223> OTHER INFORMATION: Chemically synthesized

<400> SEQUENCE: 230
ggaacacagt agtagatgca                                          20

<210> SEQ ID NO 231
<211> LENGTH: 20

```
<212> TYPE: DNA
<213> ORGANISM: Artificial Sequence
<220> FEATURE:
<223> OTHER INFORMATION: Chemically synthesized

<400> SEQUENCE: 231
accagacacc tgagaagtaa                                               20

<210> SEQ ID NO 232
<211> LENGTH: 20
<212> TYPE: DNA
<213> ORGANISM: Artificial Sequence
<220> FEATURE:
<223> OTHER INFORMATION: Chemically synthesized

<400> SEQUENCE: 232
ctggtttgtg attgctacct                                               20

<210> SEQ ID NO 233
<211> LENGTH: 20
<212> TYPE: DNA
<213> ORGANISM: Artificial Sequence
<220> FEATURE:
<223> OTHER INFORMATION: Chemically synthesized

<400> SEQUENCE: 233
gtgcatcaaa caagggatct                                               20

<210> SEQ ID NO 234
<211> LENGTH: 20
<212> TYPE: DNA
<213> ORGANISM: Artificial Sequence
<220> FEATURE:
<223> OTHER INFORMATION: Chemically synthesized

<400> SEQUENCE: 234
ggcaactaac atatcctggg                                               20

<210> SEQ ID NO 235
<211> LENGTH: 20
<212> TYPE: DNA
<213> ORGANISM: Artificial Sequence
<220> FEATURE:
<223> OTHER INFORMATION: Chemically synthesized

<400> SEQUENCE: 235
acacagccac atgaaatctt                                               20

<210> SEQ ID NO 236
<211> LENGTH: 20
<212> TYPE: DNA
<213> ORGANISM: Artificial Sequence
<220> FEATURE:
<223> OTHER INFORMATION: Chemically synthesized

<400> SEQUENCE: 236
gcactctcca tctaccaaac                                               20

<210> SEQ ID NO 237
<211> LENGTH: 20
<212> TYPE: DNA
<213> ORGANISM: Artificial Sequence
<220> FEATURE:
<223> OTHER INFORMATION: Chemically synthesized

<400> SEQUENCE: 237
```
taagtgactg ggacaagtca        20

<210> SEQ ID NO 238
<211> LENGTH: 20
<212> TYPE: DNA
<213> ORGANISM: Artificial Sequence
<220> FEATURE:
<223> OTHER INFORMATION: Chemically synthesized

<400> SEQUENCE: 238
ggcaatcaaa tgtccacaga        20

<210> SEQ ID NO 239
<211> LENGTH: 20
<212> TYPE: DNA
<213> ORGANISM: Artificial Sequence
<220> FEATURE:
<223> OTHER INFORMATION: Chemically synthesized

<400> SEQUENCE: 239
cactctccaa aggtcacaat        20

<210> SEQ ID NO 240
<211> LENGTH: 20
<212> TYPE: DNA
<213> ORGANISM: Artificial Sequence
<220> FEATURE:
<223> OTHER INFORMATION: Chemically synthesized

<400> SEQUENCE: 240
atccagtgct acagcttaga        20

<210> SEQ ID NO 241
<211> LENGTH: 20
<212> TYPE: DNA
<213> ORGANISM: Artificial Sequence
<220> FEATURE:
<223> OTHER INFORMATION: Chemically synthesized

<400> SEQUENCE: 241
atcacctcct agtgctgtta        20

<210> SEQ ID NO 242
<211> LENGTH: 20
<212> TYPE: DNA
<213> ORGANISM: Artificial Sequence
<220> FEATURE:
<223> OTHER INFORMATION: Chemically synthesized

<400> SEQUENCE: 242
ccatcattct aagccccaag        20

<210> SEQ ID NO 243
<211> LENGTH: 20
<212> TYPE: DNA
<213> ORGANISM: Artificial Sequence
<220> FEATURE:
<223> OTHER INFORMATION: Chemically synthesized

<400> SEQUENCE: 243
ctgctatgac attccatccc        20

<210> SEQ ID NO 244
<211> LENGTH: 20
<212> TYPE: DNA
<213> ORGANISM: Artificial Sequence

```
<220> FEATURE:
<223> OTHER INFORMATION: Chemically synthesized

<400> SEQUENCE: 244
gatcacaaga gaagtctggc                                          20

<210> SEQ ID NO 245
<211> LENGTH: 20
<212> TYPE: DNA
<213> ORGANISM: Artificial Sequence
<220> FEATURE:
<223> OTHER INFORMATION: Chemically synthesized

<400> SEQUENCE: 245
gaacaccaga acagaactcc                                          20

<210> SEQ ID NO 246
<211> LENGTH: 20
<212> TYPE: DNA
<213> ORGANISM: Artificial Sequence
<220> FEATURE:
<223> OTHER INFORMATION: Chemically synthesized

<400> SEQUENCE: 246
cacagaattg tcccaaggat                                          20

<210> SEQ ID NO 247
<211> LENGTH: 20
<212> TYPE: DNA
<213> ORGANISM: Artificial Sequence
<220> FEATURE:
<223> OTHER INFORMATION: Chemically synthesized

<400> SEQUENCE: 247
aagctgagca actttaggtc                                          20

<210> SEQ ID NO 248
<211> LENGTH: 20
<212> TYPE: DNA
<213> ORGANISM: Artificial Sequence
<220> FEATURE:
<223> OTHER INFORMATION: Chemically synthesized

<400> SEQUENCE: 248
ttgcttgctc aaatctcact                                          20

<210> SEQ ID NO 249
<211> LENGTH: 20
<212> TYPE: DNA
<213> ORGANISM: Artificial Sequence
<220> FEATURE:
<223> OTHER INFORMATION: Chemically synthesized

<400> SEQUENCE: 249
tacagcctag ttagacaggg                                          20

<210> SEQ ID NO 250
<211> LENGTH: 20
<212> TYPE: DNA
<213> ORGANISM: Artificial Sequence
<220> FEATURE:
<223> OTHER INFORMATION: Chemically synthesized

<400> SEQUENCE: 250
gattccacct gtaaagaggc                                          20
```

<210> SEQ ID NO 251
<211> LENGTH: 20
<212> TYPE: DNA
<213> ORGANISM: Artificial Sequence
<220> FEATURE:
<223> OTHER INFORMATION: Chemically synthesized

<400> SEQUENCE: 251
cacagcagaa catctcacaa                                               20

<210> SEQ ID NO 252
<211> LENGTH: 20
<212> TYPE: DNA
<213> ORGANISM: Artificial Sequence
<220> FEATURE:
<223> OTHER INFORMATION: Chemically synthesized

<400> SEQUENCE: 252
gagaagagaa acgctgtcac                                               20

<210> SEQ ID NO 253
<211> LENGTH: 20
<212> TYPE: DNA
<213> ORGANISM: Artificial Sequence
<220> FEATURE:
<223> OTHER INFORMATION: Chemically synthesized

<400> SEQUENCE: 253
tctggcacta tatctccgag                                               20

<210> SEQ ID NO 254
<211> LENGTH: 20
<212> TYPE: DNA
<213> ORGANISM: Artificial Sequence
<220> FEATURE:
<223> OTHER INFORMATION: Chemically synthesized

<400> SEQUENCE: 254
taggtcccca aactgagtag                                               20

<210> SEQ ID NO 255
<211> LENGTH: 20
<212> TYPE: DNA
<213> ORGANISM: Artificial Sequence
<220> FEATURE:
<223> OTHER INFORMATION: Chemically synthesized

<400> SEQUENCE: 255
agagactcag agaaaggagg                                               20

<210> SEQ ID NO 256
<211> LENGTH: 20
<212> TYPE: DNA
<213> ORGANISM: Artificial Sequence
<220> FEATURE:
<223> OTHER INFORMATION: Chemically synthesized

<400> SEQUENCE: 256
tgtgacgata ctggacagat                                               20

<210> SEQ ID NO 257
<211> LENGTH: 20
<212> TYPE: DNA
<213> ORGANISM: Artificial Sequence
<220> FEATURE:
<223> OTHER INFORMATION: Chemically synthesized

```
<400> SEQUENCE: 257
ccaaagaaca gtctcctccc                                              20

<210> SEQ ID NO 258
<211> LENGTH: 20
<212> TYPE: DNA
<213> ORGANISM: Artificial Sequence
<220> FEATURE:
<223> OTHER INFORMATION: Chemically synthesized

<400> SEQUENCE: 258
ttgaagggag gataagaggc                                              20

<210> SEQ ID NO 259
<211> LENGTH: 20
<212> TYPE: DNA
<213> ORGANISM: Artificial Sequence
<220> FEATURE:
<223> OTHER INFORMATION: Chemically synthesized

<400> SEQUENCE: 259
ctcctaacag ccgggaattt                                              20

<210> SEQ ID NO 260
<211> LENGTH: 20
<212> TYPE: DNA
<213> ORGANISM: Artificial Sequence
<220> FEATURE:
<223> OTHER INFORMATION: Chemically synthesized

<400> SEQUENCE: 260
ttaaagtcac aacatccgcg                                              20

<210> SEQ ID NO 261
<211> LENGTH: 20
<212> TYPE: DNA
<213> ORGANISM: Artificial Sequence
<220> FEATURE:
<223> OTHER INFORMATION: Chemically synthesized

<400> SEQUENCE: 261
tcgttacttc ggagttacga                                              20

<210> SEQ ID NO 262
<211> LENGTH: 20
<212> TYPE: DNA
<213> ORGANISM: Artificial Sequence
<220> FEATURE:
<223> OTHER INFORMATION: Chemically synthesized

<400> SEQUENCE: 262
tcgctatcat tgccatcctc                                              20

<210> SEQ ID NO 263
<211> LENGTH: 20
<212> TYPE: DNA
<213> ORGANISM: Artificial Sequence
<220> FEATURE:
<223> OTHER INFORMATION: Chemically synthesized

<400> SEQUENCE: 263
ctgtgagagc aatgacagtc                                              20

<210> SEQ ID NO 264
```

<211> LENGTH: 20
<212> TYPE: DNA
<213> ORGANISM: Artificial Sequence
<220> FEATURE:
<223> OTHER INFORMATION: Chemically synthesized

<400> SEQUENCE: 264
atgaaacaag cgagtgtacc                                            20

<210> SEQ ID NO 265
<211> LENGTH: 20
<212> TYPE: DNA
<213> ORGANISM: Artificial Sequence
<220> FEATURE:
<223> OTHER INFORMATION: Chemically synthesized

<400> SEQUENCE: 265
caaaaggcac agtcctaacg                                            20

<210> SEQ ID NO 266
<211> LENGTH: 20
<212> TYPE: DNA
<213> ORGANISM: Artificial Sequence
<220> FEATURE:
<223> OTHER INFORMATION: Chemically synthesized

<400> SEQUENCE: 266
aaatagcact ggcttgtcaa                                            20

<210> SEQ ID NO 267
<211> LENGTH: 20
<212> TYPE: DNA
<213> ORGANISM: Artificial Sequence
<220> FEATURE:
<223> OTHER INFORMATION: Chemically synthesized

<400> SEQUENCE: 267
tttaaactca caccgaaggg                                            20

<210> SEQ ID NO 268
<211> LENGTH: 20
<212> TYPE: DNA
<213> ORGANISM: Artificial Sequence
<220> FEATURE:
<223> OTHER INFORMATION: Chemically synthesized

<400> SEQUENCE: 268
tgtttccact agcccttaag                                            20

<210> SEQ ID NO 269
<211> LENGTH: 20
<212> TYPE: DNA
<213> ORGANISM: Artificial Sequence
<220> FEATURE:
<223> OTHER INFORMATION: Chemically synthesized

<400> SEQUENCE: 269
aacctgagaa ctgtgaaagg                                            20

<210> SEQ ID NO 270
<211> LENGTH: 20
<212> TYPE: DNA
<213> ORGANISM: Artificial Sequence
<220> FEATURE:
<223> OTHER INFORMATION: Chemically synthesized

<400> SEQUENCE: 270
cctcccttaa ttcaagcctt                                              20

<210> SEQ ID NO 271
<211> LENGTH: 20
<212> TYPE: DNA
<213> ORGANISM: Artificial Sequence
<220> FEATURE:
<223> OTHER INFORMATION: Chemically synthesized

<400> SEQUENCE: 271
ttcgaatcgc cataccaaaa                                              20

<210> SEQ ID NO 272
<211> LENGTH: 20
<212> TYPE: DNA
<213> ORGANISM: Artificial Sequence
<220> FEATURE:
<223> OTHER INFORMATION: Chemically synthesized

<400> SEQUENCE: 272
tacattagtg gagaaagcgt                                              20

<210> SEQ ID NO 273
<211> LENGTH: 20
<212> TYPE: DNA
<213> ORGANISM: Artificial Sequence
<220> FEATURE:
<223> OTHER INFORMATION: Chemically synthesized

<400> SEQUENCE: 273
ctaaagtcag cacaacccac                                              20

<210> SEQ ID NO 274
<211> LENGTH: 20
<212> TYPE: DNA
<213> ORGANISM: Artificial Sequence
<220> FEATURE:
<223> OTHER INFORMATION: Chemically synthesized

<400> SEQUENCE: 274
gagaagcaag ggcaaaacag                                              20

<210> SEQ ID NO 275
<211> LENGTH: 20
<212> TYPE: DNA
<213> ORGANISM: Artificial Sequence
<220> FEATURE:
<223> OTHER INFORMATION: Chemically synthesized

<400> SEQUENCE: 275
caaacgttct tcagatcaca                                              20

<210> SEQ ID NO 276
<211> LENGTH: 20
<212> TYPE: DNA
<213> ORGANISM: Artificial Sequence
<220> FEATURE:
<223> OTHER INFORMATION: Chemically synthesized

<400> SEQUENCE: 276
ggccaactga ggtagaagat                                              20

<210> SEQ ID NO 277
<211> LENGTH: 20
<212> TYPE: DNA

```
<213> ORGANISM: Artificial Sequence
<220> FEATURE:
<223> OTHER INFORMATION: Chemically synthesized

<400> SEQUENCE: 277
cactaccccc agtttctcaa                                              20

<210> SEQ ID NO 278
<211> LENGTH: 20
<212> TYPE: DNA
<213> ORGANISM: Artificial Sequence
<220> FEATURE:
<223> OTHER INFORMATION: Chemically synthesized

<400> SEQUENCE: 278
tattactggc agtgtcctct                                              20

<210> SEQ ID NO 279
<211> LENGTH: 20
<212> TYPE: DNA
<213> ORGANISM: Artificial Sequence
<220> FEATURE:
<223> OTHER INFORMATION: Chemically synthesized

<400> SEQUENCE: 279
gaggctcagt tagaggctct                                              20

<210> SEQ ID NO 280
<211> LENGTH: 20
<212> TYPE: DNA
<213> ORGANISM: Artificial Sequence
<220> FEATURE:
<223> OTHER INFORMATION: Chemically synthesized

<400> SEQUENCE: 280
caatgctcct ttcctaggac                                              20

<210> SEQ ID NO 281
<211> LENGTH: 20
<212> TYPE: DNA
<213> ORGANISM: Artificial Sequence
<220> FEATURE:
<223> OTHER INFORMATION: Chemically synthesized

<400> SEQUENCE: 281
acactgaatt cttgtcgctc                                              20

<210> SEQ ID NO 282
<211> LENGTH: 20
<212> TYPE: DNA
<213> ORGANISM: Artificial Sequence
<220> FEATURE:
<223> OTHER INFORMATION: Chemically synthesized

<400> SEQUENCE: 282
aaggtcagac actgaagtct                                              20

<210> SEQ ID NO 283
<211> LENGTH: 20
<212> TYPE: DNA
<213> ORGANISM: Artificial Sequence
<220> FEATURE:
<223> OTHER INFORMATION: Chemically synthesized

<400> SEQUENCE: 283
ccgacctcta agtggttcag                                              20
```

<210> SEQ ID NO 284
<211> LENGTH: 20
<212> TYPE: DNA
<213> ORGANISM: Artificial Sequence
<220> FEATURE:
<223> OTHER INFORMATION: Chemically synthesized

<400> SEQUENCE: 284
gcatccatct gggtttctaa                                              20

<210> SEQ ID NO 285
<211> LENGTH: 20
<212> TYPE: DNA
<213> ORGANISM: Artificial Sequence
<220> FEATURE:
<223> OTHER INFORMATION: Chemically synthesized

<400> SEQUENCE: 285
ggagtctgag actgacacat                                              20

<210> SEQ ID NO 286
<211> LENGTH: 20
<212> TYPE: DNA
<213> ORGANISM: Artificial Sequence
<220> FEATURE:
<223> OTHER INFORMATION: Chemically synthesized

<400> SEQUENCE: 286
cgtgtggaag atacactgtc                                              20

<210> SEQ ID NO 287
<211> LENGTH: 20
<212> TYPE: DNA
<213> ORGANISM: Artificial Sequence
<220> FEATURE:
<223> OTHER INFORMATION: Chemically synthesized

<400> SEQUENCE: 287
gcctatagtc tgctgctttc                                              20

<210> SEQ ID NO 288
<211> LENGTH: 20
<212> TYPE: DNA
<213> ORGANISM: Artificial Sequence
<220> FEATURE:
<223> OTHER INFORMATION: Chemically synthesized

<400> SEQUENCE: 288
caagcatcgg agcacacata                                              20

<210> SEQ ID NO 289
<211> LENGTH: 20
<212> TYPE: DNA
<213> ORGANISM: Artificial Sequence
<220> FEATURE:
<223> OTHER INFORMATION: Chemically synthesized

<400> SEQUENCE: 289
gagtcacact ggttttcagg                                              20

<210> SEQ ID NO 290
<211> LENGTH: 20
<212> TYPE: DNA
<213> ORGANISM: Artificial Sequence
<220> FEATURE:

<223> OTHER INFORMATION: Chemically synthesized

<400> SEQUENCE: 290
cttctctgat aagccgtgac                                          20

<210> SEQ ID NO 291
<211> LENGTH: 20
<212> TYPE: DNA
<213> ORGANISM: Artificial Sequence
<220> FEATURE:
<223> OTHER INFORMATION: Chemically synthesized

<400> SEQUENCE: 291
gagaggacag ctggtaactg                                          20

<210> SEQ ID NO 292
<211> LENGTH: 20
<212> TYPE: DNA
<213> ORGANISM: Artificial Sequence
<220> FEATURE:
<223> OTHER INFORMATION: Chemically synthesized

<400> SEQUENCE: 292
ttttgaacac attggggtcc                                          20

<210> SEQ ID NO 293
<211> LENGTH: 20
<212> TYPE: DNA
<213> ORGANISM: Artificial Sequence
<220> FEATURE:
<223> OTHER INFORMATION: Chemically synthesized

<400> SEQUENCE: 293
gtgccactac tgaaaggatg                                          20

<210> SEQ ID NO 294
<211> LENGTH: 20
<212> TYPE: DNA
<213> ORGANISM: Artificial Sequence
<220> FEATURE:
<223> OTHER INFORMATION: Chemically synthesized

<400> SEQUENCE: 294
gactgctctg actcttcacc                                          20

<210> SEQ ID NO 295
<211> LENGTH: 20
<212> TYPE: DNA
<213> ORGANISM: Artificial Sequence
<220> FEATURE:
<223> OTHER INFORMATION: Chemically synthesized

<400> SEQUENCE: 295
ggtacgcact tatgaggaac                                          20

<210> SEQ ID NO 296
<211> LENGTH: 20
<212> TYPE: DNA
<213> ORGANISM: Artificial Sequence
<220> FEATURE:
<223> OTHER INFORMATION: Chemically synthesized

<400> SEQUENCE: 296
tctctgctgc tacatctcag                                          20

```
<210> SEQ ID NO 297
<211> LENGTH: 20
<212> TYPE: DNA
<213> ORGANISM: Artificial Sequence
<220> FEATURE:
<223> OTHER INFORMATION: Chemically synthesized

<400> SEQUENCE: 297
catgagaagg gagacggatg                                              20

<210> SEQ ID NO 298
<211> LENGTH: 20
<212> TYPE: DNA
<213> ORGANISM: Artificial Sequence
<220> FEATURE:
<223> OTHER INFORMATION: Chemically synthesized

<400> SEQUENCE: 298
atcccagaca ataagagggg                                              20

<210> SEQ ID NO 299
<211> LENGTH: 20
<212> TYPE: DNA
<213> ORGANISM: Artificial Sequence
<220> FEATURE:
<223> OTHER INFORMATION: Chemically synthesized

<400> SEQUENCE: 299
cgaggataga gaagccagag                                              20

<210> SEQ ID NO 300
<211> LENGTH: 20
<212> TYPE: DNA
<213> ORGANISM: Artificial Sequence
<220> FEATURE:
<223> OTHER INFORMATION: Chemically synthesized

<400> SEQUENCE: 300
cccacttttg ggaacaatga                                              20

<210> SEQ ID NO 301
<211> LENGTH: 20
<212> TYPE: DNA
<213> ORGANISM: Artificial Sequence
<220> FEATURE:
<223> OTHER INFORMATION: Chemically synthesized

<400> SEQUENCE: 301
gctgcgtttg tgatttgtta                                              20

<210> SEQ ID NO 302
<211> LENGTH: 20
<212> TYPE: DNA
<213> ORGANISM: Artificial Sequence
<220> FEATURE:
<223> OTHER INFORMATION: Chemically synthesized

<400> SEQUENCE: 302
ggatgaaagc agaggtcaag                                              20

<210> SEQ ID NO 303
<211> LENGTH: 20
<212> TYPE: DNA
<213> ORGANISM: Artificial Sequence
<220> FEATURE:
<223> OTHER INFORMATION: Chemically synthesized
```

<400> SEQUENCE: 303
ggatgaaagc agaggtcaag						20

<210> SEQ ID NO 304
<211> LENGTH: 20
<212> TYPE: DNA
<213> ORGANISM: Artificial Sequence
<220> FEATURE:
<223> OTHER INFORMATION: Chemically synthesized

<400> SEQUENCE: 304
taagtgggtc aaggtcagag						20

<210> SEQ ID NO 305
<211> LENGTH: 20
<212> TYPE: DNA
<213> ORGANISM: Artificial Sequence
<220> FEATURE:
<223> OTHER INFORMATION: Chemically synthesized

<400> SEQUENCE: 305
gattgtggag ctgactgaag						20

<210> SEQ ID NO 306
<211> LENGTH: 20
<212> TYPE: DNA
<213> ORGANISM: Artificial Sequence
<220> FEATURE:
<223> OTHER INFORMATION: Chemically synthesized

<400> SEQUENCE: 306
catcttatcg ctgaagggga						20

<210> SEQ ID NO 307
<211> LENGTH: 20
<212> TYPE: DNA
<213> ORGANISM: Artificial Sequence
<220> FEATURE:
<223> OTHER INFORMATION: Chemically synthesized

<400> SEQUENCE: 307
ctgcacaatc tgggagagac						20

<210> SEQ ID NO 308
<211> LENGTH: 20
<212> TYPE: DNA
<213> ORGANISM: Artificial Sequence
<220> FEATURE:
<223> OTHER INFORMATION: Chemically synthesized

<400> SEQUENCE: 308
gagttaggct ggaggaacag						20

<210> SEQ ID NO 309
<211> LENGTH: 20
<212> TYPE: DNA
<213> ORGANISM: Artificial Sequence
<220> FEATURE:
<223> OTHER INFORMATION: Chemically synthesized

<400> SEQUENCE: 309
tggtaagata gctgcgtcta						20

<210> SEQ ID NO 310
<211> LENGTH: 20

```
<212> TYPE: DNA
<213> ORGANISM: Artificial Sequence
<220> FEATURE:
<223> OTHER INFORMATION: Chemically synthesized

<400> SEQUENCE: 310
actgaagaca catcaccta                                           20

<210> SEQ ID NO 311
<211> LENGTH: 20
<212> TYPE: DNA
<213> ORGANISM: Artificial Sequence
<220> FEATURE:
<223> OTHER INFORMATION: Chemically synthesized

<400> SEQUENCE: 311
tccaagaaaa aactgaaggg                                          20

<210> SEQ ID NO 312
<211> LENGTH: 20
<212> TYPE: DNA
<213> ORGANISM: Artificial Sequence
<220> FEATURE:
<223> OTHER INFORMATION: Chemically synthesized

<400> SEQUENCE: 312
agagaatatg acccagaagc                                          20

<210> SEQ ID NO 313
<211> LENGTH: 20
<212> TYPE: DNA
<213> ORGANISM: Artificial Sequence
<220> FEATURE:
<223> OTHER INFORMATION: Chemically synthesized

<400> SEQUENCE: 313 tcaataccte aggttgtcct                                          20

<210> SEQ ID NO 314
<211> LENGTH: 20
<212> TYPE: DNA
<213> ORGANISM: Artificial Sequence
<220> FEATURE:
<223> OTHER INFORMATION: Chemically synthesized

<400> SEQUENCE: 314
gtccacactt gagaagctaa                                          20

<210> SEQ ID NO 315
<211> LENGTH: 20
<212> TYPE: DNA
<213> ORGANISM: Artificial Sequence
<220> FEATURE:
<223> OTHER INFORMATION: Chemically synthesized

<400> SEQUENCE: 315
cactattttt ctgcccccta                                          20

<210> SEQ ID NO 316
<211> LENGTH: 20
<212> TYPE: DNA
<213> ORGANISM: Artificial Sequence
<220> FEATURE:
<223> OTHER INFORMATION: Chemically synthesized

<400> SEQUENCE: 316
```
gcaagttctt acgccatcta                                              20

<210> SEQ ID NO 317
<211> LENGTH: 20
<212> TYPE: DNA
<213> ORGANISM: Artificial Sequence
<220> FEATURE:
<223> OTHER INFORMATION: Chemically synthesized

<400> SEQUENCE: 317
gtgcctcagg cacattatac                                              20

<210> SEQ ID NO 318
<211> LENGTH: 20
<212> TYPE: DNA
<213> ORGANISM: Artificial Sequence
<220> FEATURE:
<223> OTHER INFORMATION: Chemically synthesized

<400> SEQUENCE: 318
aggagactct gaactatgcc                                              20

<210> SEQ ID NO 319
<211> LENGTH: 20
<212> TYPE: DNA
<213> ORGANISM: Artificial Sequence
<220> FEATURE:
<223> OTHER INFORMATION: Chemically synthesized

<400> SEQUENCE: 319
ttaagtgctc aataacccccc                                             20

<210> SEQ ID NO 320
<211> LENGTH: 20
<212> TYPE: DNA
<213> ORGANISM: Artificial Sequence
<220> FEATURE:
<223> OTHER INFORMATION: Chemically synthesized

<400> SEQUENCE: 320
tcaagtcagg ccattcaatt                                              20

<210> SEQ ID NO 321
<211> LENGTH: 20
<212> TYPE: DNA
<213> ORGANISM: Artificial Sequence
<220> FEATURE:
<223> OTHER INFORMATION: Chemically synthesized

<400> SEQUENCE: 321
ctccattttc ggcttcttca                                              20

<210> SEQ ID NO 322
<211> LENGTH: 20
<212> TYPE: DNA
<213> ORGANISM: Artificial Sequence
<220> FEATURE:
<223> OTHER INFORMATION: Chemically synthesized

<400> SEQUENCE: 322
gaggaaaagc tcgtggtcag                                              20

<210> SEQ ID NO 323
<211> LENGTH: 20
<212> TYPE: DNA
<213> ORGANISM: Artificial Sequence

```
<220> FEATURE:
<223> OTHER INFORMATION: Chemically synthesized

<400> SEQUENCE: 323
gatctgtgtt ggcttctcaa                                              20

<210> SEQ ID NO 324
<211> LENGTH: 20
<212> TYPE: DNA
<213> ORGANISM: Artificial Sequence
<220> FEATURE:
<223> OTHER INFORMATION: Chemically synthesized

<400> SEQUENCE: 324
gagattccga gttcgaagaa                                              20

<210> SEQ ID NO 325
<211> LENGTH: 20
<212> TYPE: DNA
<213> ORGANISM: Artificial Sequence
<220> FEATURE:
<223> OTHER INFORMATION: Chemically synthesized

<400> SEQUENCE: 325
tgtgcaaaaa tattggtgct                                              20

<210> SEQ ID NO 326
<211> LENGTH: 20
<212> TYPE: DNA
<213> ORGANISM: Artificial Sequence
<220> FEATURE:
<223> OTHER INFORMATION: Chemically synthesized

<400> SEQUENCE: 326
tctggagttt cgatgagaca                                              20

<210> SEQ ID NO 327
<211> LENGTH: 20
<212> TYPE: DNA
<213> ORGANISM: Artificial Sequence
<220> FEATURE:
<223> OTHER INFORMATION: Chemically synthesized

<400> SEQUENCE: 327
tgagattctt gctctccttt                                              20

<210> SEQ ID NO 328
<211> LENGTH: 20
<212> TYPE: DNA
<213> ORGANISM: Artificial Sequence
<220> FEATURE:
<223> OTHER INFORMATION: Chemically synthesized

<400> SEQUENCE: 328
ctgcaaatga gctgacaagc                                              20

<210> SEQ ID NO 329
<211> LENGTH: 20
<212> TYPE: DNA
<213> ORGANISM: Artificial Sequence
<220> FEATURE:
<223> OTHER INFORMATION: Chemically synthesized

<400> SEQUENCE: 329
tggaagaaac cagtaaacgt                                              20
```

<210> SEQ ID NO 330
<211> LENGTH: 20
<212> TYPE: DNA
<213> ORGANISM: Artificial Sequence
<220> FEATURE:
<223> OTHER INFORMATION: Chemically synthesized

<400> SEQUENCE: 330
aagagtgaac tgcaacgtag                                               20

<210> SEQ ID NO 331
<211> LENGTH: 20
<212> TYPE: DNA
<213> ORGANISM: Artificial Sequence
<220> FEATURE:
<223> OTHER INFORMATION: Chemically synthesized

<400> SEQUENCE: 331
gcaataggag ccgtagattt                                               20

<210> SEQ ID NO 332
<211> LENGTH: 20
<212> TYPE: DNA
<213> ORGANISM: Artificial Sequence
<220> FEATURE:
<223> OTHER INFORMATION: Chemically synthesized

<400> SEQUENCE: 332
atttctagtg gcaagaggtt                                               20

<210> SEQ ID NO 333
<211> LENGTH: 20
<212> TYPE: DNA
<213> ORGANISM: Artificial Sequence
<220> FEATURE:
<223> OTHER INFORMATION: Chemically synthesized

<400> SEQUENCE: 333
taactgaacc aggcttgttt                                               20

<210> SEQ ID NO 334
<211> LENGTH: 20
<212> TYPE: DNA
<213> ORGANISM: Artificial Sequence
<220> FEATURE:
<223> OTHER INFORMATION: Chemically synthesized

<400> SEQUENCE: 334
acagcaatag tttgagtagg                                               20

<210> SEQ ID NO 335
<211> LENGTH: 20
<212> TYPE: DNA
<213> ORGANISM: Artificial Sequence
<220> FEATURE:
<223> OTHER INFORMATION: Chemically synthesized

<400> SEQUENCE: 335
tgttgccttg tattgttgtt                                               20

<210> SEQ ID NO 336
<211> LENGTH: 20
<212> TYPE: DNA
<213> ORGANISM: Artificial Sequence
<220> FEATURE:
<223> OTHER INFORMATION: Chemically synthesized

<400> SEQUENCE: 336
caggtcatct cttgcttcag                                              20

<210> SEQ ID NO 337
<211> LENGTH: 20
<212> TYPE: DNA
<213> ORGANISM: Artificial Sequence
<220> FEATURE:
<223> OTHER INFORMATION: Chemically synthesized

<400> SEQUENCE: 337
tcagagtaca ccaagggcaa                                              20

<210> SEQ ID NO 338
<211> LENGTH: 20
<212> TYPE: DNA
<213> ORGANISM: Artificial Sequence
<220> FEATURE:
<223> OTHER INFORMATION: Chemically synthesized

<400> SEQUENCE: 338
aaactataaa gtttgcggca                                              20

<210> SEQ ID NO 339
<211> LENGTH: 20
<212> TYPE: DNA
<213> ORGANISM: Artificial Sequence
<220> FEATURE:
<223> OTHER INFORMATION: Chemically synthesized

<400> SEQUENCE: 339
tggcagagtt taagatgctt                                              20

<210> SEQ ID NO 340
<211> LENGTH: 20
<212> TYPE: DNA
<213> ORGANISM: Artificial Sequence
<220> FEATURE:
<223> OTHER INFORMATION: Chemically synthesized

<400> SEQUENCE: 340
cctagcacct tttggatgat                                              20

<210> SEQ ID NO 341
<211> LENGTH: 20
<212> TYPE: DNA
<213> ORGANISM: Artificial Sequence
<220> FEATURE:
<223> OTHER INFORMATION: Chemically synthesized

<400> SEQUENCE: 341
ggagccatca taacactcat                                              20

<210> SEQ ID NO 342
<211> LENGTH: 20
<212> TYPE: DNA
<213> ORGANISM: Artificial Sequence
<220> FEATURE:
<223> OTHER INFORMATION: Chemically synthesized

<400> SEQUENCE: 342
tatcctgagg atttcctgca                                              20

<210> SEQ ID NO 343

```
<211> LENGTH: 20
<212> TYPE: DNA
<213> ORGANISM: Artificial Sequence
<220> FEATURE:
<223> OTHER INFORMATION: Chemically synthesized

<400> SEQUENCE: 343
tgcgactaaa agcaaatcca                                               20

<210> SEQ ID NO 344
<211> LENGTH: 20
<212> TYPE: DNA
<213> ORGANISM: Artificial Sequence
<220> FEATURE:
<223> OTHER INFORMATION: Chemically synthesized

<400> SEQUENCE: 344
ggtgttctct taactggtcc                                               20

<210> SEQ ID NO 345
<211> LENGTH: 20
<212> TYPE: DNA
<213> ORGANISM: Artificial Sequence
<220> FEATURE:
<223> OTHER INFORMATION: Chemically synthesized

<400> SEQUENCE: 345
gcctgcacac aagaatatgt                                               20

<210> SEQ ID NO 346
<211> LENGTH: 20
<212> TYPE: DNA
<213> ORGANISM: Artificial Sequence
<220> FEATURE:
<223> OTHER INFORMATION: Chemically synthesized

<400> SEQUENCE: 346
catgcttgct tttgttcgtt                                               20

<210> SEQ ID NO 347
<211> LENGTH: 20
<212> TYPE: DNA
<213> ORGANISM: Artificial Sequence
<220> FEATURE:
<223> OTHER INFORMATION: Chemically synthesized

<400> SEQUENCE: 347
ctttgctgtt ctacttcccc                                               20

<210> SEQ ID NO 348
<211> LENGTH: 20
<212> TYPE: DNA
<213> ORGANISM: Artificial Sequence
<220> FEATURE:
<223> OTHER INFORMATION: Chemically synthesized

<400> SEQUENCE: 348
aaatacagac gattgtggcc                                               20

<210> SEQ ID NO 349
<211> LENGTH: 20
<212> TYPE: DNA
<213> ORGANISM: Artificial Sequence
<220> FEATURE:
<223> OTHER INFORMATION: Chemically synthesized

<400> SEQUENCE: 349
```
agaggtaagc aggtatcact                                              20

<210> SEQ ID NO 350
<211> LENGTH: 20
<212> TYPE: DNA
<213> ORGANISM: Artificial Sequence
<220> FEATURE:
<223> OTHER INFORMATION: Chemically synthesized

<400> SEQUENCE: 350
gacatggaga ttccagagtt                                              20

<210> SEQ ID NO 351
<211> LENGTH: 20
<212> TYPE: DNA
<213> ORGANISM: Artificial Sequence
<220> FEATURE:
<223> OTHER INFORMATION: Chemically synthesized

<400> SEQUENCE: 351
cagcaataaa cccatgcttc                                              20

<210> SEQ ID NO 352
<211> LENGTH: 20
<212> TYPE: DNA
<213> ORGANISM: Artificial Sequence
<220> FEATURE:
<223> OTHER INFORMATION: Chemically synthesized

<400> SEQUENCE: 352
caggcatgat tcatttgatt                                              20

<210> SEQ ID NO 353
<211> LENGTH: 20
<212> TYPE: DNA
<213> ORGANISM: Artificial Sequence
<220> FEATURE:
<223> OTHER INFORMATION: Chemically synthesized

<400> SEQUENCE: 353
tgaagcatga agtttcgaca                                              20

<210> SEQ ID NO 354
<211> LENGTH: 20
<212> TYPE: DNA
<213> ORGANISM: Artificial Sequence
<220> FEATURE:
<223> OTHER INFORMATION: Chemically synthesized

<400> SEQUENCE: 354
aaagtcatgc atgctgacta                                              20

<210> SEQ ID NO 355
<211> LENGTH: 20
<212> TYPE: DNA
<213> ORGANISM: Artificial Sequence
<220> FEATURE:
<223> OTHER INFORMATION: Chemically synthesized

<400> SEQUENCE: 355
catttcacgg agcttggtaa                                              20

<210> SEQ ID NO 356
<211> LENGTH: 20
<212> TYPE: DNA

```
<213> ORGANISM: Artificial Sequence
<220> FEATURE:
<223> OTHER INFORMATION: Chemically synthesized

<400> SEQUENCE: 356
tatttcttcg tttgcagggg                                               20

<210> SEQ ID NO 357
<211> LENGTH: 20
<212> TYPE: DNA
<213> ORGANISM: Artificial Sequence
<220> FEATURE:
<223> OTHER INFORMATION: Chemically synthesized

<400> SEQUENCE: 357
ccatttgctg tcccattttg                                               20

<210> SEQ ID NO 358
<211> LENGTH: 20
<212> TYPE: DNA
<213> ORGANISM: Artificial Sequence
<220> FEATURE:
<223> OTHER INFORMATION: Chemically synthesized

<400> SEQUENCE: 358
ctgttttgaa acccctgaga                                               20

<210> SEQ ID NO 359
<211> LENGTH: 20
<212> TYPE: DNA
<213> ORGANISM: Artificial Sequence
<220> FEATURE:
<223> OTHER INFORMATION: Chemically synthesized

<400> SEQUENCE: 359
acatggggtt agagcttttc                                               20

<210> SEQ ID NO 360
<211> LENGTH: 20
<212> TYPE: DNA
<213> ORGANISM: Artificial Sequence
<220> FEATURE:
<223> OTHER INFORMATION: Chemically synthesized

<400> SEQUENCE: 360
agaggatgaa ttccctaaaa                                               20

<210> SEQ ID NO 361
<211> LENGTH: 20
<212> TYPE: DNA
<213> ORGANISM: Artificial Sequence
<220> FEATURE:
<223> OTHER INFORMATION: Chemically synthesized

<400> SEQUENCE: 361
tgaagtagaa ccctgataca                                               20

<210> SEQ ID NO 362
<211> LENGTH: 20
<212> TYPE: DNA
<213> ORGANISM: Artificial Sequence
<220> FEATURE:
<223> OTHER INFORMATION: Chemically synthesized

<400> SEQUENCE: 362
cctccccaag aaaatgtctc                                               20
```

<210> SEQ ID NO 363
<211> LENGTH: 20
<212> TYPE: DNA
<213> ORGANISM: Artificial Sequence
<220> FEATURE:
<223> OTHER INFORMATION: Chemically synthesized

<400> SEQUENCE: 363
aggatcaaag tttgactgca                                              20

<210> SEQ ID NO 364
<211> LENGTH: 20
<212> TYPE: DNA
<213> ORGANISM: Artificial Sequence
<220> FEATURE:
<223> OTHER INFORMATION: Chemically synthesized

<400> SEQUENCE: 364
gggtgagcaa tgcactaaaa                                              20

<210> SEQ ID NO 365
<211> LENGTH: 20
<212> TYPE: DNA
<213> ORGANISM: Artificial Sequence
<220> FEATURE:
<223> OTHER INFORMATION: Chemically synthesized

<400> SEQUENCE: 365
acagcttaat tttccgtgtg                                              20

<210> SEQ ID NO 366
<211> LENGTH: 20
<212> TYPE: DNA
<213> ORGANISM: Artificial Sequence
<220> FEATURE:
<223> OTHER INFORMATION: Chemically synthesized

<400> SEQUENCE: 366
caaatgcgtt ctttccttgg                                              20

<210> SEQ ID NO 367
<211> LENGTH: 20
<212> TYPE: DNA
<213> ORGANISM: Artificial Sequence
<220> FEATURE:
<223> OTHER INFORMATION: Chemically synthesized

<400> SEQUENCE: 367
ttctcccctt ataagtgaca                                              20

<210> SEQ ID NO 368
<211> LENGTH: 20
<212> TYPE: DNA
<213> ORGANISM: Artificial Sequence
<220> FEATURE:
<223> OTHER INFORMATION: Chemically synthesized

<400> SEQUENCE: 368
agtcagctta tctctattgg                                              20

<210> SEQ ID NO 369
<211> LENGTH: 20
<212> TYPE: DNA
<213> ORGANISM: Artificial Sequence
<220> FEATURE:

<223> OTHER INFORMATION: Chemically synthesized

<400> SEQUENCE: 369
acacatataa cacagggcaa                                                 20

<210> SEQ ID NO 370
<211> LENGTH: 20
<212> TYPE: DNA
<213> ORGANISM: Artificial Sequence
<220> FEATURE:
<223> OTHER INFORMATION: Chemically synthesized

<400> SEQUENCE: 370
caactgcaaa tatgtgcgtg                                                 20

<210> SEQ ID NO 371
<211> LENGTH: 20
<212> TYPE: DNA
<213> ORGANISM: Artificial Sequence
<220> FEATURE:
<223> OTHER INFORMATION: Chemically synthesized

<400> SEQUENCE: 371
tgcttgttaa tgtgccagta                                                 20

<210> SEQ ID NO 372
<211> LENGTH: 20
<212> TYPE: DNA
<213> ORGANISM: Artificial Sequence
<220> FEATURE:
<223> OTHER INFORMATION: Chemically synthesized

<400> SEQUENCE: 372
cggagttgga ataaaaacct                                                 20

<210> SEQ ID NO 373
<211> LENGTH: 20
<212> TYPE: DNA
<213> ORGANISM: Artificial Sequence
<220> FEATURE:
<223> OTHER INFORMATION: Chemically synthesized

<400> SEQUENCE: 373
gatgttactc aaccacagtg                                                 20

<210> SEQ ID NO 374
<211> LENGTH: 20
<212> TYPE: DNA
<213> ORGANISM: Artificial Sequence
<220> FEATURE:
<223> OTHER INFORMATION: Chemically synthesized

<400> SEQUENCE: 374
acacatctta aagaccagtc                                                 20

<210> SEQ ID NO 375
<211> LENGTH: 20
<212> TYPE: DNA
<213> ORGANISM: Artificial Sequence
<220> FEATURE:
<223> OTHER INFORMATION: Chemically synthesized

<400> SEQUENCE: 375
tcgttaaata gcctcacagt                                                 20

```
<210> SEQ ID NO 376
<211> LENGTH: 20
<212> TYPE: DNA
<213> ORGANISM: Artificial Sequence
<220> FEATURE:
<223> OTHER INFORMATION: Chemically synthesized

<400> SEQUENCE: 376
tgacaaatca catccacact                                                   20

<210> SEQ ID NO 377
<211> LENGTH: 20
<212> TYPE: DNA
<213> ORGANISM: Artificial Sequence
<220> FEATURE:
<223> OTHER INFORMATION: Chemically synthesized

<400> SEQUENCE: 377
aatgaaagct gcagtttccc                                                   20

<210> SEQ ID NO 378
<211> LENGTH: 20
<212> TYPE: DNA
<213> ORGANISM: Artificial Sequence
<220> FEATURE:
<223> OTHER INFORMATION: Chemically synthesized

<400> SEQUENCE: 378
gcttaccaat caaggaatct                                                   20

<210> SEQ ID NO 379
<211> LENGTH: 20
<212> TYPE: DNA
<213> ORGANISM: Artificial Sequence
<220> FEATURE:
<223> OTHER INFORMATION: Chemically synthesized

<400> SEQUENCE: 379
ccagaggcaa aaatcagagt                                                   20

<210> SEQ ID NO 380
<211> LENGTH: 20
<212> TYPE: DNA
<213> ORGANISM: Artificial Sequence
<220> FEATURE:
<223> OTHER INFORMATION: Chemically synthesized

<400> SEQUENCE: 380
cgagataaac gctcgagatc                                                   20

<210> SEQ ID NO 381
<211> LENGTH: 20
<212> TYPE: DNA
<213> ORGANISM: Artificial Sequence
<220> FEATURE:
<223> OTHER INFORMATION: Chemically synthesized

<400> SEQUENCE: 381
tatgtgcaca gctttagcaa                                                   20

<210> SEQ ID NO 382
<211> LENGTH: 20
<212> TYPE: DNA
<213> ORGANISM: Artificial Sequence
<220> FEATURE:
<223> OTHER INFORMATION: Chemically synthesized
```

```
<400> SEQUENCE: 382
ttctacacct acatctcccc                                              20

<210> SEQ ID NO 383
<211> LENGTH: 20
<212> TYPE: DNA
<213> ORGANISM: Artificial Sequence
<220> FEATURE:
<223> OTHER INFORMATION: Chemically synthesized

<400> SEQUENCE: 383
agcattaaga gcataactgc                                              20

<210> SEQ ID NO 384
<211> LENGTH: 20
<212> TYPE: DNA
<213> ORGANISM: Artificial Sequence
<220> FEATURE:
<223> OTHER INFORMATION: Chemically synthesized

<400> SEQUENCE: 384
gcaaacaatg ctagccttct                                              20

<210> SEQ ID NO 385
<211> LENGTH: 20
<212> TYPE: DNA
<213> ORGANISM: Artificial Sequence
<220> FEATURE:
<223> OTHER INFORMATION: Chemically synthesized

<400> SEQUENCE: 385
ggtgggaatc accaactttt                                              20

<210> SEQ ID NO 386
<211> LENGTH: 20
<212> TYPE: DNA
<213> ORGANISM: Artificial Sequence
<220> FEATURE:
<223> OTHER INFORMATION: Chemically synthesized

<400> SEQUENCE: 386
gtctgctgca atgctagcag                                              20

<210> SEQ ID NO 387
<211> LENGTH: 20
<212> TYPE: DNA
<213> ORGANISM: Artificial Sequence
<220> FEATURE:
<223> OTHER INFORMATION: Chemically synthesized

<400> SEQUENCE: 387 gcctttccg ggttgatatt                                               20

<210> SEQ ID NO 388
<211> LENGTH: 20
<212> TYPE: DNA
<213> ORGANISM: Artificial Sequence
<220> FEATURE:
<223> OTHER INFORMATION: Chemically synthesized

<400> SEQUENCE: 388
ggttcccgga cttcagtacc                                              20

<210> SEQ ID NO 389
<211> LENGTH: 20
```

<212> TYPE: DNA
<213> ORGANISM: Artificial Sequence
<220> FEATURE:
<223> OTHER INFORMATION: Chemically synthesized

<400> SEQUENCE: 389
aggaagatcc ttaagggtg                                              20

<210> SEQ ID NO 390
<211> LENGTH: 20
<212> TYPE: DNA
<213> ORGANISM: Artificial Sequence
<220> FEATURE:
<223> OTHER INFORMATION: Chemically synthesized

<400> SEQUENCE: 390
ttgctttcca aggaggaacg                                             20

<210> SEQ ID NO 391
<211> LENGTH: 20
<212> TYPE: DNA
<213> ORGANISM: Artificial Sequence
<220> FEATURE:
<223> OTHER INFORMATION: Chemically synthesized

<400> SEQUENCE: 391
gtgaacgcag gctgtttact                                             20

<210> SEQ ID NO 392
<211> LENGTH: 20
<212> TYPE: DNA
<213> ORGANISM: Artificial Sequence
<220> FEATURE:
<223> OTHER INFORMATION: Chemically synthesized

<400> SEQUENCE: 392
ttctgcttca tccacatgaa                                             20

<210> SEQ ID NO 393
<211> LENGTH: 20
<212> TYPE: DNA
<213> ORGANISM: Artificial Sequence
<220> FEATURE:
<223> OTHER INFORMATION: Chemically synthesized

<400> SEQUENCE: 393
ctggcttctt ctgagcttct                                             20

<210> SEQ ID NO 394
<211> LENGTH: 20
<212> TYPE: DNA
<213> ORGANISM: Artificial Sequence
<220> FEATURE:
<223> OTHER INFORMATION: Chemically synthesized

<400> SEQUENCE: 394
tcacgctcta tttttgaga                                              20

<210> SEQ ID NO 395
<211> LENGTH: 20
<212> TYPE: DNA
<213> ORGANISM: Artificial Sequence
<220> FEATURE:
<223> OTHER INFORMATION: Chemically synthesized

<400> SEQUENCE: 395

```
tgaattaaaa gccagggcat                                                      20

<210> SEQ ID NO 396
<211> LENGTH: 20
<212> TYPE: DNA
<213> ORGANISM: Artificial Sequence
<220> FEATURE:
<223> OTHER INFORMATION: Chemically synthesized

<400> SEQUENCE: 396
aagagggacc aatggttttc                                                      20

<210> SEQ ID NO 397
<211> LENGTH: 20
<212> TYPE: DNA
<213> ORGANISM: Artificial Sequence
<220> FEATURE:
<223> OTHER INFORMATION: Chemically synthesized

<400> SEQUENCE: 397
tttccctaag gtatgtgtga                                                      20

<210> SEQ ID NO 398
<211> LENGTH: 20
<212> TYPE: DNA
<213> ORGANISM: Artificial Sequence
<220> FEATURE:
<223> OTHER INFORMATION: Chemically synthesized

<400> SEQUENCE: 398
tcatgtaacc cactttaggt                                                      20

<210> SEQ ID NO 399
<211> LENGTH: 20
<212> TYPE: DNA
<213> ORGANISM: Artificial Sequence
<220> FEATURE:
<223> OTHER INFORMATION: Chemically synthesized

<400> SEQUENCE: 399
gttagtgatg tctggctgtt                                                      20

<210> SEQ ID NO 400
<211> LENGTH: 20
<212> TYPE: DNA
<213> ORGANISM: Artificial Sequence
<220> FEATURE:
<223> OTHER INFORMATION: Chemically synthesized

<400> SEQUENCE: 400
ccacgaggat agctctcata                                                      20

<210> SEQ ID NO 401
<211> LENGTH: 20
<212> TYPE: DNA
<213> ORGANISM: Artificial Sequence
<220> FEATURE:
<223> OTHER INFORMATION: Chemically synthesized

<400> SEQUENCE: 401
atgtagttca cagccaaatg                                                      20

<210> SEQ ID NO 402
<211> LENGTH: 20
<212> TYPE: DNA
<213> ORGANISM: Artificial Sequence
```

<220> FEATURE:
<223> OTHER INFORMATION: Chemically synthesized

<400> SEQUENCE: 402
acatggaaga caggaaccta                      20

<210> SEQ ID NO 403
<211> LENGTH: 20
<212> TYPE: DNA
<213> ORGANISM: Artificial Sequence
<220> FEATURE:
<223> OTHER INFORMATION: Chemically synthesized

<400> SEQUENCE: 403
ctaacagcat agcagcagtg                      20

<210> SEQ ID NO 404
<211> LENGTH: 20
<212> TYPE: DNA
<213> ORGANISM: Artificial Sequence
<220> FEATURE:
<223> OTHER INFORMATION: Chemically synthesized

<400> SEQUENCE: 404
tgtacacaaa ctctgctact                      20

<210> SEQ ID NO 405
<211> LENGTH: 20
<212> TYPE: DNA
<213> ORGANISM: Artificial Sequence
<220> FEATURE:
<223> OTHER INFORMATION: Chemically synthesized

<400> SEQUENCE: 405
ttggtgtagg tatcatctgt                      20

<210> SEQ ID NO 406
<211> LENGTH: 20
<212> TYPE: DNA
<213> ORGANISM: Artificial Sequence
<220> FEATURE:
<223> OTHER INFORMATION: Chemically synthesized

<400> SEQUENCE: 406
gctccattct cagaacttgt                      20

<210> SEQ ID NO 407
<211> LENGTH: 20
<212> TYPE: DNA
<213> ORGANISM: Artificial Sequence
<220> FEATURE:
<223> OTHER INFORMATION: Chemically synthesized

<400> SEQUENCE: 407
gtcaaaagta aggactttca                      20

<210> SEQ ID NO 408
<211> LENGTH: 20
<212> TYPE: DNA
<213> ORGANISM: Artificial Sequence
<220> FEATURE:
<223> OTHER INFORMATION: Chemically synthesized

<400> SEQUENCE: 408
gatttactgt tggagcagct                      20

```
<210> SEQ ID NO 409
<211> LENGTH: 20
<212> TYPE: DNA
<213> ORGANISM: Artificial Sequence
<220> FEATURE:
<223> OTHER INFORMATION: Chemically synthesized

<400> SEQUENCE: 409
tgatgcagaa agtattgggt                                               20

<210> SEQ ID NO 410
<211> LENGTH: 20
<212> TYPE: DNA
<213> ORGANISM: Artificial Sequence
<220> FEATURE:
<223> OTHER INFORMATION: Chemically synthesized

<400> SEQUENCE: 410
ttcaactttg cagtttgcag                                               20

<210> SEQ ID NO 411
<211> LENGTH: 20
<212> TYPE: DNA
<213> ORGANISM: Artificial Sequence
<220> FEATURE:
<223> OTHER INFORMATION: Chemically synthesized

<400> SEQUENCE: 411
ttgaggtatg ggtcagcatc                                               20

<210> SEQ ID NO 412
<211> LENGTH: 20
<212> TYPE: DNA
<213> ORGANISM: Artificial Sequence
<220> FEATURE:
<223> OTHER INFORMATION: Chemically synthesized

<400> SEQUENCE: 412
agcaataact gatggcaaat                                               20

<210> SEQ ID NO 413
<211> LENGTH: 20
<212> TYPE: DNA
<213> ORGANISM: Artificial Sequence
<220> FEATURE:
<223> OTHER INFORMATION: Chemically synthesized

<400> SEQUENCE: 413
gtgctaaatg aaaggcagct                                               20

<210> SEQ ID NO 414
<211> LENGTH: 20
<212> TYPE: DNA
<213> ORGANISM: Artificial Sequence
<220> FEATURE:
<223> OTHER INFORMATION: Chemically synthesized

<400> SEQUENCE: 414
ctttgtcccg tgactgtgta                                               20

<210> SEQ ID NO 415
<211> LENGTH: 20
<212> TYPE: DNA
<213> ORGANISM: Artificial Sequence
<220> FEATURE:
<223> OTHER INFORMATION: Chemically synthesized
```

<400> SEQUENCE: 415
ccagtctttc gtattaatga        20

<210> SEQ ID NO 416
<211> LENGTH: 20
<212> TYPE: DNA
<213> ORGANISM: Artificial Sequence
<220> FEATURE:
<223> OTHER INFORMATION: Chemically synthesized

<400> SEQUENCE: 416
gcttaagact ttccagggta        20

<210> SEQ ID NO 417
<211> LENGTH: 20
<212> TYPE: DNA
<213> ORGANISM: Artificial Sequence
<220> FEATURE:
<223> OTHER INFORMATION: Chemically synthesized

<400> SEQUENCE: 417
gtgctttgag gtaggtctgg        20

<210> SEQ ID NO 418
<211> LENGTH: 20
<212> TYPE: DNA
<213> ORGANISM: Artificial Sequence
<220> FEATURE:
<223> OTHER INFORMATION: Chemically synthesized

<400> SEQUENCE: 418
tattgactgt tgtgcatgct        20

<210> SEQ ID NO 419
<211> LENGTH: 20
<212> TYPE: DNA
<213> ORGANISM: Artificial Sequence
<220> FEATURE:
<223> OTHER INFORMATION: Chemically synthesized

<400> SEQUENCE: 419
gaggagagaa acaccatgat        20

<210> SEQ ID NO 420
<211> LENGTH: 20
<212> TYPE: DNA
<213> ORGANISM: Artificial Sequence
<220> FEATURE:
<223> OTHER INFORMATION: Chemically synthesized

<400> SEQUENCE: 420
gatttagtgt ctctggtggg        20

<210> SEQ ID NO 421
<211> LENGTH: 20
<212> TYPE: RNA
<213> ORGANISM: Artificial Sequence
<220> FEATURE:
<223> OTHER INFORMATION: Chemically synthesized

<400> SEQUENCE: 421
uauguaacac caauuuaccc        20

<210> SEQ ID NO 422

```
<211> LENGTH: 20
<212> TYPE: RNA
<213> ORGANISM: Artificial Sequence
<220> FEATURE:
<223> OTHER INFORMATION: Chemically synthesized

<400> SEQUENCE: 422
ugugauuucc aaauagucgu                                               20

<210> SEQ ID NO 423
<211> LENGTH: 20
<212> TYPE: RNA
<213> ORGANISM: Artificial Sequence
<220> FEATURE:
<223> OTHER INFORMATION: Chemically synthesized

<400> SEQUENCE: 423
guuuuguagc uugacaagcg                                               20

<210> SEQ ID NO 424
<211> LENGTH: 20
<212> TYPE: RNA
<213> ORGANISM: Artificial Sequence
<220> FEATURE:
<223> OTHER INFORMATION: Chemically synthesized

<400> SEQUENCE: 424
uguauauugu auaucauuca                                               20

<210> SEQ ID NO 425
<211> LENGTH: 20
<212> TYPE: RNA
<213> ORGANISM: Artificial Sequence
<220> FEATURE:
<223> OTHER INFORMATION: Chemically synthesized

<400> SEQUENCE: 425
gcguuccaag acacauuuuu                                               20

<210> SEQ ID NO 426
<211> LENGTH: 20
<212> TYPE: RNA
<213> ORGANISM: Artificial Sequence
<220> FEATURE:
<223> OTHER INFORMATION: Chemically synthesized

<400> SEQUENCE: 426
cguuacccau auaugcauau                                               20

<210> SEQ ID NO 427
<211> LENGTH: 20
<212> TYPE: RNA
<213> ORGANISM: Artificial Sequence
<220> FEATURE:
<223> OTHER INFORMATION: Chemically synthesized

<400> SEQUENCE: 427
ugacugguua aggcgcguaa                                               20

<210> SEQ ID NO 428
<211> LENGTH: 20
<212> TYPE: RNA
<213> ORGANISM: Artificial Sequence
<220> FEATURE:
<223> OTHER INFORMATION: Chemically synthesized

<400> SEQUENCE: 428
```
cugcugacca caacugaugc                    20

<210> SEQ ID NO 429
<211> LENGTH: 20
<212> TYPE: RNA
<213> ORGANISM: Artificial Sequence
<220> FEATURE:
<223> OTHER INFORMATION: Chemically synthesized

<400> SEQUENCE: 429
cacugagaug auucacuuga                    20

<210> SEQ ID NO 430
<211> LENGTH: 20
<212> TYPE: RNA
<213> ORGANISM: Artificial Sequence
<220> FEATURE:
<223> OTHER INFORMATION: Chemically synthesized

<400> SEQUENCE: 430
gggcuauuua ggccuuuagu                    20

<210> SEQ ID NO 431
<211> LENGTH: 20
<212> TYPE: RNA
<213> ORGANISM: Artificial Sequence
<220> FEATURE:
<223> OTHER INFORMATION: Chemically synthesized

<400> SEQUENCE: 431 uauuccucg aacuuguuca                     20

<210> SEQ ID NO 432
<211> LENGTH: 20
<212> TYPE: RNA
<213> ORGANISM: Artificial Sequence
<220> FEATURE:
<223> OTHER INFORMATION: Chemically synthesized

<400> SEQUENCE: 432
gcaaggcauc uugauugagu                    20

<210> SEQ ID NO 433
<211> LENGTH: 20
<212> TYPE: RNA
<213> ORGANISM: Artificial Sequence
<220> FEATURE:
<223> OTHER INFORMATION: Chemically synthesized

<400> SEQUENCE: 433
ccgcacuugc agucagaucc                    20

<210> SEQ ID NO 434
<211> LENGTH: 20
<212> TYPE: RNA
<213> ORGANISM: Artificial Sequence
<220> FEATURE:
<223> OTHER INFORMATION: Chemically synthesized

<400> SEQUENCE: 434
guguagagag acaagaugca                    20

<210> SEQ ID NO 435
<211> LENGTH: 20
<212> TYPE: RNA

```
<213> ORGANISM: Artificial Sequence
<220> FEATURE:
<223> OTHER INFORMATION: Chemically synthesized

<400> SEQUENCE: 435
aauuggacau uuauugcagg                                              20

<210> SEQ ID NO 436
<211> LENGTH: 20
<212> TYPE: DNA
<213> ORGANISM: Artificial Sequence
<220> FEATURE:
<223> OTHER INFORMATION: Chemically synthesized

<400> SEQUENCE: 436
ttcgaaacga tctctaaagc                                              20

<210> SEQ ID NO 437
<211> LENGTH: 20
<212> TYPE: DNA
<213> ORGANISM: Artificial Sequence
<220> FEATURE:
<223> OTHER INFORMATION: Chemically synthesized

<400> SEQUENCE: 437
tttcgaacga ttatcaatgt                                              20

<210> SEQ ID NO 438
<211> LENGTH: 20
<212> TYPE: DNA
<213> ORGANISM: Artificial Sequence
<220> FEATURE:
<223> OTHER INFORMATION: Chemically synthesized

<400> SEQUENCE: 438
cttgattttg cttcggagaa                                              20

<210> SEQ ID NO 439
<211> LENGTH: 20
<212> TYPE: DNA
<213> ORGANISM: Artificial Sequence
<220> FEATURE:
<223> OTHER INFORMATION: Chemically synthesized

<400> SEQUENCE: 439
tatgcggaaa tcgttactct                                              20

<210> SEQ ID NO 440
<211> LENGTH: 20
<212> TYPE: DNA
<213> ORGANISM: Artificial Sequence
<220> FEATURE:
<223> OTHER INFORMATION: Chemically synthesized

<400> SEQUENCE: 440
attcaactta aacattttcg                                              20

<210> SEQ ID NO 441
<211> LENGTH: 20
<212> TYPE: DNA
<213> ORGANISM: Artificial Sequence
<220> FEATURE:
<223> OTHER INFORMATION: Chemically synthesized

<400> SEQUENCE: 441
tcatctcact gtccgtaaga                                              20
```

<210> SEQ ID NO 442
<211> LENGTH: 20
<212> TYPE: DNA
<213> ORGANISM: Artificial Sequence
<220> FEATURE:
<223> OTHER INFORMATION: Chemically synthesized

<400> SEQUENCE: 442
tcaaccatga aaacaattcg                                                   20

<210> SEQ ID NO 443
<211> LENGTH: 20
<212> TYPE: DNA
<213> ORGANISM: Artificial Sequence
<220> FEATURE:
<223> OTHER INFORMATION: Chemically synthesized

<400> SEQUENCE: 443
gcattgcgac ttgtacaatg                                                   20

<210> SEQ ID NO 444
<211> LENGTH: 20
<212> TYPE: DNA
<213> ORGANISM: Artificial Sequence
<220> FEATURE:
<223> OTHER INFORMATION: Chemically synthesized

<400> SEQUENCE: 444
acacgtcttt taagacttca                                                   20

<210> SEQ ID NO 445
<211> LENGTH: 20
<212> TYPE: DNA
<213> ORGANISM: Artificial Sequence
<220> FEATURE:
<223> OTHER INFORMATION: Chemically synthesized

<400> SEQUENCE: 445
tttgcttaat ttgcaacatt                                                   20

<210> SEQ ID NO 446
<211> LENGTH: 20
<212> TYPE: DNA
<213> ORGANISM: Artificial Sequence
<220> FEATURE:
<223> OTHER INFORMATION: Chemically synthesized

<400> SEQUENCE: 446
acatttcact agttatatga                                                   20

<210> SEQ ID NO 447
<211> LENGTH: 20
<212> TYPE: DNA
<213> ORGANISM: Artificial Sequence
<220> FEATURE:
<223> OTHER INFORMATION: Chemically synthesized

<400> SEQUENCE: 447
atttgcatcc gcttccgcat                                                   20

<210> SEQ ID NO 448
<211> LENGTH: 20
<212> TYPE: DNA
<213> ORGANISM: Artificial Sequence
<220> FEATURE:

```
<223> OTHER INFORMATION: Chemically synthesized

<400> SEQUENCE: 448
agttgcagga tcccttggtg                                              20

<210> SEQ ID NO 449
<211> LENGTH: 20
<212> TYPE: DNA
<213> ORGANISM: Artificial Sequence
<220> FEATURE:
<223> OTHER INFORMATION: Chemically synthesized

<400> SEQUENCE: 449
gcaggcggat ttcttgtcgc                                              20

<210> SEQ ID NO 450
<211> LENGTH: 20
<212> TYPE: DNA
<213> ORGANISM: Artificial Sequence
<220> FEATURE:
<223> OTHER INFORMATION: Chemically synthesized

<400> SEQUENCE: 450
ggaaagctca ctcggagcag                                              20

<210> SEQ ID NO 451
<211> LENGTH: 20
<212> TYPE: DNA
<213> ORGANISM: Artificial Sequence
<220> FEATURE:
<223> OTHER INFORMATION: Chemically synthesized

<400> SEQUENCE: 451
gcctctactc cagatctttt                                              20
```

METHOD FOR DETECTING CHROMOSOME STRUCTURE AND GENE EXPRESSION SIMULTANEOUSLY IN SINGLE CELLS

CROSS-REFERENCE TO RELATED APPLICATIONS

This application is the U.S. national phase application filed under 35 U.S.C. § 371 claiming benefit to International Patent Application No. PCT/US2012/023974, filed on Feb. 6, 2012, which is entitled to priority under 35 U.S.C. § 119(e) to U.S. Provisional Patent Application No. 61/439,623, filed on Feb. 4, 2011, each of which application is hereby incorporated herein by reference in its entirety.

BACKGROUND OF THE INVENTION

The DNA in a single human cell, if fully elongated, would stretch for roughly two meters. However, each cell compacts these incredibly long polymeric molecules within the cell's nucleus, a space just a few microns across. Increasingly, researchers are finding that this compacted conformation is not just a random "ball of string", but rather is highly organized and dynamically regulated (Cremer et al., 2001, Nat Rev Genet 2: 292-301). Developing a better understanding of this compacted form will provide key insights in how the spatial organization of genetic information in the nucleus affects its readout via gene expression.

Gene expression involves the transcription of mRNA molecules from the genome followed by the export of those mRNAs to the cytoplasm. Evidence indicates that the structure of chromosomes, generally organized into distinct territories in the nucleus (Cremer et al., 2001, Nat Rev Genet 2: 292-301), play a role in both processes (Fraser et al., 2007, Nature 447: 413-417; Misteli, 2007, Cell 128: 787-800; Papantonis et al., 2010, Curr Opin Cell Biol. 22(3): 271-6). Indeed, a numerical accounting of transcription reveals that the abundances of the large enzyme complexes required for RNA polymerization and splicing range between hundreds to thousands per cell that must somehow transcribe the many tens of thousands of genes in the nucleus (Jackson et al., 1998, Mol Biol Cell 9: 1523-1536; Osborne et al., 2004, Nat Genet 36: 1065-1071; Wansink et al., 1993, J Cell Biol 122: 283-293). Some data suggest that sets of actively transcribed genes localize to "transcription factories" (Iborra et al., 1996, J Cell Sci 109: 1427-1436; Schoenfelder et al., 2010, Nat Genet 42: 53-61; Sexton et al., 2007, Semin Cell Dev Biol 18: 691-697). Limited accessibility to and transient formation of these factories may underlie the intermittent nature of gene expression that both we and others have observed (Raj et al., 2006, PLoS Biol 4: e309; Raj et al., 2008, Cell 135: 216-226).

Meanwhile, for many years, researchers reasoned that the high density of polymeric materials in the nucleus would make RNA diffusion prohibitively slow, leading to the "gene gating" hypothesis (Blobel, 1985, Proc Natl Acad Sci USA 82: 8527-8529) that genes themselves must move to nuclear periphery for the export of the RNA to be reasonably efficient. Indeed, there is some evidence for this, with some genes moving to the periphery upon activation and physically associating with nuclear pores complexes (Brown et al., 2007, Curr Opin Genet Dev 17: 100-106; Capelson et al., 2010, Cell 140: 372-383; Casolari et al., 2004, Cell 117: 427-439; Kalverda et al., 2010, Cell 140: 360-371). However, biophysical analyses have shown that RNA diffusion in the nucleus is rather rapid and thus not limiting (Vargas et al., 2005, Proc Natl Acad Sci USA 102: 17008-17013), and the majority of genes appear to remain in the nuclear interior (often exhibiting silencing at the periphery, in fact (Chuang et al., 2006, Curr Biol 16: 825-831; Kosak et al., 2002, Science 296: 158-162)).

Unfortunately, there is a lack of a clear picture of chromosome structure and gene expression, which stems from the lack of effective tools for measuring genetic structure and function simultaneously at the single cell level. Most conventional imaging assays for chromosome structure focus only on the position of one or two loci at a time, whereas global biochemical approaches provide indirect measurements averaged over populations of many thousands to millions of cells. In either case, gene expression data are difficult to obtain. For these reasons, questions remain regarding how spatially ordered or disordered gene expression is on interphase chromosomes, or regarding the variability of chromosome configurations, and how they contribute to variability in gene expression.

Currently, two broad classes of methods are used to study chromosome structure. One method is chromosome conformation capture (3C) (Dekker et al., 2002, Science 295: 1306-1311) and its variants, most notably (Duan et al., 2010, Nature 465(7296):363-7; Lieberman-Aiden et al., 2009, Science 326: 289-293). 3C is a biochemical technique that measures the frequency of direct physical interactions between genomic loci in populations of cells. While the Hi-C incarnation of the method yields genome wide information on these interactions, it does have a number of drawbacks. For example, it does not yield single cell data, it does not give any information about expression, and it only yields interaction probabilities rather than chromosome structure per se.

The other approach is DNA FISH, involving the detection of fluorescently labeled probes targeting small or large regions of DNA (or even whole chromosomes). This approach is more direct, but studies so far have been limited to only a few loci, limiting its scope. Most importantly though, the harsh conditions required to denature DNA in preparation for DNA FISH cause significant RNA degradation, generally precluding its combination with RNA FISH methods except for highly abundant targets (Chaumeil et al., 2006, Genes Dcv 20: 2223-2237) or using signal amplification methods that are difficult to multiplex (Takizawa et al., 2008, Genes Dev 22: 489-498).

There is a need for a method that allows one to measure gene expression of one or many genes via RNA FISH while simultaneously obtaining chromosomal structural information about chromosomes. The present invention satisfies this need.

BRIEF SUMMARY OF THE INVENTION

The present invention relates to a method for determining the structural conformation of a chromosome in a cell. The method includes the step of hybridizing a plurality of target sequences of RNA in the cell with members of at least one set of fluorescently labeled oligonucleotide probes, wherein the plurality of targeted sequences of RNA are transcribed from portions of at least one chromosome, and wherein the pattern of fluorescently labeled probes hybridized to the target sequences of RNA is indicative of the structural conformation of the chromosome. In one embodiment, the location of the hybridized probes is simultaneously indicative of the chromosomal location of gene expression for the transcribed RNA. In another embodiment, the number, intensity, or both, of fluorescing probes is indicative of the level of gene expression at the chromosomal location. In yet another embodiment, each set of fluorescently labeled oligonucleotide probe sets are labeled with a different fluorophore resulting in a different and distinguishable color when measurably fluorescent. In yet another embodiment, the method includes the step of counting fluorescent spots corresponding to single molecules of target RNA to obtain a gene expression profile corresponding to the simultaneously determined, associated chromosomal conformation. In yet another embodiment, the probes are non-overlapping. In yet another embodiment, probe hybridization occurs in the cell nucleus. In yet another embodiment, the cell is a living cell. In yet another embodiment, the target sequences of RNA are endogenous RNA. In yet another embodiment, the cell is a mammalian cell, an invertebrate cell, a yeast cell or a bacterium. In yet another embodiment, the cell is a human cell. In yet another embodiment, the cell is a cancer cell. In yet another embodiment, the targeted RNA is mRNA. In yet another embodiment, the targeted mRNA sequence is at least a portion of an intron of the mRNA sequence. In yet another embodiment, the targeted RNA is non-coding RNA (ncRNA).

The present invention also relates to an assay for determining the structural conformation of a chromosome in a cell. The assay includes the hybridization of a plurality of target sequences of mRNA in the cell with members of a plurality of fluorescently labeled oligonucleotide probe sets, wherein each probe set utilizes a distinguishable color, the plurality of targeted sequences of mRNA are transcribed from portions of at least one chromosome, and the pattern of fluorescently labeled probes hybridized to the target sequences of mRNA is indicative of the structural conformation of the chromosome. In one embodiment, the assay includes the location of the hybridized probes is simultaneously indicative of the chromosomal location of gene expression for the transcribed mRNA. In another embodiment, the number, the intensity, or both, of fluorescing probes is indicative of the level of gene expression at the chromosomal location. In yet another embodiment, the assay includes the step of counting fluorescent spots corresponding to single molecules of target mRNA to obtain a gene expression profile corresponding to the simultaneously determined, associated chromosomal conformation. In yet another embodiment, the probes are non-overlapping. In yet another embodiment, probe hybridization occurs in the cell nucleus. In yet another embodiment, the cell is a living cell. In yet another embodiment, the target sequences of mRNA are transcribed from an endogenous gene. In yet another embodiment, the cell is a mammalian cell, an invertebrate cell, a yeast cell or a bacterium. In yet another embodiment, the cell is a human cell. In yet another embodiment, the cell is a cancer cell. In yet another embodiment, the targeted mRNA sequence is at least a portion of an intron of the mRNA sequence.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

The patent or application file contains at least one drawing executed in color. Copies of this patent or patent application publication with color drawing(s) will be provided by the Office upon request and payment of the necessary fee.

FIG. 1, comprising

FIG. 1A depicts introns labeled at the site of transcription, yielding information about both the target gene's location and expression level. By employing a barcoded color scheme (with pseudocolors), dozens, or even hundreds of individual genes can be detected along a chromosome. FIG. 1B depicts 18 genes targeted on chromosome 19. The first third of the chromosome is in red, the middle third in green and the last third in magenta. Both chromosomes are similarly configured in the nucleus, with the first third residing in between the middle and the final thirds. FIG. 1C depicts simultaneously targeted chromosome 19 (cyan) and EEF2 messenger RNA (magenta) in the same cell, demonstrating the ability to detect chromosomes, genes and single RNA molecules at the same time in single cells.

FIGS. 2A and 2B, is a depiction of a single molecule detection of chromosomal translocations and the resultant fusion transcript. FIG. 2A depicts transcripts of a normal cell and fusion transcripts of a cancer cell. By labeling both ends of the fusion with individual colors, fusion transcripts can be directly detected in situ at the same time as detecting the causative chromosomal abnormality (FIG. 2B).

FIG. 3, comprising FIG. 3A depicts a scheme for uniquely labeling several different genes along a chromosome within a single cell by using combinations of fluorophores for the oligonucleotides. FIG. 3B depicts a scheme to uniquely label 20 different genes using combinations of 2 or 3 fluorophores from a palette of 5 spectrally distinct fluorophores. FIG. 3C depicts a DAPI stain of the nucleus. FIGS. 3D-3H depict raw fluorescence images in the 5 true color channels for 20 genes labeled with the pseudo-coloring scheme in FIG. 3B. FIG. 3I depicts the DAPI image of the nucleus overlaid with the resultant computationally identified pseudocolored spots. The color of the spots depicts where upon the chromosome the particular gene is located.

FIGS. 4A-4C, depicts a scheme for measuring transcription directly from translocated chromosomes. FIG. 4A depicts a diagram showing the karyotype of chromosome 19 in HeLa cells, which contain two intact copies of chromosome 19 and one copy that has been split, with one section fused to chromosome 13 and the other fuesd to chromosome 6. FIG. 4B depicts the measurement of instantaneous transcriptional activity on a per chromosome basis through the isolation of individual chromosomes and chromosome fragments. FIG. 4C depicts a chart showing measured transcriptional activity for 20 genes along chromosome 19. The transcription rate for the genes on the portion of chromosome 19 fused to chromosome 13 was found to be highter than the genes of the intact chromosome 19, while the portion of chromosome 19 that is fused to chromosome 6 was found to transcribe about as often as those on the intact chromosome 19.

FIG. 5A-5D, depict live imaging of an endogenous RNA molecule. FIG. 5A depicts a live *Drosophila melanogaster* S2 cell, wherein the nucleus and the roX2 RNA are as marked, in which probes have been delivered against roX2 to the cell. FIG. 5B depicts the DAPI (nucleus) of these S2 cells after fixation. FIG. 5C depicts FISH signals corresponding to roX2 in the same fixed cells as in FIG. 5B. FIG. 5D depicts the live imaging signal remaining in the same fixed cells as in FIGS. 5B-5C.

FIGS. 6A-6B, depicts a demonstration of the detection of an endogenous RNA transcription site with probes delivered to living cells. Specifically, RNA from the MtnA gene has been targeted. FIG. 6A depicts spots corresponding to transcription sites of MtnA targeted by the probe. FIG. 6B depicts the same MtnA transcripts labeled with RNA FISH probes after fixation. The strong colocalization shows that the correct transcripts are being targeted.

DETAILED DESCRIPTION

Figure 1A:
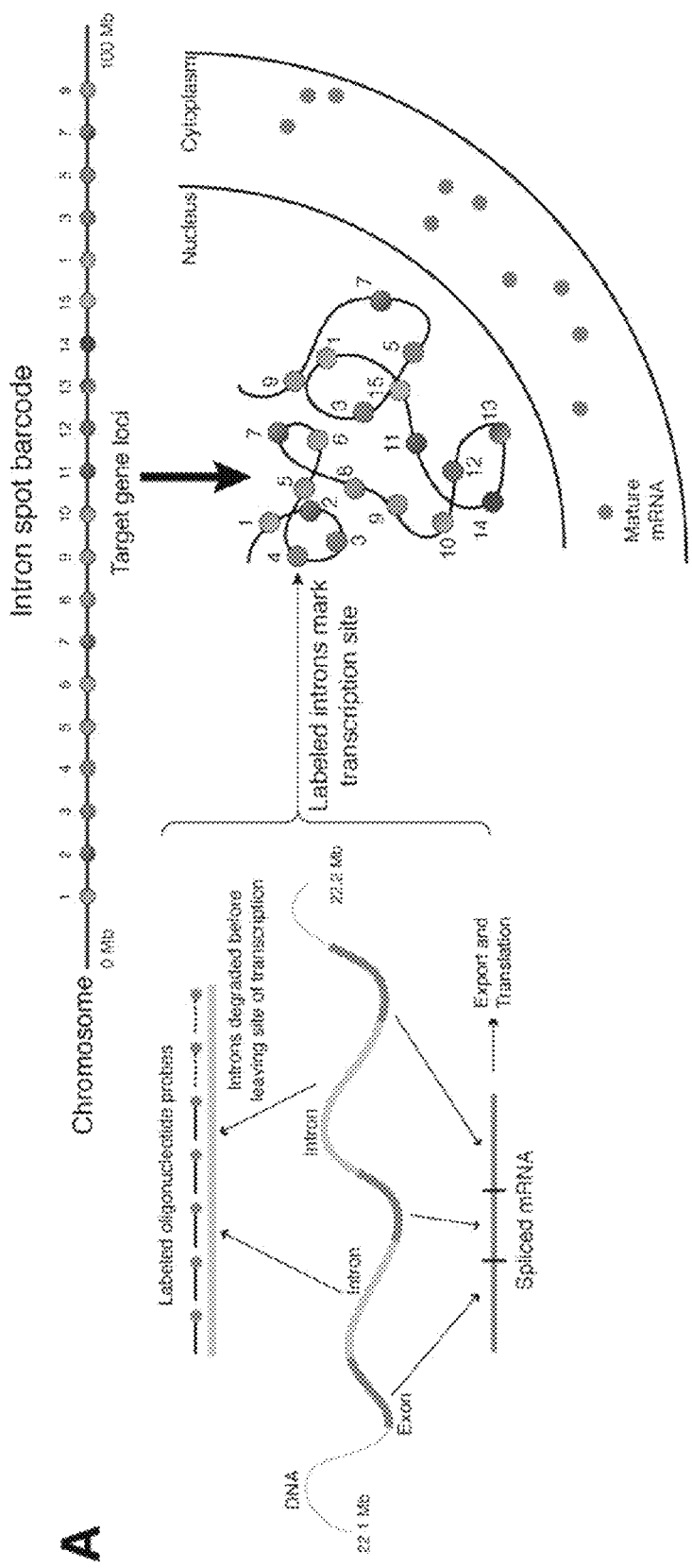
FIGS. 1A-1C, depicts the detection of chromosome structure and gene expression in single cells.

The present invention relates to systems and methods for measuring chromosome structure and gene expression. In one embodiment, the present invention includes an assay for determining the spatial organization of gene expression in the nucleus. The assay can be used in conjunction with computational and analytical frameworks. In another embodiment, the assay can be used for determining the role spatial organization of gene expression plays in disease.

The present invention also includes a method based on fluorescence in situ hybridization (FISH) that simultaneously yields information on the physical position and expression of individual genes. By lighting up a large number of targets on a particular chromosome using a bar-coding scheme, the large scale structure of an entire chromosome can be determined. In one embodiment, the method includes measuring the expression of particular or selected genes while simultaneously determining chromosomal structure, providing a meso-scale "in situ positional expression array". The methods of the present invention can also be compared with biophysical models of chromosome structure, while also developing analytical tools for understanding the relationship between structure and gene expression. The present invention can also be used in vivo and thus provides for the detection of both a detailed dynamic description of chromosome structure together with the expression of many genes in living cells, where large numbers of chromosomal loci can be detected in live human cells and subject them to time-lapse microscopic analysis. Thus, the present invention relates to a barcoded RNA FISH method that targets DNA loci across the chromosome, effectively yielding data on chromosome structure and the expression of many genes simultaneously.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "disease" is a state of health of an animal, preferably a mammal and more preferably, a human, wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

A "portion" of a polynucleotide means at least at least about fifteen to about fifty sequential nucleotide residues of the polynucleotide. It is understood that a portion of a polynucleotide may include every nucleotide residue of the polynucleotide.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Naturally occurring" as used herein describes a composition that can be found in nature as distinct from being artificially produced. For example, a nucleotide sequence present in an organism, which can be isolated from a source in nature and which has not been intentionally modified by a person in the laboratory, is naturally occurring.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides," The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The terms "patient," "subject," "individual," and the like are used interchangeably herein, and refer to any animal, or cells thereof whether in vitro or in situ, amenable to the methods described herein. Preferably, the patient, subject or individual is a mammal, and more preferable, a human.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

"Variant" as the term is used herein, is a nucleic acid sequence or a peptide sequence that differs in sequence from a reference nucleic acid sequence or peptide sequence respectively, but retains essential properties of the reference molecule, Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The systems and methods of the present invention allow one to illuminate directly the structure and function of a living cell's nucleus in real-time through the use of fluorescence based tools, then use those tools to construct a comprehensive, quantitative model of the relationship between structure and function. Applications for the present invention are many, and can provide greater understanding of disease and clinical diagnosis.

The present invention combines the richness of single molecule imaging data, which gives very high quality data on the abundance, locations and dynamics of biomolecules, with the ability to generate more global biological panoramas by measuring the expression and positions of multiple genes, including tens and even hundreds of genes, at the same time, while also performing systematic genome-wide perturbations. Further, the generation and analysis of intracellular spatial information represents a new direction in systems biology, given that the vast majority of studies to date concentrate mostly on overall mRNA or protein abundance. Using the system and methods of the present invention, spatial maps of chromosome structure can be generated, and can create a new paradigm in the understanding of the biological importance of spatial organization.

In the case of the in situ experiments described herein, the present invention leaves the system unperturbed in the sense that no genetic modifications are required. This enables swift and broad adoption in a variety of contexts, and in particular can enhance the potential to use the system and methods of the present invention in clinical diagnostics.

Measuring Gene Expression and Determination of Chromosomal Structure

The present invention includes systems and methods for determining the spatial organization of gene expression in the nucleus. Spatial control of chromosome structure is a critical regulating feature in the control of gene expression, as it can influence variability in gene expression from cell to cell. Spatial control of chromosome structure can even provide a structural basis for the coordination of gene network modules within the nucleus. The present invention, in combination with computational and analytical frameworks, can further provide a new basis for incorporating spatial information in understanding regulation and organization of genetic information, and can greatly expand the understanding of the role spatial organization of gene expression plays in disease and clinical diagnosis.

The present invention utilizes direct visualization, quantitative measurements, and analytical and computational modeling to elucidate biological function. In one embodiment, the present invention includes a method based on fluorescence in situ hybridization (FISH) that simultaneously yields information on the physical position and expression of individual genes.

For example, by lighting up a large number of these targets on a particular chromosome at the same time using a bar-coding scheme, one can effectively read out the large scale structure of an entire chromosome while also measuring the expression of those genes, providing a meso-scale "in situ positional expression array" (FIG. 1A). In one embodiment, the number of targets can be in the range of about 1-1000 unique targets. In another embodiment, the number of targets can be in the range of about 5-200 unique targets. In yet another embodiment, the number of targets can be in the range of about 10-100 unique targets. Alternatively, the number of targets can be greater than 1000, greater than 5000, or even greater than 10,000.

Figure 4:
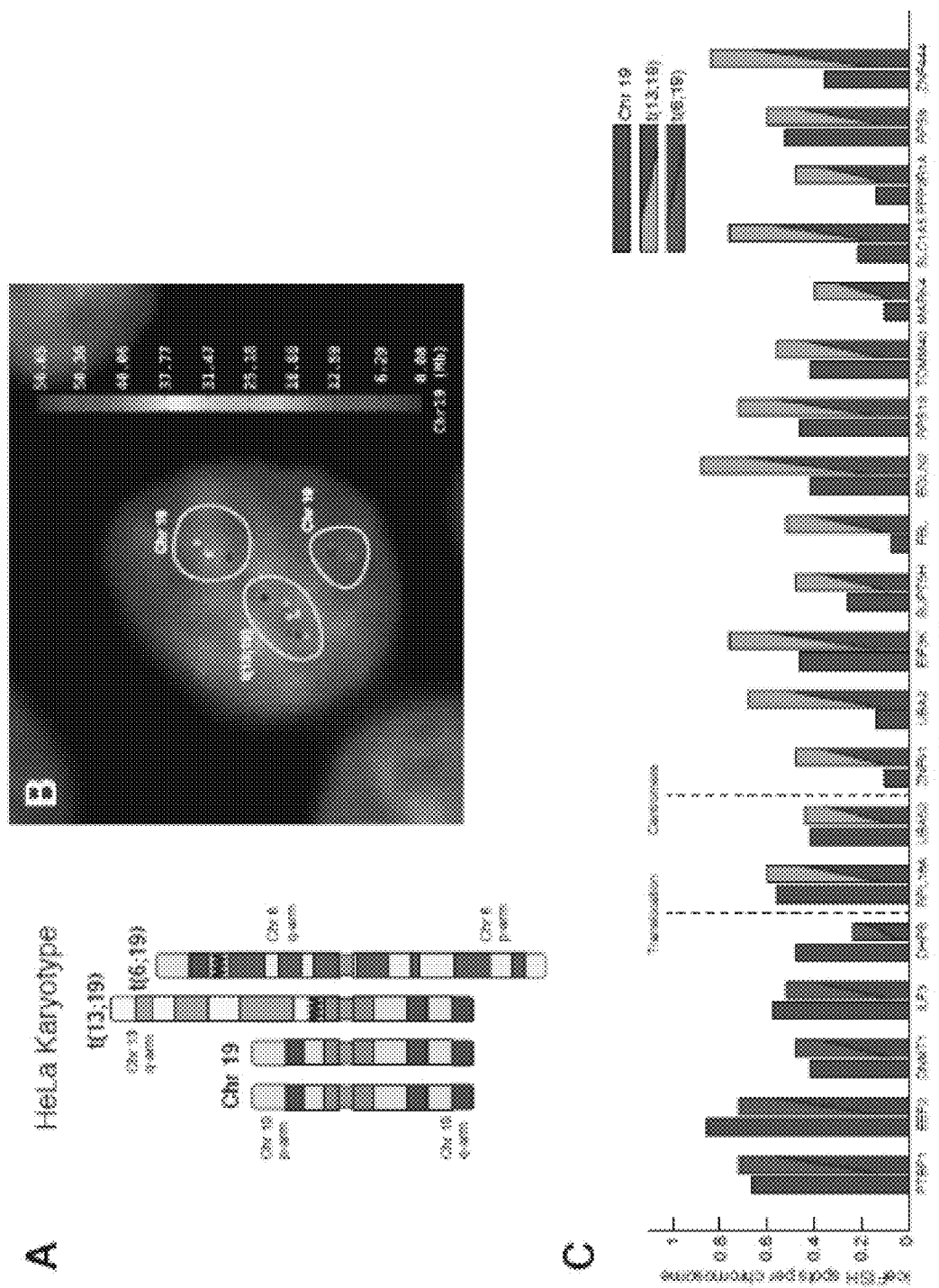
FIG. 4, comprising

In one embodiment, these targeted regions correspond to the location of a gene on a particular chromosome. The method of the present invention permits the simultaneous labeling of many genes and gene locations at the same time, effectively "painting" target chromosomes. In one embodiment, the number of genes that can be simultaneously labeled may be between 1-100. In another embodiment, the number of labeled genes can be between 5-50. In yet another embodiment, the number of labeled genes can be between 10-30. For example, the transcription site of 20 unique genes along a single chromosome in a single cell can be detected using color-coded probes as described elsewhere herein (FIGS. 1 and 4). In another embodiment, these spot data for 20 genes can be used to reconstruct chromosome conformations of actively transcribing genes (FIG. 4). The present invention provides a false spot identification rate below 10%, preferably below 5%, and even more preferably below 4%, below 3%, below 2%, and even below 1%.

The present invention includes methods of measuring gene expression. The presence or absence of a spot for a particular gene indicates whether the gene is actively transcribing at a particular moment in time. Not every gene expresses in every cell because transcription is itself a pulsatile process. In one embodiment, the overall rate of transcription of a particular gene can be determined by quantifying both (or either of) the frequency with which a spot is observed over an ensemble of cells or the intensity of the observed spots. Through spatial chromosome segregation, the location of each spot, and therefore each gene or portion thereof, can be assigned to a particular chromosome. By repeating this process for a large number of cells, the transcriptional frequency and gene expression (which is proportional to the rate of transcription) can be determined on a per-chromosome basis. Thus, the present invention provides a mechanism to measure gene expression from particular chromosomes.

In another embodiment, gene expression can be measured for a chromosomal fragment. In yet another embodiment, gene expression can be measured for a chromosomal fragment resulting from translocated chromosomes. For example, a translocated chromosomal fragment can be compared to the intact copy of the chromosome to determine whether gene expression of the chromosomal fragment is the same or different.

The present invention also includes methods of profiling gene expression on a per-chromosome basis. This allows for analysis of chromosome-copy-specific expression levels, and, thus, a method for SNP (single nucleotide polymorphism) expression analysis in single cells, which to date has been very difficult to accomplish. For example, in normal cells, the difference between the maternal and paternal copies of a chromosome is determined by imprinted genes. These genes, of which only a small number have been isolated by scientists, have been shown to transcribe only from either the maternal or paternal copy, but never both. Such genes can be used as markers to determine which copy of a particular chromosome of interest is the maternal copy and which is the paternal copy. In one embodiment, gene expression can be measured for imprinted genes. For example, using imprinted genes as markers can determine which copy of a particular chromosome is the maternal copy and which is the paternal copy.

Figures 1B, 1C:
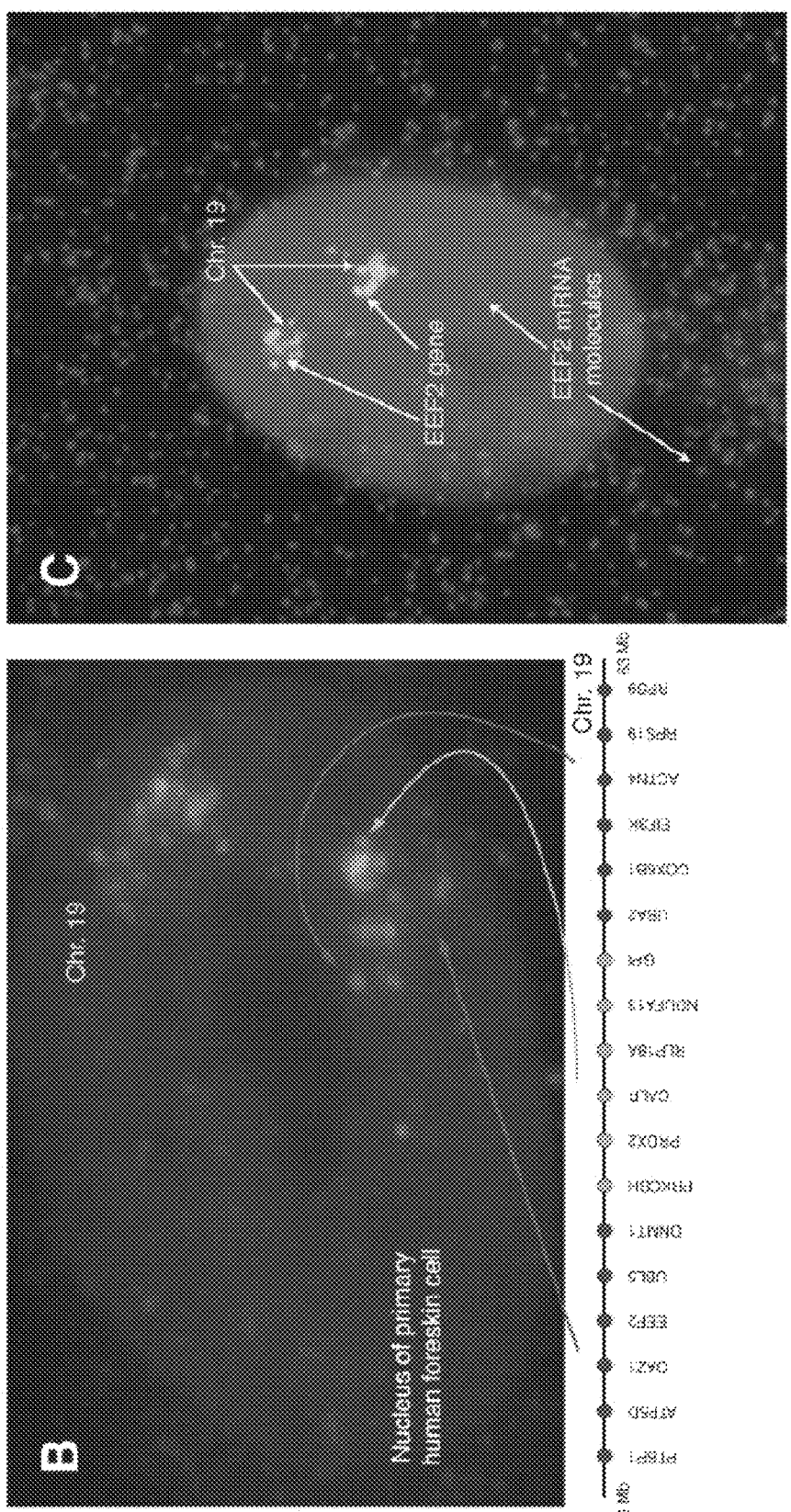

The methods of the present invention can also be compared with biophysical models of chromosome structure, while also developing analytical tools for understanding the relationship between structure and gene expression. As demonstrated herein, chromosomes can adopt a wide variety of configurations, and these configurations are related to gene expression (FIG. 1B). To probe the molecular mechanisms underlying the patterns observed, an RNAi screening platform can be used to search for proteins that affect spatial aspects of gene expression, establishing a new bar of sophistication in the use of imaging in large-scale screening.

Data generated by the systems and methods of the present invention can further be coupled with quantitative analysis. For example, image analysis software can be used to facilitate the accurate extraction of both position and expression values from microscope data. Once processed, one level of analysis is to simply analyze the configuration space of actively expressed genes on a chromosome. Existing models primarily focus on polymer models of chromosome structure, consisting of random walk, random loop and globule descriptions (Lieberman-Aiden et al., 2009, Science 326: 289-293; Cook et al., 2009, J Cell Biol 186: 825-834). While data generated via the present invention will certainly inform such models, the ability to generate and correlate positional data with gene expression data can add an important new dimension to such models, which generally do not incorporate information about transcriptional status. Thus, the present invention provides a platform and method to test hypotheses about deviations from null models in which expression does not correlate with structure, i.e., whether certain genes express only when the chromosome adopts certain conformations.

Applications to Living Cells and Disease

The present invention can also be used in living cells. Through the development and application of new in vivo nucleic acid detection techniques, large numbers of chromosomal loci can be detected in live human cells and subjected to time-lapse microscopic analysis. Thus, the present invention provides for the detection of both a detailed dynamic description of chromosome structure together with the expression of many genes in living cells, marking a huge advance in the field. The present invention can also have broad impact in other fields as well. For example, the direct visualization of nuclear structure and gene expression can include applications in developmental systems, such as C. elegans.

The present invention also includes methods for live imaging in cells. For example, a live imaging probe can be delivered into live cells, and the probe signals can then be detected using methods described herein. In one embodiment, the live imaging probe contains about 1-100 labeled oligonucleotides. In another embodiment, the probe contains about 4-50 labeled oligonucleotides. The signals can then be verified by RNA FISH methods as described herein. Non-limiting examples of the application of live imaging methods include detection of endogenous RNA in single living cells or determination of chromosome structure. As contemplated herein, applications of the present invention to human disease include the ability to identify the formation of stereotypical chromosomal translocations in cancer. Given the widespread occurrence of gene fusions in cancer and the directness of the methods of the present invention, a much deeper understanding of the mechanisms by which translocations are produced can be had. The non-perturbative nature of the present invention also means that these methods can also be applied to tissue sections, conceivably resulting in improved molecular diagnostic tools via the detailed examination of translocations in tumors. More generally, the ways in which translocations affect gene expression can be elucidated and establish the structure/function relationship as a biomarker for disease.

For example, the present invention can be applied to frozen and paraffin embedded tissue samples, representing a crucial step towards clinical viability. By studying the dynamics of the translocation itself along with the induced differences in gene expression at the single molecule level, the genesis of specific translocations and how they influence the expression of the relevant fusion transcripts can be determined. The present invention may also be used as or in conjunction with clinical diagnostics and new assays for screening compounds. Thus, the present invention provides for a better understanding of how the structure of the nucleus affects gene expression by directly visualizing nuclear processes in fixed and living cells.

RNA FISH Method

The present invention includes use of a highly sensitive and specific RNA FISH method to label the introns of genes, as shown in FIG. 1A. Additional description and explanation of RNA FISH methodologies can be found in copending patent application publication number WO/2010/030818, the entire contents of which are incorporated by reference herein it its entirety.

Introns are typically degraded shortly after transcription before they have a chance to move away from the site of transcription itself. When targeted by the RNA FISH method of the present invention, a spot can be seen in the microscope that yields two pieces of information. First, the brightness, or the presence or absence, of the spot is related to the instantaneous rate of transcription, and the location of the spot gives the position of the gene, accurate to lengths below that of the diffraction limit of the microscope. This method further involves the designing of probes for the simultaneous labeling of dozens and even hundreds of introns spaced along a single chromosome, thereby creating a three-dimensional "pointillist painting" of the chromosome, with each individual point corresponding to a single gene.

For example, about 1-1000 different probes, each labeled with a similar or different fluorophore, are hybridized simultaneously to a target sequence of a nucleotide molecule, such as an RNA molecule. In certain embodiments, the number of probes can range from 4-100, from 10-80, from 15-70, or from 20-60. A fluorescent spot is created that can be detected from the combined fluorescence of the multiple probes. The probes can be non-overlapping, meaning that the region of the target sequence to which each probe hybridizes is unique (or at least non-overlapping). Probes in a set of 2 or more for a selected target sequence can be designed to hybridize adjacently to one another or to hybridize non-adjacently, with stretches of the target sequence, from one nucleotide to a hundred nucleotides or more, not complementary to any of the probes.

Accordingly, the present invention provides a method for probing a target sequence of nucleic acid molecules such as, for example, RNAs in a fixed, permeabilized cell, or a living cell, said target sequence including at least 2 non-overlapping probe binding regions of 15-100 nucleotides. The method can include the steps of immersing the cell in an excess of at least 30 nucleic acid hybridization probes, each singly labeled with a fluorescent label and each containing a nucleic acid sequence that is complementary to a different probe binding region of the target sequence, washing the cell to remove unbound probes, and detecting fluorescence from the probes.

Probes useful in this invention may be DNA, RNA or mixtures of DNA and RNA. They may include non-natural nucleotides, and they may include non-natural internucleotide linkages. Non-natural nucleotides that increase the binding affinity of probes include 2'-O-methyl ribonucleotides, for example. The lengths of probes useful in this invention can be about 15-40 nucleotides for typical DNA or RNA probes of average binding affinity. Preferred lengths of DNA probes and RNA probes are in the range of about 15-20 nucleotides, more preferably 17-25 nucleotides and even more preferably 17-22 nucleotides. In certain embodiments, the probes are about 20 nucleotides long. If means are included to increase a probe's binding affinity, the probe can be shorter, as short as seven nucleotides, as persons in the art will appreciate. A fluorophore can be attached to a probe at any position, including, without limitation, attaching a fluorophore to one end of a probe, preferably to the 3' end. The probes may be included in a hybridization solution that contains the multiple probes in excess, commonly in the range of 0.2-1 nanograms per microliter. Sufficient solution is added to cover and wet the cell so that the cell is immersed in the probe-containing solution. In another embodiment, the fluorophores can be incorporated into the probesn during automated DNA synthesis.

A single cell can be probed simultaneously for multiple RNA target sequences, either more than one target sequence of one RNA molecule, or one or more sequences of different RNA molecules. Additionally, one target sequence of an RNA molecule can be probed with more than one set of probes, wherein each set is labeled with a distinguishable fluorophore, and the fluorophores are distinguishable. For example, in probing a gene sequence, at least 2 green-labeled probes can be used to probe one portion of the gene sequence as its target sequence, and at least 2 red-labeled probes can be used to probe a different portion of the gene sequence as its target sequence. Using more than one color for each of multiple targets permits the use of color-coding schemes in highly multiplexed probing methods, according to the present invention.

Methods of the present invention may also include determining if one or more spots representing a target sequence are present. Methods according to the present invention also include counting spots of a given color corresponding to a given RNA species. When it is desired to detect more than one species of RNA, different sets of probes labeled with distinct fluorophores can be used in the same hybridization mixture. A gene expression profile for each species of RNA is constructed by counting spots of different colors.

Spots can be detected utilizing microscopic methods. It is not necessary to use a confocal microscope, as a wide-field fluorescence microscope is sufficient. To distinguish spots that positively reflect a target sequence from dim spots that may reflect background fluorescence or nonspecific binding, methods according to this invention include detection. In one embodiment, the detection comprises filtering images with a three-dimensional linear Laplacian of Gaussian filter and applying a detection threshold. If one plots the number of spots in three dimensions for all thresholds ranging from zero to the maximum pixel intensity in the filtered image, there is a wide plateau, indicative of a region in which the number of spots detected is insensitive to threshold. Thus, the method further comprises plotting the number of spots, determining the boundaries of a plateau region, and selecting the threshold preferably within that region.

In another aspect, the present invention includes sets of probes for in situ hybridization that enable detection of individual RNA molecules in cells. The probes render each molecule so intensely fluorescent that it can be seen as a fine fluorescent spot in fluorescence microscopy. A computer program can be used to identify and count all the RNA molecules in the cell from the microscopic image. In situ hybridizations performed with the sets of probes described above allow accurate and simple chromosomal structural analysis, gene expression analysis, detection of pathogens and pathogenic states such as cancer.

In yet another aspect, the invention provides a computer readable medium, including instructions for obtaining a 3-D stack of 2-D fluorescent images, filtering the 3-D stack using a 3-D filter, counting a total number of 3-D spots in the filtered 3-D stack for each of a plurality of intensity thresholds, obtaining an optimum intensity threshold representative of a plateau region in a plot of the total number of 3-D spots verses the intensity threshold at which the total number was counted, and using the total number of 3-D spots obtained at the optimum threshold as representative of a number of fluorescing particles detected in the 3-D stack.

In yet another aspect, the invention provides software implementing the thresholding algorithm as described above. In one embodiment, the thresholding is accomplished using three dimensional linear Laplacian of Gaussian filter.

The invention also provides a kit, generally comprising a set of probes, an instruction manual for performing any of the methods contemplated herein, and optionally the computer-readable media as described herein.

Chromosomal Barcoding

In another aspect of the present invention, multicolor FISH can be used to distinguish the expression of each individual gene in the ensemble by using a barcoding scheme, as depicted in FIG. 1A. This provides the ability to discriminate three fluorescent colors in the microscope, further provides the ability to distinguish up to 5 colors of RNA at the same time. In other embodiments, the palette of colors can be expanded by using combinations of 5 basic colors to yield as many as 31 effective colors. It should be appreciated that the present invention is not limited by any particular number of colors, and therefore the systems and methods of the present invention can utilize any type and number of distinguishable colors available, either as separate colors or via the combination of colors. Additionally, use of multicolor FISH allows for an increase in the number of genes uniquely targeted by using a barcoding scheme to label the chromosomes. For example, by labeling each spot using a non-repetitive sequence of colors (e.g., RRGRRBBG . . . ) and using the spatial proximity of the spots as a guide, the code allow one to "connect the dots" within the nucleus, and both uniquely identify each individual gene's location and expression level. In other embodiments, the code can be constructed in such a way as to tolerate "holes" in the code due to variable expression of the targeted genes. This method can provide expression patterns for hundreds of genes, constituting a form of "in situ microarray". In other embodiments, groups of genes organized by either location or function can be colored, depending on the biological question at hand.

Using RNAi Screening to Determine the Molecular Basis of Nuclear Structure

The system and methods of the present invention provide a compact assay for measuring chromosome structure and gene expression. In order to obtain a comprehensive view of underlying molecular mechanisms, every gene can be systematically perturbed and measure its effects by constructing an RNAi platform for analyzing high resolution FISH data. Such a platform allows for the creation of a global picture of the specific proteins responsible for the structural patterns observed in FISH data resulting from the system and methods of the present invention.

The ultimate success of an image-based RNAi screen depends on having a simple, reproducible assay and having the means to rapidly analyze the stream of data that the platform generates. The assay itself can be a version of the FISH based assay described herein, although simplified in such a way as to maximize information, while maximizing the robustness of the assay and minimizing the complexity of the analysis. For example, in one embodiment, an initial assay may include a few different regions of a chromosome labeled with different colors, providing data that is relatively simple to analyze and informative. The data acquisition itself can include an automated microscopic platform capable of meeting the requirements of high-resolution methods such as FISH. To this end, the ability of the RNA FISH method to detect subtle spatial differences in gene expression by FISH can be demonstrated in a 384-well plate format. In another embodiment, a computational platform can be included that is capable of storing and analyzing the large quantities of data that an RNAi screen generates.

While the present invention relates generally to assays involving chromosome structure, a high-throughput platform for screening coupled with single molecule microscopy can also be included. Applications for this may include the study of non-coding RNAs, which are thought to modify chromatin and thus affect chromosome structure. In one embodiment, the present invention includes an assay to measure ncRNA expression at the same time as chromosome structure, and then screen for proteins involved in mediating the response.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The following methods were used in performance of the experimental examples:

Cell Culture, Fixation, and Fluorescent In Situ Hybridization

Primary human foreskin fibroblasts (ATCC CRL 2097) or HeLa cells (gift from the lab of Phillip Sharp) were grown in Dulbeceo's modified eagle's medium with glutamax (DMEM, Life Technologies) supplemented with penicillin/streptomycin and 10% fetal bovine serum. Cells were enriched for G0/G1 phase cells through a double-thymidine block (2 μg/mL thymidine in medium) procedure and releasing for an appropriate amount of time before fixation. To fix the cells, the protocol of Raj et al. (*Nat. Meth.* 2008, 5, 877-879) was followed. Briefly, the cells were fixed using 4% formaldehyde/10% formalin in 1× phosphate buffered saline solution (PBS), followed by two rinses in 1×PBS, after which the cells were permeabilized with 70% EtOH and stored at 4° C. at least overnight.

To perform fluorescence in situ hybridization (FISH), the procedure of Raj et al. (*Nat. Meth.* 2008, 5, 877-879) was followed with some minor modifications. Prewashing was conducted with a wash buffer containing 10% formamide and 2× saline-sodium citrate (SSC), then hybridization was performed by adding the appropriate amount and type of probe (described later) in a buffer containing 10% formamide, 2×SSC and 10% dextran sulfate (W/V). Samples were hybridized overnight in a humidified chamber kept at 37° C., then washed twice for 30 minutes with wash buffer at 37° C. (adding DAPI at a concentration of 50 ng/mL in the second wash), and then imaged in 2×SSC as described below.

Figure 7:
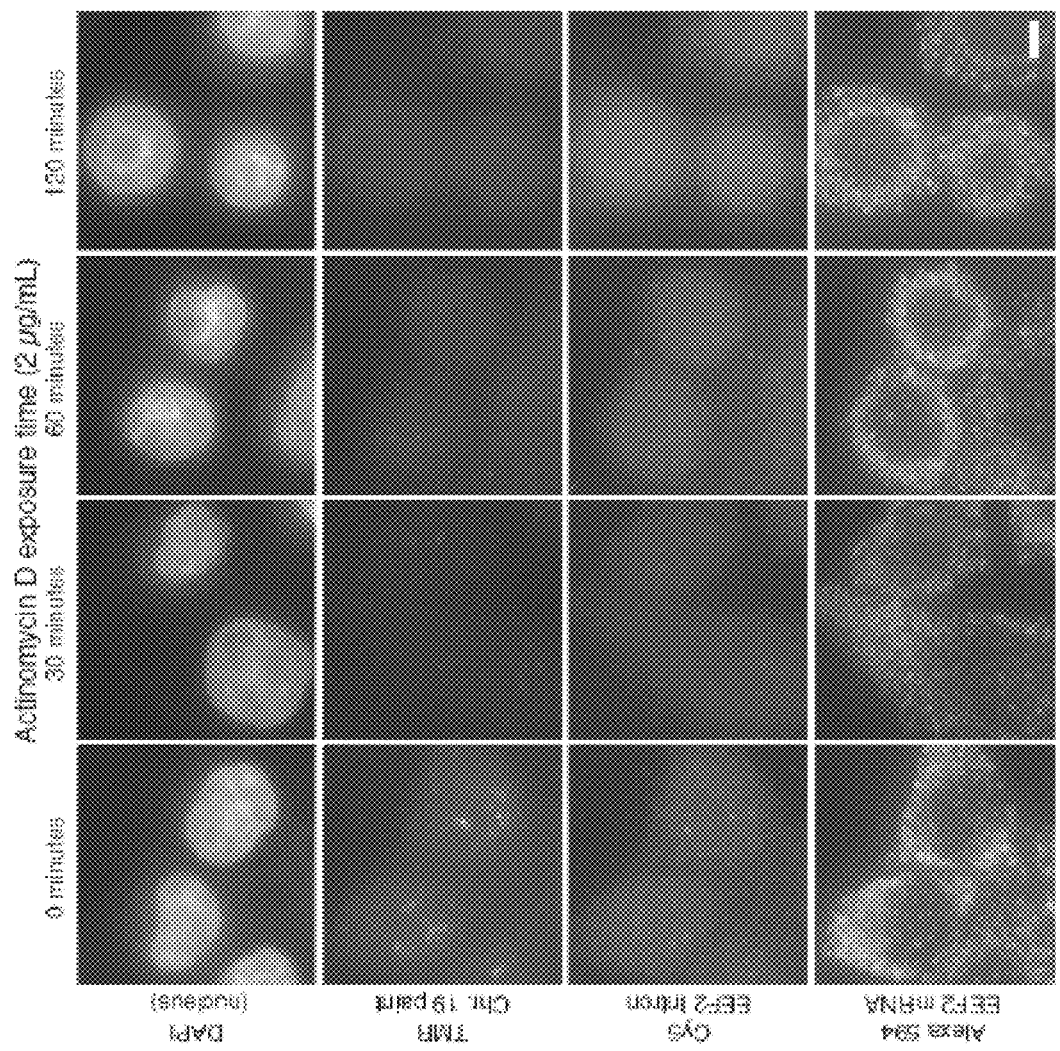
FIG. 7 depicts the rapid degradation over time of intronic RNA spots in HeLa cells through the inhibition of transcription by Actinomycin D. Virtually all of the intronic RNA disappeared or greatly diminished in intensity after 30 minutes of Actinomycin D exposure. Mature mRNA was observed at all timepoints, indicating that the cells were still alive and that the treatment did not affect the RNA itself. Altogether, the results show that the intronic RNA degrades rapidly; thus, the presence of an intronic RNA spot indicates that the targeted gene is transcriptionally active.

In the case of the experiments involving Actinomycin D, HeLa cells were incubated in 2 μg/mL of Actinomycin D (Sigma) for 0, 30, 60, and 120 minutes, after which the cells were fixed and FISH was performed as described in FIG. 7. The Actinomycin D was thoroughly mixed into the medium before being adding to avoid spatial inhomogeneity in the activity of the drug.

For the RNase experiments, the cells were fixed and permeabilized as outlined above, after which the 70% EtOH was aspirated, washed once with 1×PBS, followed by addition of 1×PBS with 10 μg/mL of RNase A (Sigma). The fixed cells were incubated at 37° C. for 30 minutes, washed with 1×PBS, and then FISH was performed as outlined above. As a control, the exact same procedure was performed on cells in a neighboring well, but RNase A was not added to the 1×PBS for the incubation.

Imaging and Image Analysis

All samples were imaged on a Nikon Ti-E inverted fluorescence microscope using a 100× Plan-Apo objective and a cooled CCD camera (Pixis 1024B from Princeton Instruments). Three-dimensional stacks of fluorescent images were sequentially acquired in 6 different fluorescent channels using filter sets for DAPI, Atto 488, Cy3, Alexa 594, Atto 647N, and Atto 700. The exposure times were roughly 2-3 seconds for most of the dyes except for DAPI (which was exposed for ~100 ms) and Atto 700 (which was exposed for ~5 seconds, due to somewhat weaker illumination on the apparatus). The spacing between consecutive planes in the stacks was 0.3 μm.

Figure 8:
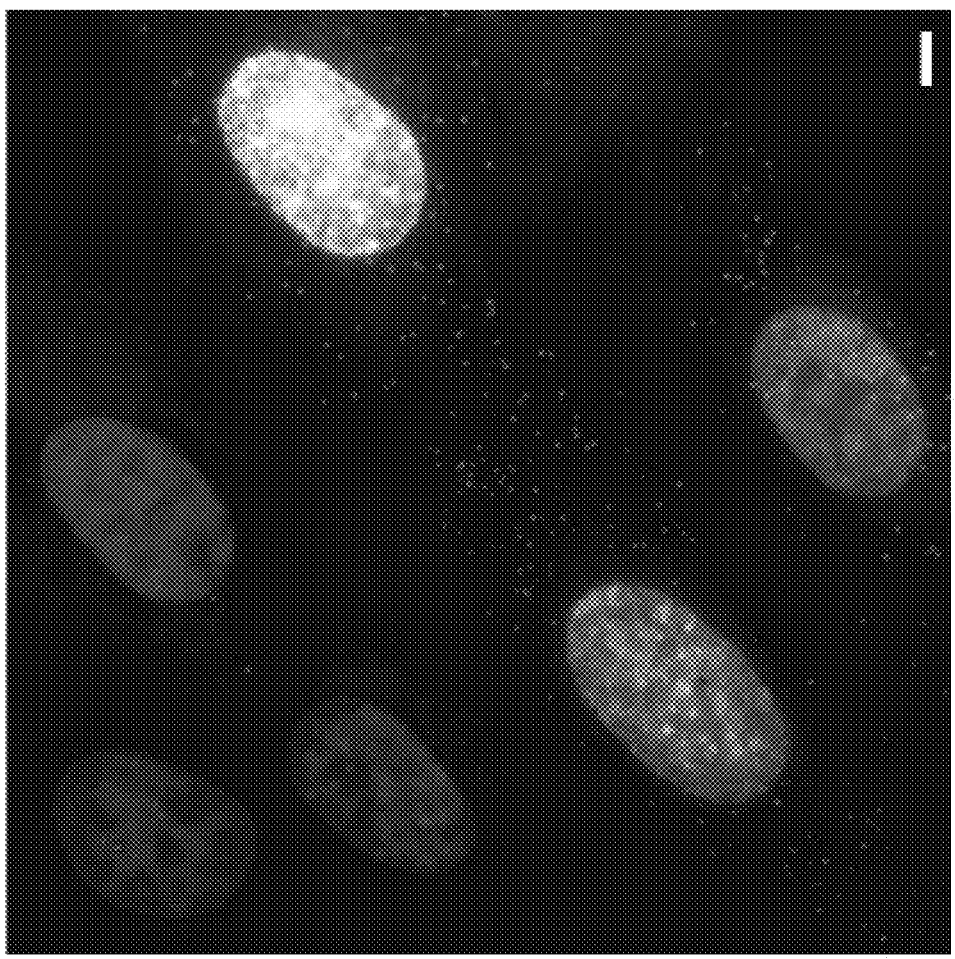
FIG. 8 depicts how labeling Cyclin A2 mRNA enables detection of cells in the S, G2, and M phases of the cell cycle. Click-iT EdU was incubated into the cells before fixation to demonstrate that high expressing cells were in the S-M phase, finding that every cell displaying Click-iT EdU signal had high levels of Cyclin A2 mRNA. This result shows that Cyclin A2 mRNA provides a strong marker for certain phases of the cell-cycle. Cells with low levels of Cyclin A2 were selected for the study as they had not undergone replication.

Once images were acquired, they were run through an image analysis pipeline made up of custom semi-automated spot recognition software written in MATLAB with the following series of steps:

1) Candidate spots were first identified in the three-dimensional image by filtering the image with a laplacian of gaussian filter, and taking the top 300 spots as candidates. In some cases, cells were chosen for analysis based on their phase in the cell-cycle. In those cases, cells were chosen that had little or no Cyclin A2 mRNAs. This approach has been validated by additional experiments (FIG. 8). 2) Each candidate was then fit to a Gaussian intensity profile, thereby giving precise estimates of the center, width, and intensity of the spot. 3) Based on histograms of the intensities and widths, a subset of the spots with qualities (uniform width, higher intensity) that were higher than background were manually selected. This is similar in spirit to the procedure described in Raj et al. (*Nat. Meth.* 2008, 5, 877-879), in which a threshold was chosen to separate legitimate RNA spots from background spots. In this case, spots that may have been background were included because the multicolor scheme for spot assignment provided another means by which to discard background spots. 4) Once the spots were selected, software was run that found the fiducial markers (in this case, probes in all 5 RNA colors targeting SuZ12 mRNA). In this manner, the displacements between different fluorescence channels in each cell could be measured individually. These shifts were then applied to align the computationally identified spots between the different fluorescence channels. 5) After alignment, software was run which looked for colocalized spots corresponding to the particular pseudocoloring scheme chosen for the targeted introns. It was estimated that the software is roughly 75% accurate in assigning colocalized spots to particular genes at this stage. 6) A manual correction process was carried out in which mistakes the software made in identifying spots were corrected. Common issues included failure to detect dim (but clearly present) signals in one of the fluorescent channels and resolving two spatially close fluorescent spots that the laplacian of gaussian filtering and candidate identification steps had labeled as a single spot. 7) Once the labeled introns of the gene loci had been correctly annotated, cells were examined manually to separate out individual chromosomes. Cells were discarded in which the chromosomes overlapped, which made it difficult to assign particular spots to particular chromosomes.

Karyotyping of HeLa Cells

G-band analysis (karyotyping) was performed on metaphase spreads of the HeLa cells following standard procedures. This indicated that the cells contained two intact copies of chromosome 19 and a full third copy of chromosome 19, which was split into two fragments and fused to other chromosomes. One fragment included the first half of the chromosome 19 p-arm and was fused to a large portion of chromosome 6. The second fragment was the remaining portion of chromosome 19 (half the p-arm through the centromere and entire q-arm), which was fused to the q-arm of chromosome 13. In order to conclusively demonstrate that chromosome 19 was split in this particular way, a DNA FISH analysis was performed on the same metaphase spreads on which the G-band analysis was performed. Probes targeting loci within the 19p13 and 19q13 regions on chromosome 19 were used, each labeled with a different fluorophore (Abbott Molecular). The results confirmed the results of the G-band analysis. This analysis was performed on 10 cells, each of which showed the same genetic abnormalities, indicating that the cells do not vary to a large degree in this particular characteristic from cell to cell.

Click-iT EdU Analysis of Cell Cycle Progression

In order to demonstrate that Cyclin A2 mRNA was an accurate marker of position in the cell cycle, the Click-iT EdU Alexa Fluor 594 Imaging kit (Invitrogen) was used, which incorporated a targetable chemical into newly replicated DNA. In this case, cells were incubated with the 10 µM Click-iT EdU reagent for 5 minutes before the cells were fixed. The FISH protocol was performed on these cells using a Cyclin A2 mRNA Cy3 probe, and after hybridization and wash steps, the instructions provided with the kit were followed for fluorescently labeling the incorporated EdU.

Culturing of Drosophila S2 Cells

Drosophila S2 cells were obtained from ATCC and grown in Schneider's complete medium supplemented with 10% heat-inactivated fetal bovine serum, 2 mM L-glutamine and penicillin/streptomycin. The cells were subcultured by diluting 10-fold in fresh medium once every 3-4 days once the culture had reached confluency.

In experiments where MtnA expression was induced, copper sulfate was added to a final concentration of 1 mM to the cell medium and the cells were incubated for 5 hours before live imaging.

Design of Probes 20 base oligonucleotide probes were designed against introns using custom FISH design software (http://www.biosearchtech.com/stellarisdesigner/). Where possible, the design of 16 oligonucleotides targeting the first intron of the gene was attempted. The oligonucleotides were ordered from Biosearch Technologies (Novato, Calif.), who synthesized the oligonucleotides with amine groups attached to the 3' end. These 3' ends were coupled to various organic dyes (including Atto 488 (Atto-Tee), Cy3 (GE), Alexa 594 (Invitrogen), Atto 647N (Atto-Tec), and Atto 700 (Atto-Tec)) as indicated in the text and in Table 1. The probes were purified by HPLC as described in Raj et al. (*Nat. Meth.* 2008, 5, 877-879).

Probes Used for Live Imaging

All the probes used in the study were 20-mer single-stranded oligonucleotides synthesized with 2'O-methyl-modified nucleic acid backbones. All oligonucleotides have the tetramethylrhodamine (TAMRA) dye covalently attached to the 3' end.

The specific sequences used for the oligonucleotides targeting roX2 RNA were (5' to 3') and are listed in Table 1. Also listed in Table 1 are the sequences for the oligonucleotides used to target the MtnA gene were (5' to 3')

Probes Used for FISH

FISH was performed using probes against the same target RNA as the live imaging probes, but with the oligonucleotides for FISH targeting different sequences within the target RNA to avoid competition between the probes. All of the oligonucleotides used for FISH were single stranded DNA oligonucleotides with a Cy5 fluorescent molecule covalently attached to the 3' end (Cy5 was chosen because it is spectrally distinct from TAMRA, which was used for the live imaging probes). The sequences for the oligonucleotides used to target the roX2 RNA for FISH colocalization analysis are (5' to 3') and listed in Table 1.

The sequences for the oligonucleotides used to target the MtnA mRNA for FISH colocalization analysis are (5' to 3') and provided in Table 1.

Delivery of Live Imaging Oligonucleotides

The live imaging oligonucleotides specific to the target of interest were introduced into live Drosophila S2 cells via electroporation using the Neon transfection system (Invitrogen/Life Technologies). The live imaging oligonucleotide pool was added directly to the buffer containing the cells at a concentration of 0.8 uM per oligonucleotide, followed by microporation by essentially following the manufacturers instructions, using 4 pulses with width 5 ms and a voltage of 2000 V. The cells were microporated and then settled onto chambered coverslips coated with concanavalin A to promote cell adhesion. Imaging commenced after one hour.

Fluorescence In Situ Hybridization (FISH) Following Live Imaging

In these experiments, the live imaging probes were delivered as described above. After 6 hours, the cells were fixed following the protocol of Raj et al. (*Nat. Meth.* 2008, 5, 877-879).; briefly, the cells were fixed in 4% formaldehyde in 1× phosphate buffered saline (PBS) solution, washed twice in 1×PBS, and then permeabilized in 70% EtOH. After fixation, hybridization was carried out, adding roughly 0.2 ng/µl (total oligonucleotide concentration) of the FISH probe to hybridization solution, hybridizing for 1 hour and then washing twice with a wash buffer containing 2× saline-sodium citrate (SSC) and 10% formamide, adding DAPI to the second wash followed by washing. 2×SSC was added to the samples, which were then imaged as described below.

Live RNA Imaging

All samples were imaged on a Leica DMI6000B inverted fluorescence microscope using a 100× Plan-Apo objective and a cooled CCD camera (Pixis 1024B from Princeton Instruments). A filter set optimized for the TAMRA fluorophore was used, Exposure times of 2 s were used and the number of exposures was limited to 10 to avoid phototoxicity. In some cases, a series of optical sections corresponding to different focal planes (a z-stack) was acquired in order to fully image all parts of the cell; with 0.3 µM spacing between optical sections.

In the experiments where the live imaging probe and the FISH signal targeting the same RNA were simultaneously imaged, sequential z-stacks were acquired using filters that can distinguish TAMRA (live imaging probe) and Cy5 (FISH probe), thereby allowing colocalization of the signals,

TABLE 1

| Probe | Probe Sequence | Organic Dye | Sequence Number |
|---|---|---|---|
| DHPS_int_1 | ctagtaccgcgttggttcta | ATTO647N | SEQ ID NO: 1 |
| DHPS_int_2 | cagagtgcaaaatcccttc | ATTO700 | SEQ ID NO: 2 |
| DHPS_int_3 | taccgtaccagcatgtaact | Alexa594 | SEQ ID NO: 3 |
| DHPS_int_4 | cacaccaagaatcagtcctc | ATTO647N | SEQ ID NO: 4 |
| DHPS_int_5 | gcccattccagaaagcttta | ATTO700 | SEQ ID NO: 5 |
| DHPS_int_6 | cctcccatatcctcccttaa | Alexa594 | SEQ ID NO: 6 |

TABLE 1-continued

| Probe | Probe Sequence | Organic Dye | Sequence Number |
|---|---|---|---|
| DHPS_int_7 | tctaaattcaagaaccgccc | ATTO647N | SEQ ID NO: 7 |
| DHPS_int_8 | atctcctttcagatccggtc | ATTO700 | SEQ ID NO: 8 |
| DHPS_int_9 | ggctccagaaacagatttca | Alexa594 | SEQ ID NO: 9 |
| DHPS_int_10 | taaatcccagactcaggact | ATTO647N | SEQ ID NO: 10 |
| DHPS_int_11 | aagggccaagtcaagttaag | ATTO700 | SEQ ID NO: 11 |
| DHPS_int_12 | ataactgcattgcccattga | Alexa594 | SEQ ID NO: 12 |
| DHPS_int_13 | tgactcttatgagggagctc | ATTO647N | SEQ ID NO: 13 |
| DHPS_int_14 | agtgaatttggcccaagaag | ATTO700 | SEQ ID NO: 14 |
| DHPS_int_15 | cagagatagtctgggaggag | Alexa594 | SEQ ID NO: 15 |
| DHPS_int_16 | gctaagtgttgcctctactg | ATTO647N | SEQ ID NO: 16 |
| DNMT1_int_1 | gaatccacggtccattttgg | ATTO700 | SEQ ID NO: 17 |
| DNMT1_int_2 | cttgctgtatttggggatca | Cy3 | SEQ ID NO: 18 |
| DNMT1_int_3 | catcgagatgcacagctttg | Alexa594 | SEQ ID NO: 19 |
| DNMT1_int_4 | gtgacatccgtctctggagg | ATTO700 | SEQ ID NO: 20 |
| DNMT1_int_5 | aaggagcaagaaccacacag | Cy3 | SEQ ID NO: 21 |
| DNMT1_int_6 | aatgcacggttaaagttcct | Alexa594 | SEQ ID NO: 22 |
| DNMT1_int_7 | caggcacagatttacaggaa | ATTO700 | SEQ ID NO: 23 |
| DNMT1_int_8 | agccagttctcattagcaag | Cy3 | SEQ ID NO: 24 |
| DNMT1_int_9 | acacactaaagaacacaccc | Alexa594 | SEQ ID NO: 25 |
| DNMT1_int_10 | gatccttgtgcacggaagtt | ATTO700 | SEQ ID NO: 26 |
| DNMT1_int_11 | aatgaactgatggcgttcat | Cy3 | SEQ ID NO: 27 |
| DNMT1_int_12 | cacacctcacttgaacaagt | Alexa594 | SEQ ID NO: 28 |
| DNMT1_int_13 | gtgagggttcctctgactca | ATTO700 | SEQ ID NO: 29 |
| DNMT1_int_14 | tttcacaaatccagctggaa | Cy3 | SEQ ID NO: 30 |
| DNMT1_int_15 | cccaaagacccaaatcagaa | Alexa594 | SEQ ID NO: 31 |
| DNMT1_int_16 | ggggttgaaccaaatatcca | ATTO700 | SEQ ID NO: 32 |
| EEF2_int_1 | attactacgcctgccacatc | Cy3 | SEQ ID NO: 33 |
| EEF2_int_2 | cggcagaaaatcgatctcaa | ATTO647N | SEQ ID NO: 34 |
| EEF2_int_3 | ctttgctcgttctgccattc | Cy3 | SEQ ID NO: 35 |
| EEF2_int_4 | ctttgtacatctgggagtca | ATTO647N | SEQ ID NO: 36 |
| EEF2_int_5 | acacctcgtgtctcaataag | Cy3 | SEQ ID NO: 37 |
| EEF2_int_6 | cgagcaagaagcttcatcat | ATTO647N | SEQ ID NO: 38 |
| EEF2_int_7 | acgtaagggatgaatcctct | Cy3 | SEQ ID NO: 39 |
| EEF2_int_8 | actaaagtctcatttggggc | ATTO647N | SEQ ID NO: 40 |
| EEF2_int_9 | tgagtgtcaacagatttcct | Cy3 | SEQ ID NO: 41 |
| EEF2_int_10 | ggaaccaccgttaataggtg | ATTO647N | SEQ ID NO: 42 |
| EEF2_int_11 | gaatcttgccagcctaacac | Cy3 | SEQ ID NO: 43 |
| EEF2_int_12 | gttcagtccaaacgaaccag | ATTO647N | SEQ ID NO: 44 |
| EEF2_int_13 | ctcgtgatttccaggaacac | Cy3 | SEQ ID NO: 45 |

TABLE 1-continued

| Probe | Probe Sequence | Organic Dye | Sequence Number |
|---|---|---|---|
| EEF2_int_14 | gaaagagacgttgccaagtc | ATTO647N | SEQ ID NO: 46 |
| EEF2_int_15 | ggactgaacctcactcattc | Cy3 | SEQ ID NO: 47 |
| EEF2_int_16 | agatattgtaggagtggggg | ATTO647N | SEQ ID NO: 48 |
| EGLN2_int_1 | aactgcctaaaccttctgtg | ATTO700 | SEQ ID NO: 49 |
| EGLN2_int_2 | gtccccacaagtaagcatac | ATTO647N | SEQ ID NO: 50 |
| EGLN2_int_3 | atcaggtgcacacattaagg | ATTO700 | SEQ ID NO: 51 |
| EGLN2_int_4 | aaagtcaagaaccactgtgg | ATTO647N | SEQ ID NO: 52 |
| EGLN2_int_5 | gaatgtcagcagctctcatg | ATTO700 | SEQ ID NO: 53 |
| EGLN2_int_6 | gacagacagcaacagagaac | ATTO647N | SEQ ID NO: 54 |
| EGLN2_int_7 | gatggactagaaacatgggc | ATTO700 | SEQ ID NO: 55 |
| EGLN2_int_8 | ccacccatgaagacaatgat | ATTO647N | SEQ ID NO: 56 |
| EGLN2_int_9 | cagaagcagaacccaagatg | ATTO700 | SEQ ID NO: 57 |
| EGLN2_int_10 | gctcagctatcaagtaacgg | ATTO647N | SEQ ID NO: 58 |
| EGLN2_int_11 | gtattccgtggatcagcaaa | ATTO700 | SEQ ID NO: 59 |
| EGLN2_int_12 | gtccccaaccacatagaaag | ATTO647N | SEQ ID NO: 60 |
| EGLN2_int_13 | tccttacttccctaggacaa | ATTO700 | SEQ ID NO: 61 |
| EGLN2_int_14 | cccatctaaaagcgggaaag | ATTO647N | SEQ ID NO: 62 |
| EGLN2_int_15 | gagtacaggagagagtccag | ATTO700 | SEQ ID NO: 63 |
| EGLN2_int_16 | cagaacgactaagaagcacg | ATTO647N | SEQ ID NO: 64 |
| EIF3K_int_1 | gattctctcgcttctaggcc | ATTO700 | SEQ ID NO: 65 |
| EIF3K_int_2 | cgaagagactgagtggtacc | ATTO488 | SEQ ID NO: 66 |
| EIF3K_int_3 | aaggaaaccttaaggcaatt | ATTO700 | SEQ ID NO: 67 |
| EIF3K_int_4 | atgtccacctgaacactctg | ATTO488 | SEQ ID NO: 68 |
| EIF3K_int_5 | tcctgaatgtctctgctact | ATTO700 | SEQ ID NO: 69 |
| EIF3K_int_6 | tcagtcactgcagcttgtac | ATTO488 | SEQ ID NO: 70 |
| EIF3K_int_7 | taggatgcctcctcaacctc | ATTO700 | SEQ ID NO: 71 |
| EIF3K_int_8 | aagctctaaactccactgga | ATTO488 | SEQ ID NO: 72 |
| EIF3K_int_9 | ttcttatcccagacctctcg | ATTO700 | SEQ ID NO: 73 |
| EIF3K_int_10 | gctctatccaggtagtgaat | ATTO488 | SEQ ID NO: 74 |
| EIF3K_int_11 | cagccaccttatggagcaag | ATTO700 | SEQ ID NO: 75 |
| EIF3K_int_12 | agacagagagctagacactt | ATTO488 | SEQ ID NO: 76 |
| EIF3K_int_13 | ctagttgctgcaatgggagt | ATTO700 | SEQ ID NO: 77 |
| EIF3K_int_14 | gctgcattgttcaggatact | ATTO488 | SEQ ID NO: 78 |
| EIF3K_int_15 | ctagtcttgcacaccaagag | ATTO700 | SEQ ID NO: 79 |
| EIF3K_int_16 | ctcctgtcccaacttccttg | ATTO488 | SEQ ID NO: 80 |
| FBL_int_1 | gacctgctggaatcagaatc | ATTO488 | SEQ ID NO: 81 |
| FBL_int_2 | cctattagacggcctcaatg | ATTO700 | SEQ ID NO: 82 |
| FBL_int_3 | ctcctgcccaatatccaaaa | Alexa594 | SEQ ID NO: 83 |
| FBL_int_4 | cagatgcctgaatccaaact | ATTO488 | SEQ ID NO: 84 |

TABLE 1-continued

| Probe | Probe Sequence | Organic Dye | Sequence Number |
|---|---|---|---|
| FBL_int_5 | caagcctgattcccaaaaca | ATTO700 | SEQ ID NO: 85 |
| FBL_int_6 | ggtggaaatcttaatccca | Alexa594 | SEQ ID NO: 86 |
| FBL_int_7 | cgagcttgttaagtctcgtc | ATTO488 | SEQ ID NO: 87 |
| FBL_int_8 | gagtggtttcagcagaatct | ATTO700 | SEQ ID NO: 88 |
| FBL_int_9 | accaccgagaaggattctaa | Alexa594 | SEQ ID NO: 89 |
| FBL_int_10 | ttctcacacagatgagtgcg | ATTO488 | SEQ ID NO: 90 |
| FBL_int_11 | taggaaaacagacccttttgg | ATTO700 | SEQ ID NO: 91 |
| FBL_int_12 | tcaagagatccccaaacacg | Alexa594 | SEQ ID NO: 92 |
| FBL_int_13 | atcacagaccagaatgcctg | ATTO488 | SEQ ID NO: 93 |
| FBL_int_14 | cattctaccacacatggagg | ATTO700 | SEQ ID NO: 94 |
| FBL_int_15 | gagctaacacctgacaactt | Alexa594 | SEQ ID NO: 95 |
| FBL_int_16 | ctcactcaggctaaaatcct | ATTO488 | SEQ ID NO: 96 |
| ILF3_int_1 | atgctttggaaaaggctaca | ATTO488 | SEQ ID NO: 97 |
| ILF3_int_2 | actgacttcgttcctacact | ATTO700 | SEQ ID NO: 98 |
| ILF3_int_3 | ggacaagcaaactgaaaagc | ATTO647N | SEQ ID NO: 99 |
| ILF3_int_4 | gagcacaactgaagaaccaa | ATTO488 | SEQ ID NO: 100 |
| ILF3_int_5 | tatcgctcgtgtgtaaaagc | ATTO700 | SEQ ID NO: 101 |
| ILF3_int_6 | tgcacaattcagaatgatgc | ATTO647N | SEQ ID NO: 102 |
| ILF3_int_7 | agcccaacgttcatctttta | ATTO488 | SEQ ID NO: 103 |
| ILF3_int_8 | agaggctggagtttcttaga | ATTO700 | SEQ ID NO: 104 |
| ILF3_int_9 | aattcagtctgaccacaacc | ATTO647N | SEQ ID NO: 105 |
| ILF3_int_10 | atcctcaatcagcatgccta | ATTO488 | SEQ ID NO: 106 |
| ILF3_int_11 | tggttgtcacctactgagaa | ATTO700 | SEQ ID NO: 107 |
| ILF3_int_12 | cacagaatctctgtggcttg | ATTO647N | SEQ ID NO: 108 |
| ILF3_int_13 | cttatgacccctgcagtcag | ATTO488 | SEQ ID NO: 109 |
| ILF3_int_14 | acgtgaagtttatgcccaat | ATTO700 | SEQ ID NO: 110 |
| ILF3_int_15 | tctatctagccatccatcca | ATTO647N | SEQ ID NO: 111 |
| ILF3_int_16 | gctttggatccaatggaaga | ATTO488 | SEQ ID NO: 112 |
| MARK4_int_1 | gaccttgaagaagccagaaa | ATTO488 | SEQ ID NO: 113 |
| MARK4_int_2 | cctgaagctgagaagttgat | Cy3 | SEQ ID NO: 114 |
| MARK4_int_3 | caagggaaaagggcttaaa | ATTO647N | SEQ ID NO: 115 |
| MARK4_int_4 | gagaaagcttccagcagatt | ATTO488 | SEQ ID NO: 116 |
| MARK4_int_5 | aggtcaaggggtctagaaat | Cy3 | SEQ ID NO: 117 |
| MARK4_int_6 | agatgaataaaggctgagcc | ATTO647N | SEQ ID NO: 118 |
| MARK4_int_7 | ctggaagtatggggtaggaa | ATTO488 | SEQ ID NO: 119 |
| MARK4_int_8 | tcctaggaatcagagaaggg | Cy3 | SEQ ID NO: 120 |
| MARK4_int_9 | ggaatggtggaaagtgacaa | ATTO647N | SEQ ID NO: 121 |
| MARK4_int_10 | tgatcagagacacaggagat | ATTO488 | SEQ ID NO: 122 |
| MARK4_int_11 | gcaggtctttggaagtgatc | Cy3 | SEQ ID NO: 123 |

TABLE 1-continued

| Probe | Probe Sequence | Organic Dye | Sequence Number |
|---|---|---|---|
| MARK4_int_12 | tggggagaagtctaggattg | ATTO647N | SEQ ID NO: 124 |
| MARK4_int_13 | gatctgcaagatgaggaagg | ATTO488 | SEQ ID NO: 125 |
| MARK4_int_14 | actccaaattggagttctgg | Cy3 | SEQ ID NO: 126 |
| MARK4_int_15 | attgtagtgaccaaggaaca | ATTO647N | SEQ ID NO: 127 |
| MARK4_int_16 | ctgaatcgagtaagccttgg | ATTO488 | SEQ ID NO: 128 |
| PPP2R1A_int_1 | caaccggggagataagagac | Cy3 | SEQ ID NO: 129 |
| PPP2R1A_int_2 | cctacttggagcaagtcatg | Alexa594 | SEQ ID NO: 130 |
| PPP2R1A_int_3 | aattaggatggcaggccttc | Cy3 | SEQ ID NO: 131 |
| PPP2R1A_int_4 | aaaatgagaggcggaggaag | Alexa594 | SEQ ID NO: 132 |
| PPP2R1A_int_5 | cgtcctcttaggacacctaa | Cy3 | SEQ ID NO: 133 |
| PPP2R1A_int_6 | gctcctaaacttggctagtc | Alexa594 | SEQ ID NO: 134 |
| PPP2R1A_int_7 | tatcctggtcaatgggagga | Cy3 | SEQ ID NO: 135 |
| PPP2R1A_int_8 | gcttagcaaatccctcaacc | Alexa594 | SEQ ID NO: 136 |
| PPP2R1A_int_9 | catcccataaccaggaatgt | Cy3 | SEQ ID NO: 137 |
| PPP2R1A_int_10 | cctctttaatcaccactccc | Alexa594 | SEQ ID NO: 138 |
| PPP2R1A_int_11 | aacagacctaaagggaggat | Cy3 | SEQ ID NO: 139 |
| PPP2R1A_int_12 | gtttggcaggttacccagtg | Alexa594 | SEQ ID NO: 140 |
| PPP2R1A_int_13 | tataccaggaacctaggagg | Cy3 | SEQ ID NO: 141 |
| PPP2R1A_int_14 | tccccagcatcatatctcat | Alexa594 | SEQ ID NO: 142 |
| PPP2R1A_int_15 | tatagcaactggtgtctcca | Cy3 | SEQ ID NO: 143 |
| PPP2R1A_int_16 | cctgtttcacatctggatcc | Alexa594 | SEQ ID NO: 144 |
| PTBP1_int_1 | gaatgcgaaacatctccagc | Cy3 | SEQ ID NO: 145 |
| PTBP1_int_2 | aaacttctcaggaaaacgga | ATTO700 | SEQ ID NO: 146 |
| PTBP1_int_3 | ctcttctgacaccacagact | Cy3 | SEQ ID NO: 147 |
| PTBP1_int_4 | gggggaaggtggatagaaag | ATTO700 | SEQ ID NO: 148 |
| PTBP1_int_5 | gaacacagcctcagttactg | Cy3 | SEQ ID NO: 149 |
| PTBP1_int_6 | ctgaaactggcaaactcaca | ATTO700 | SEQ ID NO: 150 |
| PTBP1_int_7 | gtgctttccagtaagttgga | Cy3 | SEQ ID NO: 151 |
| PTBP1_int_8 | cacgttccaagacaaagaca | ATTO700 | SEQ ID NO: 152 |
| PTBP1_int_9 | ccacttgactgcaacttgaa | Cy3 | SEQ ID NO: 153 |
| PTBP1_int_10 | cgctagagaaagctcagaag | ATTO700 | SEQ ID NO: 154 |
| PTBP1_int_11 | cggagaagcaaagtgagaag | Cy3 | SEQ ID NO: 155 |
| PTBP1_int_12 | aactccagattccagaccaa | ATTO700 | SEQ ID NO: 156 |
| PTBP1_int_13 | tgacagcaagaaccgaagag | Cy3 | SEQ ID NO: 157 |
| PTBP1_int_14 | taggctggattctatccagg | ATTO700 | SEQ ID NO: 158 |
| PTBP1_int_15 | tcaaccagtaaatgcccatc | Cy3 | SEQ ID NO: 159 |
| PTBP1_int_16 | cccttttcctcacatgctgag | ATTO700 | SEQ ID NO: 160 |
| RPL18A_int_1 | gttgggtgcaacaagagaag | ATTO488 | SEQ ID NO: 161 |
| RPL18A_int_2 | ctatgctgcgcgacttattc | ATTO647N | SEQ ID NO: 162 |

TABLE 1-continued

| Probe | Probe Sequence | Organic Dye | Sequence Number |
|---|---|---|---|
| RPL18A_int_3 | tttcatctgcttctcacagc | ATTO488 | SEQ ID NO: 163 |
| RPL18A_int_4 | tatgtaccacagcgttaagc | ATTO647N | SEQ ID NO: 164 |
| RPL18A_int_5 | ccatagagccgtttgattct | ATTO488 | SEQ ID NO: 165 |
| RPL18A_int_6 | agtccaggttctcctatctc | ATTO647N | SEQ ID NO: 166 |
| RPL18A_int_7 | agctggagatctggacataa | ATTO488 | SEQ ID NO: 167 |
| RPL18A_int_8 | cctttgacagcaaggaaacc | ATTO647N | SEQ ID NO: 168 |
| RPL18A_int_9 | gttcaggaagggaacaatgg | ATTO488 | SEQ ID NO: 169 |
| RPL18A_int_10 | ttttactgtgaacctgaccc | ATTO647N | SEQ ID NO: 170 |
| RPL18A_int_11 | aaaccacctctgaaactgac | ATTO488 | SEQ ID NO: 171 |
| RPL18A_int_12 | aatctttggtcaagtccagg | ATTO647N | SEQ ID NO: 172 |
| RPL18A_int_13 | ggtttacagatgcagaggtg | ATTO488 | SEQ ID NO: 173 |
| RPL18A_int_14 | aactgcaatccaaacgtttg | ATTO647N | SEQ ID NO: 174 |
| RPL18A_int_15 | agaactaggacaagacctca | ATTO488 | SEQ ID NO: 175 |
| RPL18A_int_16 | catcttctttcaccctgagg | ATTO647N | SEQ ID NO: 176 |
| RPS19_int_1 | tctggatcgcactaacagag | Cy3 | SEQ ID NO: 177 |
| RPS19_int_2 | catcctaaaccgtggtaccc | ATTO488 | SEQ ID NO: 178 |
| RPS19_int_3 | ggagaaagtcaagcatgtga | Cy3 | SEQ ID NO: 179 |
| RPS19_int_4 | tttgaacctcagtccccaaa | ATTO488 | SEQ ID NO: 180 |
| RPS19_int_5 | gtacaaagagaggctggaac | Cy3 | SEQ ID NO: 181 |
| RPS19_int_6 | cctcaacacaactatgctgt | ATTO488 | SEQ ID NO: 182 |
| RPS19_int_7 | ctaccccatatcccaaatgc | Cy3 | SEQ ID NO: 183 |
| RPS19_int_8 | cacgattcagtcatctccac | ATTO488 | SEQ ID NO: 184 |
| RPS19_int_9 | aagaccaaaacagtgggaaa | Cy3 | SEQ ID NO: 185 |
| RPS19_int_10 | gaagtatggtttgtgccagg | ATTO488 | SEQ ID NO: 186 |
| RPS19_int_11 | gaaagagctcagaggagaca | Cy3 | SEQ ID NO: 187 |
| RPS19_int_12 | caagtggtgacacaaccaag | ATTO488 | SEQ ID NO: 188 |
| RPS19_int_13 | tcgaatgtcacatcacacaa | Cy3 | SEQ ID NO: 189 |
| RPS19_int_14 | aaaaacttggagtaccaagt | ATTO488 | SEQ ID NO: 190 |
| RPS19_int_15 | ttcatctgtctctggtttcc | Cy3 | SEQ ID NO: 191 |
| RPS19_int_16 | aaaccacctgtaagcaaaat | ATTO488 | SEQ ID NO: 192 |
| RPS9_int_1 | gcttactcatggaaactcgg | ATTO488 | SEQ ID NO: 193 |
| RPS9_int_2 | tcatagtcagtatctgcccc | Alexa594 | SEQ ID NO: 194 |
| RPS9_int_3 | atccgatctcgcgagaataa | ATTO488 | SEQ ID NO: 195 |
| RPS9_int_4 | gagagaagtgtgagcgtaag | Alexa594 | SEQ ID NO: 196 |
| RPS9_int_5 | atagagtacatgggcacctt | ATTO488 | SEQ ID NO: 197 |
| RPS9_int_6 | gtaccaaatttaggggacgg | Alexa594 | SEQ ID NO: 198 |
| RPS9_int_7 | tggaatcacaaaaccttcct | ATTO488 | SEQ ID NO: 199 |
| RPS9_int_8 | cgtactggcacaacaactag | Alexa594 | SEQ ID NO: 200 |
| RPS9_int_9 | gggagaatgaacctcacaag | ATTO488 | SEQ ID NO: 201 |

TABLE 1-continued

| Probe | Probe Sequence | Organic Dye | Sequence Number |
|---|---|---|---|
| RPS9_int_10 | gacacaactctcatcactgg | Alexa594 | SEQ ID NO: 202 |
| RPS9_int_11 | aaggctggttccatttatcc | ATTO488 | SEQ ID NO: 203 |
| RPS9_int_12 | tttcctacttcacaagtgcc | Alexa594 | SEQ ID NO: 204 |
| RPS9_int_13 | acctaagaaacagggcaaag | ATTO488 | SEQ ID NO: 205 |
| RPS9_int_14 | aggcctatctttagctctgg | Alexa594 | SEQ ID NO: 206 |
| RPS9_int_15 | gcccagaaattccacttcat | ATTO488 | SEQ ID NO: 207 |
| RPS9_int_16 | aaccctgttatcaccatcac | Alexa594 | SEQ ID NO: 208 |
| SLC1A5_int_1 | gaggactcactgagcgaaag | ATTO700 | SEQ ID NO: 209 |
| SLC1A5_int_2 | tgcattttttccaggaactaa | Cy3 | SEQ ID NO: 210 |
| SLC1A5_int_3 | tgagcccgtattctcattga | ATTO488 | SEQ ID NO: 211 |
| SLC1A5_int_4 | aattaaaactcacaggaggc | ATTO700 | SEQ ID NO: 212 |
| SLC1A5_int_5 | atgccaagctaacaatgctc | Cy3 | SEQ ID NO: 213 |
| SLC1A5_int_6 | gtgtccatcgttaccagggc | ATTO488 | SEQ ID NO: 214 |
| SLC1A5_int_7 | taggcaaagaggtagagccc | ATTO700 | SEQ ID NO: 215 |
| SLC1A5_int_8 | aaggactgcagagtgtcaat | Cy3 | SEQ ID NO: 216 |
| SLC1A5_int_9 | acaaagtagagacctatcca | ATTO488 | SEQ ID NO: 217 |
| SLC1A5_int_10 | cacctggggtgggaaaagag | ATTO700 | SEQ ID NO: 218 |
| SLC1A5_int_11 | gagagggcagcatggaatgg | Cy3 | SEQ ID NO: 219 |
| SLC1A5_int_12 | cagtttgagcaggttgaggg | ATTO488 | SEQ ID NO: 220 |
| SLC1A5_int_13 | aaaggacactcagtctacct | ATTO700 | SEQ ID NO: 221 |
| SLC1A5_int_14 | ctgtgggcaaggaacagatc | Cy3 | SEQ ID NO: 222 |
| SLC1A5_int_15 | caaacagaatgccccgcacc | ATTO488 | SEQ ID NO: 223 |
| SLC1A5_int_16 | gtgaatagagggtgccccat | ATTO700 | SEQ ID NO: 224 |
| SUPT5H_int_1 | tctcttgagacaatctggga | ATTO647N | SEQ ID NO: 225 |
| SUPT5H_int_2 | cctttgcttgacttcgactt | Cy3 | SEQ ID NO: 226 |
| SUPT5H_int_3 | tgttatctcactggacctga | Alexa594 | SEQ ID NO: 227 |
| SUPT5H_int_4 | cttttttttagggggtggtgg | ATTO647N | SEQ ID NO: 228 |
| SUPT5H_int_5 | ctctgatccaaccaaagtgg | Cy3 | SEQ ID NO: 229 |
| SUPT5H_int_6 | ggaacacagtagtagatgca | Alexa594 | SEQ ID NO: 230 |
| SUPT5H_int_7 | accagacacctgagaagtaa | ATTO647N | SEQ ID NO: 231 |
| SUPT5H_int_8 | ctggtttgtgattgctacct | Cy3 | SEQ ID NO: 232 |
| SUPT5H_int_9 | gtgcatcaaacaagggatct | Alexa594 | SEQ ID NO: 233 |
| SUPT5H_int_10 | ggcaactaacatatcctggg | ATTO647N | SEQ ID NO: 234 |
| SUPT5H_int_11 | acacagccacatgaaatctt | Cy3 | SEQ ID NO: 235 |
| SUPT5H_int_12 | gcactctccatctaccaaac | Alexa594 | SEQ ID NO: 236 |
| SUPT5H_int_13 | taagtgactgggacaagtca | ATTO647N | SEQ ID NO: 237 |
| SUPT5H_int_14 | ggcaatcaaatgtccacaga | Cy3 | SEQ ID NO: 238 |
| SUPT5H_int_15 | cactctccaaaggtcacaat | Alexa594 | SEQ ID NO: 239 |
| SUPT5H_int_16 | atccagtgctacagcttaga | ATTO647N | SEQ ID NO: 240 |

TABLE 1-continued

| Probe | Probe Sequence | Organic Dye | Sequence Number |
|---|---|---|---|
| TOMM40_int_1 | atcacctcctagtgctgtta | ATTO647N | SEQ ID NO: 241 |
| TOMM40_int_2 | ccatcattctaagccccaag | Alexa594 | SEQ ID NO: 242 |
| TOMM40_int_3 | ctgctatgacattccatccc | ATTO647N | SEQ ID NO: 243 |
| TOMM40_int_4 | gatcacaagagaagtctggc | Alexa594 | SEQ ID NO: 244 |
| TOMM40_int_5 | gaacaccagaacagaactcc | ATTO647N | SEQ ID NO: 245 |
| TOMM40_int_6 | cacagaattgtcccaaggat | Alexa594 | SEQ ID NO: 246 |
| TOMM40_int_7 | aagctgagcaactttaggtc | ATTO647N | SEQ ID NO: 247 |
| TOMM40_int_8 | ttgcttgctcaaatctcact | Alexa594 | SEQ ID NO: 248 |
| TOMM40_int_9 | tacagcctagttagacaggg | ATTO647N | SEQ ID NO: 249 |
| TOMM40_int_10 | gattccacctgtaaagaggc | Alexa594 | SEQ ID NO: 250 |
| TOMM40_int_11 | cacagcagaacatctcacaa | ATTO647N | SEQ ID NO: 251 |
| TOMM40_int_12 | gagaagagaaacgctgtcac | Alexa594 | SEQ ID NO: 252 |
| TOMM40_int_13 | tctggcactatatctccgag | ATTO647N | SEQ ID NO: 253 |
| TOMM40_int_14 | taggtccccaaactgagtag | Alexa594 | SEQ ID NO: 254 |
| TOMM40_int_15 | agagactcagagaaaggagg | ATTO647N | SEQ ID NO: 255 |
| TOMM40_int_16 | tgtgacgatactggacagat | Alexa594 | SEQ ID NO: 256 |
| UBA2_int_1 | ccaaagaacagtctcctccc | ATTO647N | SEQ ID NO: 257 |
| UBA2_int_2 | ttgaagggaggataagaggc | ATTO488 | SEQ ID NO: 258 |
| UBA2_int_3 | ctcctaacagccgggaattt | Alexa594 | SEQ ID NO: 259 |
| UBA2_int_4 | ttaaagtcacaacatccgcg | ATTO647N | SEQ ID NO: 260 |
| UBA2_int_5 | tcgttacttcggagttacga | ATTO488 | SEQ ID NO: 261 |
| UBA2_int_6 | tcgctatcattgccatcctc | Alexa594 | SEQ ID NO: 262 |
| UBA2_int_7 | ctgtgagagcaatgacagtc | ATTO647N | SEQ ID NO: 263 |
| UBA2_int_8 | atgaaacaagcgagtgtacc | ATTO488 | SEQ ID NO: 264 |
| UBA2_int_9 | caaaaggcacagtcctaacg | Alexa594 | SEQ ID NO: 265 |
| UBA2_int_10 | aaatagcactggcttgtcaa | ATTO647N | SEQ ID NO: 266 |
| UBA2_int_11 | tttaaactcacaccgaaggg | ATTO488 | SEQ ID NO: 267 |
| UBA2_int_12 | tgtttccactagcccttaag | Alexa594 | SEQ ID NO: 268 |
| UBA2_int_13 | aacctgagaactgtgaaagg | ATTO647N | SEQ ID NO: 269 |
| UBA2_int_14 | cctcccttaattcaagcctt | ATTO488 | SEQ ID NO: 270 |
| UBA2_int_15 | ttcgaatcgccataccaaaa | Alexa594 | SEQ ID NO: 271 |
| UBA2_int_16 | tacattagtggagaaagcgt | ATTO647N | SEQ ID NO: 272 |
| UBA52_int_1 | ctaaagtcagcacaacccac | ATTO700 | SEQ ID NO: 273 |
| UBA52_int_2 | gagaagcaagggcaaaacag | Alexa594 | SEQ ID NO: 274 |
| UBA52_int_3 | caaacgttcttcagatcaca | ATTO700 | SEQ ID NO: 275 |
| UBA52_int_4 | ggccaactgaggtagaagat | Alexa594 | SEQ ID NO: 276 |
| UBA52_int_5 | cactaccccagtttctcaa | ATTO700 | SEQ ID NO: 277 |
| UBA52_int_6 | tattactggcagtgtcctct | Alexa594 | SEQ ID NO: 278 |
| UBA52_int_7 | gaggctcagttagaggctct | ATTO700 | SEQ ID NO: 279 |

TABLE 1-continued

| Probe | Probe Sequence | Organic Dye | Sequence Number |
|---|---|---|---|
| UBA52_int_8 | caatgctcctttcctaggac | Alexa594 | SEQ ID NO: 280 |
| UBA52_int_9 | acactgaattcttgtcgctc | ATTO700 | SEQ ID NO: 281 |
| UBA52_int_10 | aaggtcagacactgaagtct | Alexa594 | SEQ ID NO: 282 |
| UBA52_int_11 | ccgacctctaagtggttcag | ATTO700 | SEQ ID NO: 283 |
| UBA52_int_12 | gcatccatctgggtttctaa | Alexa594 | SEQ ID NO: 284 |
| UBA52_int_13 | ggagtctgagactgacacat | ATTO700 | SEQ ID NO: 285 |
| UBA52_int_14 | cgtgtggaagatacactgtc | Alexa594 | SEQ ID NO: 286 |
| UBA52_int_15 | gcctatagtctgctgctttc | ATTO700 | SEQ ID NO: 287 |
| UBA52_int_16 | caagcatcggagcacacata | Alexa594 | SEQ ID NO: 288 |
| ZNF444_int_1 | gagtcacatggttttcagg | ATTO700 | SEQ ID NO: 289 |
| ZNF444_int_2 | cttctctgataagccgtgac | Cy3 | SEQ ID NO: 290 |
| ZNF444_int_3 | gagaggacagctggtaactg | ATTO647N | SEQ ID NO: 291 |
| ZNF444_int_4 | ttttgaacacattggggtcc | ATTO700 | SEQ ID NO: 292 |
| ZNF444_int_5 | gtgccactactgaaaggatg | Cy3 | SEQ ID NO: 293 |
| ZNF444_int_6 | gactgctctgactcttcacc | ATTO647N | SEQ ID NO: 294 |
| ZNF444_int_7 | ggtacgcacttatgaggaac | ATTO700 | SEQ ID NO: 295 |
| ZNF444_int_8 | tctctgctgctacatctcag | Cy3 | SEQ ID NO: 296 |
| ZNF444_int_9 | catgagaagggagacggatg | ATTO647N | SEQ ID NO: 297 |
| ZNF444_int_10 | atcccagacaataagagggg | ATTO700 | SEQ ID NO: 298 |
| ZNF444_int_11 | cgaggatagagaagccagag | Cy3 | SEQ ID NO: 299 |
| ZNF444_int_12 | cccacttttgggaacaatga | ATTO647N | SEQ ID NO: 300 |
| ZNF444_int_13 | gctgcgtttgtgatttgtta | ATTO700 | SEQ ID NO: 301 |
| ZNF444_int_14 | ggatgaaagcagaggtcaag | Cy3 | SEQ ID NO: 302 |
| ZNF444_int_15 | ggatgaaagcagaggtcaag | ATTO647N | SEQ ID NO: 303 |
| ZNF444_int_16 | taagtgggtcaaggtcagag | ATTO700 | SEQ ID NO: 304 |
| ZNF91_int_1 | gattgtggagctgactgaag | ATTO488 | SEQ ID NO: 305 |
| ZNF91_int_2 | catcttatcgctgaagggga | Cy3 | SEQ ID NO: 306 |
| ZNF91_int_3 | ctgcacaatctgggagagac | Alexa594 | SEQ ID NO: 307 |
| ZNF91_int_4 | gagttaggctggaggaacag | ATTO488 | SEQ ID NO: 308 |
| ZNF91_int_5 | tggtaagatagctgcgtcta | Cy3 | SEQ ID NO: 309 |
| ZNF91_int_6 | actgaagacacatcaccctc | Alexa594 | SEQ ID NO: 310 |
| ZNF91_int_7 | tccaagaaaaaactgaaggg | ATTO488 | SEQ ID NO: 311 |
| ZNF91_int_8 | agagaatatgacccagaagc | Cy3 | SEQ ID NO: 312 |
| ZNF91_int_9 | tcaatacctcaggttgtcct | Alexa594 | SEQ ID NO: 313 |
| ZNF91_int_10 | gtccacacttgagaagctaa | ATTO488 | SEQ ID NO: 314 |
| ZNF91_int_11 | cactattttctgcccccta | Cy3 | SEQ ID NO: 315 |
| ZNF91_int_12 | gcaagttcttacgccatcta | Alexa594 | SEQ ID NO: 316 |
| ZNF91_int_13 | gtgcctcaggcacattatac | ATTO488 | SEQ ID NO: 317 |
| ZNF91_int_14 | aggagactctgaactatgcc | Cy3 | SEQ ID NO: 318 |

TABLE 1-continued

| Probe | Probe Sequence | Organic Dye | Sequence Number |
| --- | --- | --- | --- |
| ZNF91_int_15 | ttaagtgctcaataacccc | Alexa594 | SEQ ID NO: 319 |
| ZNF91_int_16 | tcaagtcaggccattcaatt | ATTO488 | SEQ ID NO: 320 |
| SUZ12_mRNA_1 | ctccattttcggcttcttca | ATTO647N | SEQ ID NO: 321 |
| SUZ12_mRNA_2 | gaggaaaagctcgtggtcag | ATTO488 | SEQ ID NO: 322 |
| SUZ12_mRNA_3 | gatctgtgttggcttctcaa | ATTO700 | SEQ ID NO: 323 |
| SUZ12_mRNA_4 | gagattccgagttcgaagaa | Cy3 | SEQ ID NO: 324 |
| SUZ12_mRNA_5 | tgtgcaaaaatattggtgct | Alexa594 | SEQ ID NO: 325 |
| SUZ12_mRNA_6 | tctggagtttcgatgagaca | ATTO647N | SEQ ID NO: 326 |
| SUZ12_mRNA_7 | tgagattcttgctctcctttt | ATTO488 | SEQ ID NO: 327 |
| SUZ12_mRNA_8 | ctgcaaatgagctgacaagc | ATTO700 | SEQ ID NO: 328 |
| SUZ12_mRNA_9 | tggaagaaaccagtaaacgt | Cy3 | SEQ ID NO: 329 |
| SUZ12_mRNA_10 | aagagtgaactgcaacgtag | Alexa594 | SEQ ID NO: 330 |
| SUZ12_mRNA_11 | gcaataggagccgtagattt | ATTO647N | SEQ ID NO: 331 |
| SUZ12_mRNA_12 | atttctagtggcaagaggtt | ATTO488 | SEQ ID NO: 332 |
| SUZ12_mRNA_13 | taactgaaccaggcttgttt | ATTO700 | SEQ ID NO: 333 |
| SUZ12_mRNA_14 | acagcaatagtttgagtagg | Cy3 | SEQ ID NO: 334 |
| SUZ12_mRNA_15 | tgttgccttgtattgttgtt | Alexa594 | SEQ ID NO: 335 |
| SUZ12_mRNA_16 | caggtcatctcttgcttcag | ATTO647N | SEQ ID NO: 336 |
| SUZ12_mRNA_17 | tcagagtacaccaagggcaa | ATTO488 | SEQ ID NO: 337 |
| SUZ12_mRNA_18 | aaactataaagtttgcggca | ATTO700 | SEQ ID NO: 338 |
| SUZ12_mRNA_19 | tggcagagtttaagatgctt | Cy3 | SEQ ID NO: 339 |
| SUZ12_mRNA_20 | cctagcaccttttggatgat | Alexa594 | SEQ ID NO: 340 |
| SUZ12_mRNA_21 | ggagccatcataacactcat | ATTO647N | SEQ ID NO: 341 |
| SUZ12_mRNA_22 | tatcctgaggatttcctgca | ATTO488 | SEQ ID NO: 342 |
| SUZ12_mRNA_23 | tgcgactaaaagcaaatcca | ATTO700 | SEQ ID NO: 343 |
| SUZ12_mRNA_24 | ggtgttctcttaactggtcc | Cy3 | SEQ ID NO: 344 |
| SUZ12_mRNA_25 | gcctgcacaccaagaatatgt | Alexa594 | SEQ ID NO: 345 |
| SUZ12_mRNA_26 | catgcttgcttttgttcgtt | ATTO647N | SEQ ID NO: 346 |
| SUZ12_mRNA_27 | ctttgctgttctacttcccc | ATTO488 | SEQ ID NO: 347 |
| SUZ12_mRNA_28 | aaatacagacgattgtggcc | ATTO700 | SEQ ID NO: 348 |
| SUZ12_mRNA_29 | agaggtaagcaggtatcact | Cy3 | SEQ ID NO: 349 |
| SUZ12_mRNA_30 | gacatggagattccagagtt | Alexa594 | SEQ ID NO: 350 |
| SUZ12_mRNA_31 | cagcaataaacccatgcttc | ATTO647N | SEQ ID NO: 351 |
| SUZ12_mRNA_32 | caggcatgattcatttgatt | ATTO488 | SEQ ID NO: 352 |
| SUZ12_mRNA_33 | tgaagcatgaagtttcgaca | ATTO700 | SEQ ID NO: 353 |
| SUZ12_mRNA_34 | aaagtcatgcatgctgacta | Cy3 | SEQ ID NO: 354 |
| SUZ12_mRNA_35 | catttcacggagcttggtaa | Alexa594 | SEQ ID NO: 355 |
| SUZ12_mRNA_36 | tatttcttcgtttgcagggg | ATTO647N | SEQ ID NO: 356 |
| SUZ12_mRNA_37 | ccatttgctgtcccatttttg | ATTO488 | SEQ ID NO: 357 |

TABLE 1-continued

| Probe | Probe Sequence | Organic Dye | Sequence Number |
|---|---|---|---|
| SUZ12_mRNA_38 | ctgttttgaaaccoctgaga | ATTO700 | SEQ ID NO: 358 |
| SUZ12_mRNA_39 | acatggggttagagcttttc | Cy3 | SEQ ID NO: 359 |
| SUZ12_mRNA_40 | agaggatgaattccctaaaa | Alexa594 | SEQ ID NO: 360 |
| SUZ12_mRNA_41 | tgaagtagaaccctgataca | ATTO647N | SEQ ID NO: 361 |
| SUZ12_mRNA_42 | cctccccaagaaaatgtctc | ATTO488 | SEQ ID NO: 362 |
| SUZ12_mRNA_43 | aggatcaaagtttgactgca | ATTO700 | SEQ ID NO: 363 |
| SUZ12_mRNA_44 | gggtgagcaatgcactaaaa | Cy3 | SEQ ID NO: 364 |
| SUZ12_mRNA_45 | acagcttaattttccgtgtg | Alexa594 | SEQ ID NO: 365 |
| SUZ12_mRNA_46 | caaatgcgttctttccttgg | ATTO647N | SEQ ID NO: 366 |
| SUZ12_mRNA_47 | ttctccccttataagtgaca | ATTO488 | SEQ ID NO: 367 |
| SUZ12_mRNA_48 | agtcagcttatctctattgg | ATTO700 | SEQ ID NO: 368 |
| SUZ12_mRNA_49 | acacatataacacagggcaa | Cy3 | SEQ ID NO: 369 |
| SUZ12_mRNA_50 | caactgcaaatatgtgcgtg | Alexa594 | SEQ ID NO: 370 |
| SUZ12_mRNA_51 | tgcttgttaatgtgccagta | ATTO647N | SEQ ID NO: 371 |
| SUZ12_mRNA_52 | cggagttggaataaaaacct | ATTO488 | SEQ ID NO: 372 |
| SUZ12_mRNA_53 | gatgttactcaaccacagtg | ATTO700 | SEQ ID NO: 373 |
| SUZ12_mRNA_54 | acacatcttaaagaccagtc | Cy3 | SEQ ID NO: 374 |
| SUZ12_mRNA_55 | tcgttaaatagcctcacagt | Alexa594 | SEQ ID NO: 375 |
| SUZ12_mRNA_56 | tgacaaatcacatccacact | ATTO647N | SEQ ID NO: 376 |
| SUZ12_mRNA_57 | aatgaaagctgcagtttccc | ATTO488 | SEQ ID NO: 377 |
| SUZ12_mRNA_58 | gcttaccaatcaaggaatct | ATTO700 | SEQ ID NO: 378 |
| SUZ12_mRNA_59 | ccagaggcaaaaatcagagt | Cy3 | SEQ ID NO: 379 |
| SUZ12_mRNA_60 | cgagataaacgctcgagatc | Alexa594 | SEQ ID NO: 380 |
| SUZ12_mRNA_61 | tatgtgcacagctttagcaa | ATTO647N | SEQ ID NO: 381 |
| SUZ12_mRNA_62 | ttctacacctacatctcccc | ATTO488 | SEQ ID NO: 382 |
| SUZ12_mRNA_63 | agcattaagagcataactgc | ATTO700 | SEQ ID NO: 383 |
| SUZ12_mRNA_64 | gcaaacaatgctagccttct | Cy3 | SEQ ID NO: 384 |
| SUZ12_mRNA_65 | ggtgggaatcaccaactttt | Alexa594 | SEQ ID NO: 385 |
| CCNA2_exons_1 | gtctgctgcaatgctagcag | Cy3 | SEQ ID NO: 386 |
| CCNA2_exons_2 | gccttttccgggttgatatt | Cy3 | SEQ ID NO: 387 |
| CCNA2_exons_3 | ggttcccggacttcagtacc | Cy3 | SEQ ID NO: 388 |
| CCNA2_exons_4 | aggaagatccttaaggggtg | Cy3 | SEQ ID NO: 389 |
| CCNA2_exons_5 | ttgctttccaaggaggaacg | Cy3 | SEQ ID NO: 390 |
| CCNA2_exons_6 | gtgaacgcaggctgtttact | Cy3 | SEQ ID NO: 391 |
| CCNA2_exons_7 | ttctgcttcatccacatgaa | Cy3 | SEQ ID NO: 392 |
| CCNA2_exons_8 | ctggcttcttctgagcttct | Cy3 | SEQ ID NO: 393 |
| CCNA2_exons_9 | tcacgctctattttttgaga | Cy3 | SEQ ID NO: 394 |
| CCNA2_exons_10 | tgaattaaaagccagggcat | Cy3 | SEQ ID NO: 395 |
| CCNA2_exons_11 | aagagggaccaatggttttc | Cy3 | SEQ ID NO: 396 |

TABLE 1-continued

| Probe | Probe Sequence | Organic Dye | Sequence Number |
|---|---|---|---|
| CCNA2_exons_12 | tttccctaaggtatgtgtga | Cy3 | SEQ ID NO: 397 |
| CCNA2_exons_13 | tcatgtaacccactttaggt | Cy3 | SEQ ID NO: 398 |
| CCNA2_exons_14 | gttagtgatgtctggctgtt | Cy3 | SEQ ID NO: 399 |
| CCNA2_exons_15 | ccacgaggatagctctcata | Cy3 | SEQ ID NO: 400 |
| CCNA2_exons_16 | atgtagttcacagccaaatg | Cy3 | SEQ ID NO: 401 |
| CCNA2_exons_17 | acatggaagacaggaaccta | Cy3 | SEQ ID NO: 402 |
| CCNA2_exons_18 | ctaacagcatagcagcagtg | Cy3 | SEQ ID NO: 403 |
| CCNA2_exons_19 | tgtacacaaactctgctact | Cy3 | SEQ ID NO: 404 |
| CCNA2_exons_20 | ttggtgtaggtatcatctgt | Cy3 | SEQ ID NO: 405 |
| CCNA2_exons_21 | gctccattctcagaacttgt | Cy3 | SEQ ID NO: 406 |
| CCNA2_exons_22 | gtcaaaagtaaggactttca | Cy3 | SEQ ID NO: 407 |
| CCNA2_exons_23 | gatttactgttggagcagct | Cy3 | SEQ ID NO: 408 |
| CCNA2_exons_24 | tgatgcagaaagtattgggt | Cy3 | SEQ ID NO: 409 |
| CCNA2_exons_25 | ttcaactttgcagtttgcag | Cy3 | SEQ ID NO: 410 |
| CCNA2_exons_26 | ttgaggtatgggtcagcatc | Cy3 | SEQ ID NO: 411 |
| CCNA2_exons_27 | agcaataactgatggcaaat | Cy3 | SEQ ID NO: 412 |
| CCNA2_exons_28 | gtgctaaatgaaaggcagct | Cy3 | SEQ ID NO: 413 |
| CCNA2_exons_29 | ctttgtcccgtgactgtgta | Cy3 | SEQ ID NO: 414 |
| CCNA2_exons_30 | ccagtctttcgtattaatga | Cy3 | SEQ ID NO: 415 |
| CCNA2_exons_31 | gcttaagactttccagggta | Cy3 | SEQ ID NO: 416 |
| CCNA2_exons_32 | gtgctttgaggtaggtctgg | Cy3 | SEQ ID NO: 417 |
| CCNA2_exons_33 | tattgactgttgtgcatgct | Cy3 | SEQ ID NO: 418 |
| CCNA2_exons_34 | gaggagagaaacaccatgat | Cy3 | SEQ ID NO: 419 |
| CCNA2_exons_35 | gatttagtgtctctggtggg | Cy3 | SEQ ID NO: 420 |
| roX2_1 | uauguaacaccaauuuaccc | TAMRA | SEQ ID NO: 421 |
| roX2_2 | ugugauuccaaauagucgu | TAMRA | SEQ ID NO: 422 |
| roX2_3 | guuuuguagcuugacaagcg | TAMRA | SEQ ID NO: 423 |
| roX2_4 | uguauauuguauaucauuca | TAMRA | SEQ ID NO: 424 |
| roX2_5 | gcguuccaagacacauuuuu | TAMRA | SEQ ID NO: 425 |
| roX2_6 | cguuacccauauaugcauau | TAMRA | SEQ ID NO: 426 |
| roX2_7 | ugacugguuaaggcgcguaa | TAMRA | SEQ ID NO: 427 |
| MtnA_1 | cugcugaccacaacugaugc | TAMRA | SEQ ID NO: 428 |
| MtnA_2 | cacugagaugauucacuuga | TAMRA | SEQ ID NO: 429 |
| MtnA_3 | gggcuauuuaggccuuuagu | TAMRA | SEQ ID NO: 430 |
| MtnA_4 | uauuccucgaacuuguuca | TAMRA | SEQ ID NO: 431 |
| MtnA_5 | gcaaggcaucuugauugagu | TAMRA | SEQ ID NO: 432 |
| MtnA_6 | ccgcacuugcagucagaucc | TAMRA | SEQ ID NO: 433 |
| MtnA_7 | guguagagagacaagaugca | TAMRA | SEQ ID NO: 434 |
| MtnA_8 | aauuggacauuuauugcagg | TAMRA | SEQ ID NO: 435 |

TABLE 1-continued

| Probe | Probe Sequence | Organic Dye | Sequence Number |
|---|---|---|---|
| roX2_FISH_1 | ttcgaaacgatctctaaagc | Cy5 | SEQ ID NO: 436 |
| roX2_FISH_2 | tttcgaacgattatcaatgt | Cy5 | SEQ ID NO: 437 |
| roX2_FISH_3 | cttgattttgcttcggagaa | Cy5 | SEQ ID NO: 438 |
| roX2_FISH_4 | tatgcggaaatcgttactct | Cy5 | SEQ ID NO: 439 |
| roX2_FISH_5 | attcaacttaaacattttcg | Cy5 | SEQ ID NO: 440 |
| roX2_FISH_6 | tcatctcactgtccgtaaga | Cy5 | SEQ ID NO: 441 |
| roX2_FISH_7 | tcaaccatgaaaacaattcg | Cy5 | SEQ ID NO: 442 |
| roX2_FISH_8 | gcattgcgacttgtacaatg | Cy5 | SEQ ID NO: 443 |
| roX2_FISH_9 | acacgtcttttaagacttca | Cy5 | SEQ ID NO: 444 |
| roX2_FISH_10 | tttgcttaatttgcaacatt | Cy5 | SEQ ID NO: 445 |
| roX2_FISH_11 | acatttcactagttatatga | Cy5 | SEQ ID NO: 446 |
| MtnA_FISH_1 | atttgcatccgcttccgcat | Cy5 | SEQ ID NO: 447 |
| MtnA_FISH_2 | agttgcaggatcccttggtg | Cy5 | SEQ ID NO: 448 |
| MtnA_FISH_3 | gcaggcggatttcttgtcgc | Cy5 | SEQ ID NO: 449 |
| MtnA_FISH_4 | ggaaagctcactcggagcag | Cy5 | SEQ ID NO: 450 |
| MtnA_FISH_5 | gcctctactccagatctttt | Cy5 | SEQ ID NO: 451 |

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Simultaneous Determination of Chromosome Structure and Gene Expression As depicted in FIG. 1B, 18 genes were targeted along chromosome 19, illuminating the chromosome robustly and with low background. Because the method of the present invention is based on RNA FISH, it is easy to combine with RNA FISH labeling mRNAs to simultaneously measure the expression of specific genes, as depicted in FIG. 1C. The introns themselves also yield critical gene expression information, since most genes' introns yield spots in fewer than 50% of cells. That said, the determination of overall chromosome structure via the methods of the present invention can additionally include the labeling of a large number of genes, thus imparting redundancy into the method, and may further include an RT-PCR screen to aid in the bioinformatic identification of abundant intron targets.

As depicted in FIG. 1B, distinctly labeled genes in three different regions of chromosome 19 reveal a remarkably ordered intrachromsomal configuration. When comparing the spot patterns in different cells, chromosomes can take a wide variety of shapes. Surprisingly, some data gathered suggests that within certain cells, the two copies of the chromosome sometimes adopt a very similar spot pattern, as depicted in FIG. 1B. This indicates that expression and shape is correlated between the two copies of chromosomes within single cells.

Figures 3A, 3B:
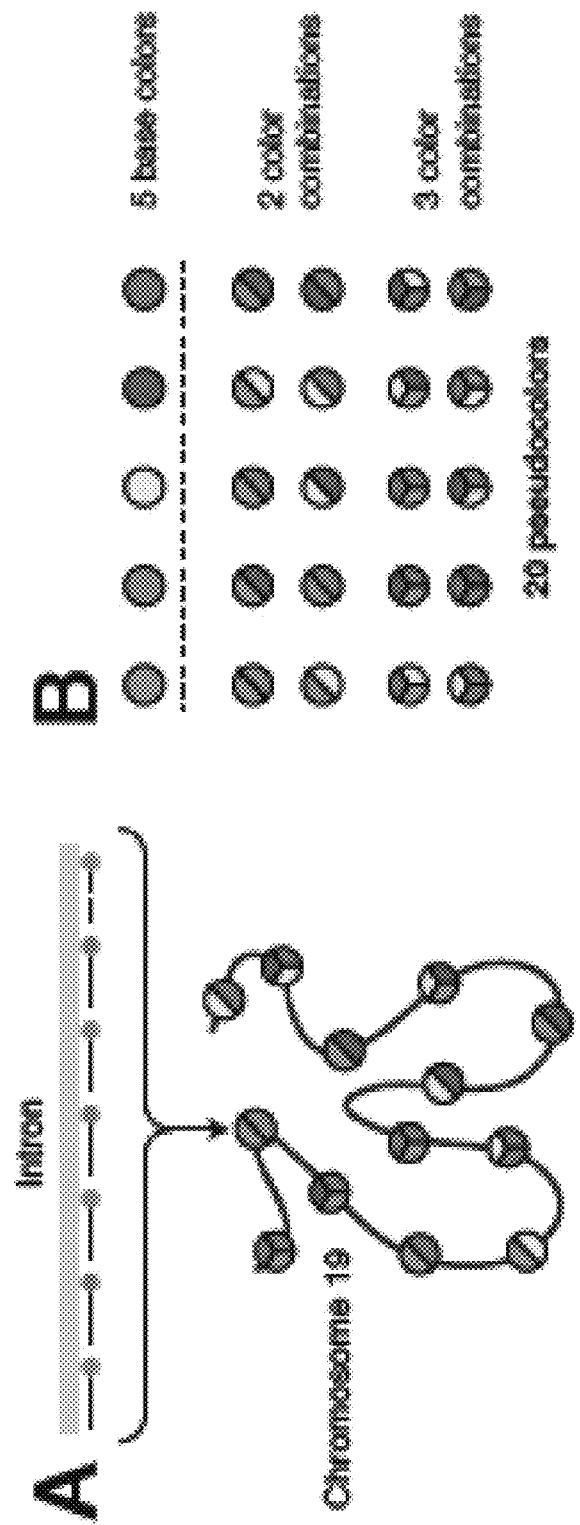
FIGS. 3A-3I, depicts a demonstration of a pseudo-coloring scheme for measuring transcriptional activity and position of 20 genes at once.
Figures 3C, 3D, 3E, 3F, 3G, 3H, 3I:
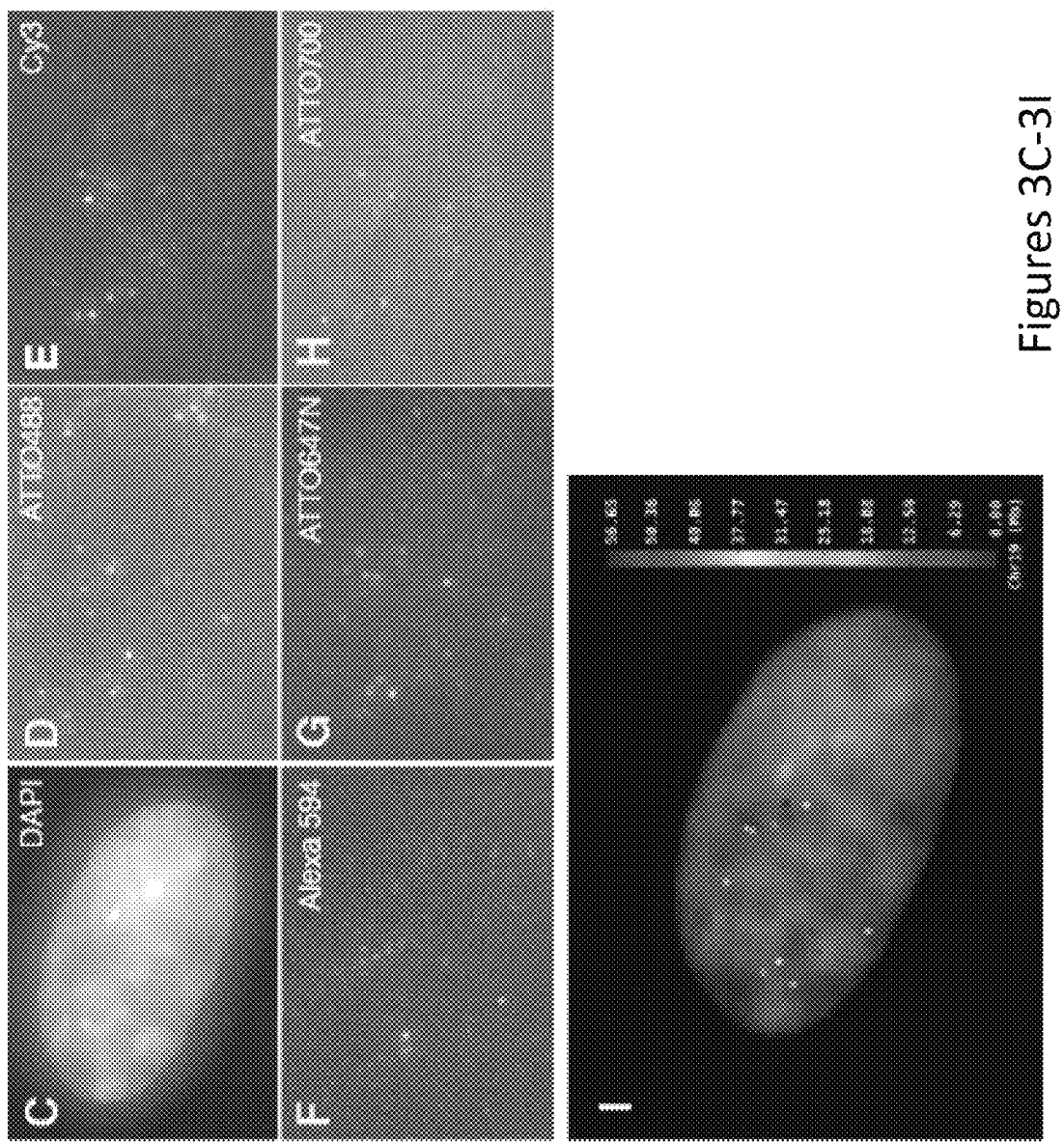

In a second set of experiments, the transcription site of 20 unique genes along chromosome 19 was detected using color-coded probes, as depicted in FIG. 3. Here, a false spot identification rate below 5% is demonstrated. These spot data for 20 genes were used to reconstruct chromosome conformations of actively transcribing genes (FIG. 3).

Example 2: Measuring Chromosome Structure and Gene Expression In Vivo

Many insights in systems biology have arisen from the use of time-lapse microscopy to understand the dynamics of cellular processes. For this reason, the methods of the present invention can also be applied to living cells to provide a dynamic view of chromosome structure and gene expression. To date, there is no way of looking at chromosome structure or gene expression in a non-perturbative (i.e., no genetic manipulation) manner via microscopy in single living cells.

Experiments can be performed to tackle the challenges of targeting nucleic acids in vivo. For example, considerations include hybridization kinetics, sequence design, oligonucleotide chemistry and delivery methods, amongst several others. RNA of a single intron from a highly expressed gene can be targeted by designing a series of 16-48 oligonucleotides, with the idea that the binding of a large number of oligonucleotides to a single location in the cell can result in a detectable spot. These oligonucleotides can be synthesized with a variety of modified backbone chemistries (such as 2'O-methyl), which are necessary to render the oligonucleotides impervious to various cellular nucleases. Depending on the results, the design of the oligonucleotides can be altered, perhaps employing a "molecular beacon" or other probe designs that are capable of decreasing background through the use of quenchers, particularly in the nucleus.

Probe delivery methods can include microinjection, microporation and lipid-based transfection reagents, for example. Given the methods capable of detecting a single RNA, and the fact that most intron spots contain between 5 and 10 intron RNA molecules to target, individual intron spots can be detected in vivo, using FISH as a control for validation.

After detecting a single intron, the methods of the present invention can be used to label multiple introns simultaneously, with the aim of labeling an entire chromosome in vivo while also providing some coarse measurements of gene expression. The spots can then be color coded to reproduce a barcoded chromosome in a living cell.

Figure 5:
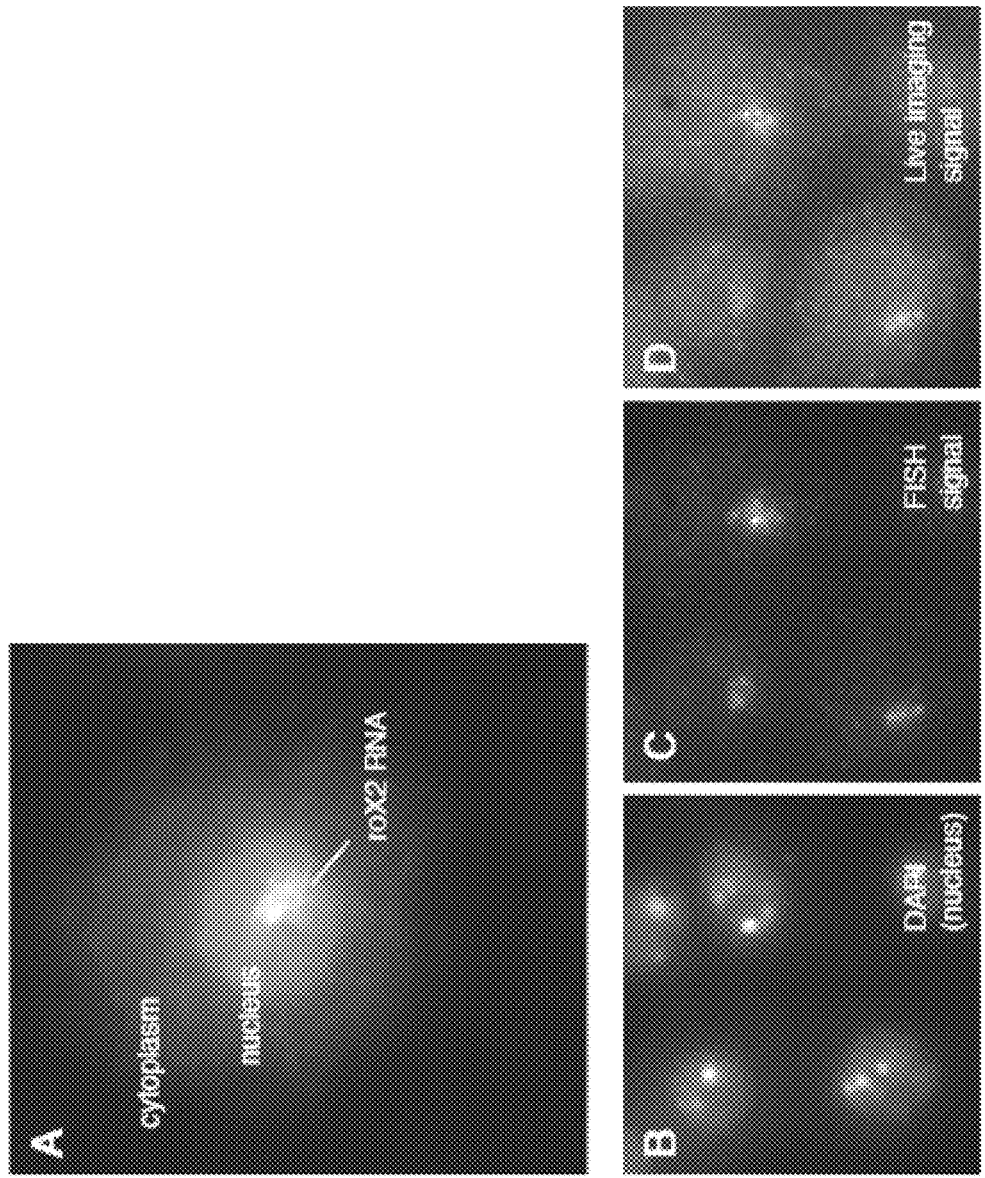
FIG. 5, comprising
Figure 6:
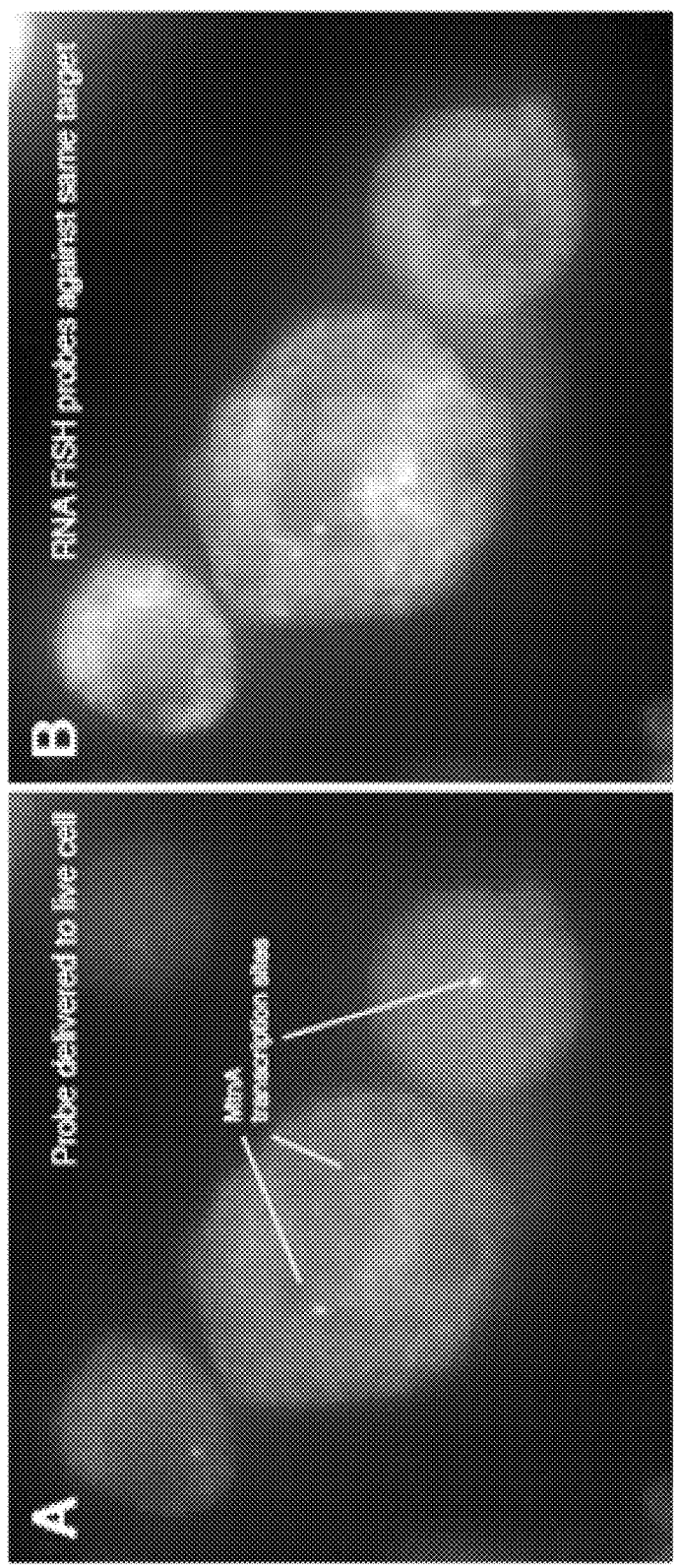
FIG. 6, comprising

The methods described herein provide a way to perform live RNA imaging. This imaging can be performed on long non-coding RNA (roX2) in *Drosophila melanogaster* cells. This particular RNA coats the X chromosome, resulting in a very peculiar spatial distribution in the cell. This spatial distribution was exploited to test unambiguously whether the described method can detect endogenous RNA in single living cells and can show the structure of the X chromosome. For example, a live imaging probe (consisting of eight labeled oligonucleotides) was found to detect the roX2 RNA, and the signals were verified by RNA FISH (FIG. 5). In another example, live RNA imaging was performed on an endogenous gene in *Drosophila melanogaster* cells. The gene which is turned on in the presence of copper, was specifically targeted. Oligonucleotide probes were delivered to live cells, and then the probes were detected after fixation. The specificity of the signal was verified by targeting the same target after fixation using RNA FISH with differently labeled probes, with the result that the signals colocalized (FIG. 6).

Example 3: Determination of Location and Transcriptional Frequency of Chromosomal Fragments The location of different chromosomal fragments in HeLa cells was determined on a single cell basis using methods described herein As shown in FIG. 4, these chromosomal fragments include two intact copies of chromosome 19 as well as another copy of chromosome 19 that has been split in half, where one half is fused to a portion of chromosome 13 and the second half is fused to a portion of chromosome 6.

The transcriptional frequency of the intact copies of chromosome 19 was then compared to the translocated fragments. By spatially segregating introns based on nuclear proximity, individual chromosomes and chromosome fragments were isolated, and instantaneous transcriptional activity was measured on a per-chromosome basis. The transcriptional activity was measured in units of fraction of chromosomes exhibiting an intron spot for the given gene for 20 genes along chromosome 19. It was found that the genes on the portion of chromosome 19 that was fused to chromosome 6 transcribe about as often as those on the intact chromosome 19, while genes on the portion of chromosome 19 that was fused to chromosome 13 generally express at a considerably higher rate than those on the intact copy. Thus, the present invention provides a method to measure transcription on a per-chromosome basis.

Example 4: Translocations in Cancer

Many forms of cancer exhibit stereotypical chromosomal translocations (Mitelman et al., 2007, Nat Rev Cancer 7: 233-245), perhaps most famously the Philadelphia translocation, which results in the formation of an oncogenic fusion protein (BRC-ABL), which in turn leads to chronic myelogenous leukemia. The development of RNA sequencing technologies has shown the prevalence of specific fusions in a variety of cancers. Yet, the question remains of exactly how these very specific translocations occur. Specific translocations may arise due to colocalization of certain chromosomal locations during the transcription of specific genes.

The method described herein provides a new way for measuring these translocations. By measuring chromosome structure via the present invention, one can detect the translocation itself directly. Moreover, the method is easily combined with RNA FISH, thereby facilitating the detection of the fusion transcript by labeling the two halves of the fusion with differently colored probes. This would enable the measurement of the expression level of the oncogenic fusion transcript as well as chromosomal translocations within a single cell.

Figure 2:
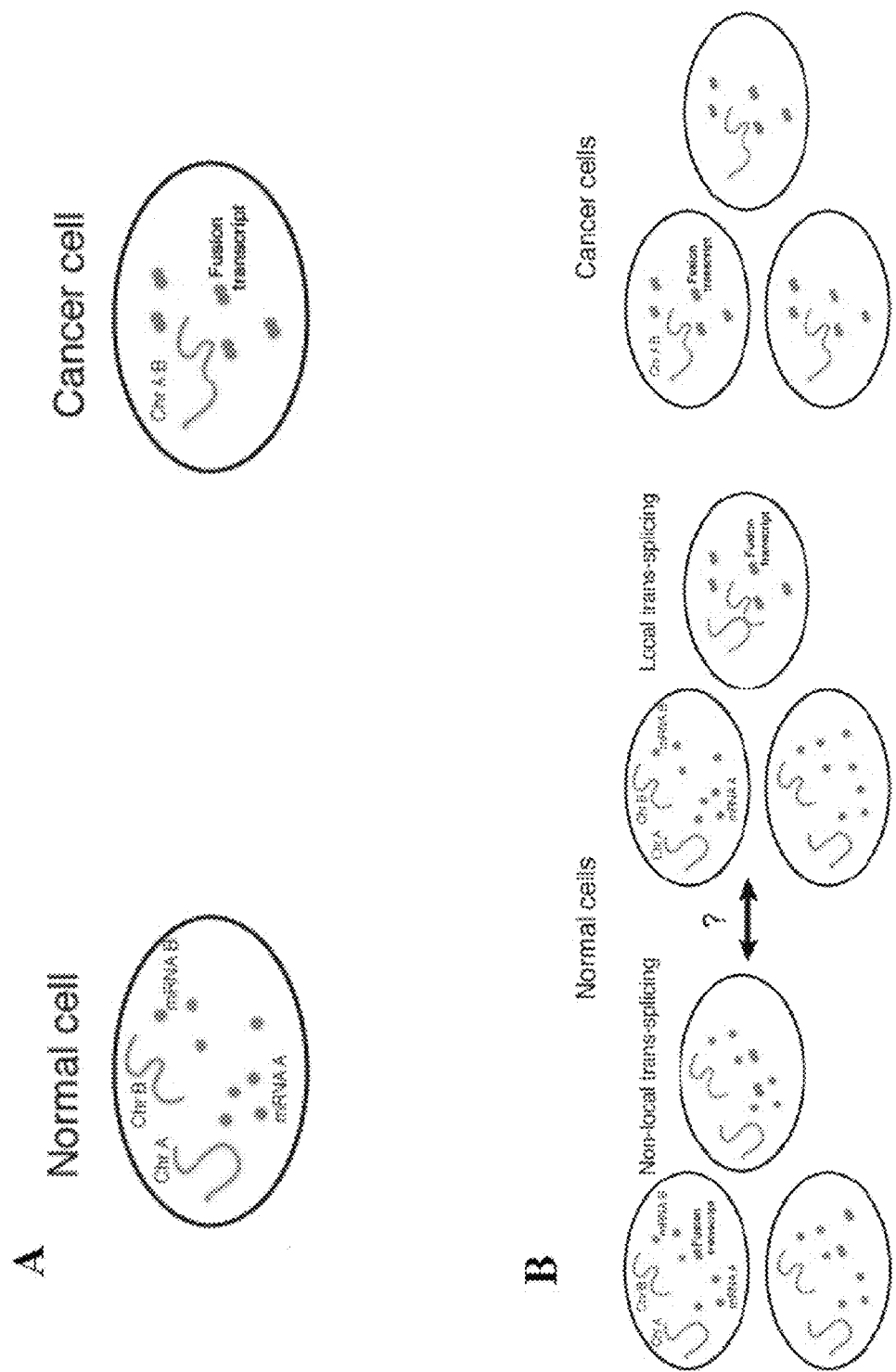
FIG. 2, comprising

For example, translocations resulting in the fusion of the JAZF1 and JJAZ1 proteins can be studied, which is implicated in the formation of endometrial cancer. Interestingly, fusion transcripts appear even in non-cancerous cells that do not contain the translocation, suggesting that the normal transcription of these genes can sometimes result in their physical proximity that then lead to trans-splicing events. The two chromosomes involved (7 and 17) can be targeted together with the two halves of the fusion transcript via single molecule RNA FISH both in wild-type cells and cells that harbor the translocation (FIG. 2 and FIG. 1C). Colocalization analysis with the two chromosomes allows one to determine the relative locations of the relevant genetic loci and how they are related to the overall shape of the chromosomes. Meanwhile, one can simultaneously look for colocalization of the two halves of the fusion transcript. Colocalization of the two probes implies presence of the fusion transcript, while signal from individual probes represents non-fused transcripts. Currently, it is unknown whether wild-type cells contain some amount of the fusion transcript in every cell or only a small subpopulation of cells produce the fusion transcript in high abundance. In either case, the single cell, single molecule analysis of the present invention allows one to answer this question directly and relate any findings to the structure of the chromosomes involved.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for simultaneously determining the structural conformation of a chromosome in a cell and quantitatively measuring the level of gene expression at a chromosomal location, the method comprising hybridizing a plurality of target sequences of more than one transcribed RNA in the cell with members of at least one set of more than sixteen fluorescently labeled oligonucleotide probes for each transcribed RNA and counting fluorescent spots corresponding to single molecules of target transcribed RNAs to obtain a quantitative gene expression profile corresponding to the simultaneously determined, associated chromosomal conformation, wherein:
   (i) the plurality of target sequences of transcribed RNA are transcribed from portions of at least one chromosome;
   (ii) the pattern of fluorescently labeled probes hybridized to the target sequences of transcribed RNA is indicative of the structural conformation of the chromosome;
   (iii) the locations of the hybridized probes are simultaneously indicative of the chromosomal locations of gene expression for the transcribed RNAs;
   (iv) the number, the intensity, or both, of fluorescing probes is indicative of the level of gene expression at the chromosomal locations;
   (v) each fluorescently labeled probe targets an intron of the transcribed RNA sequence; thereby simultaneously determining the structural conformation of a chromosome in a cell and measuring the level of gene expression at a chromosomal location;
   (vi) at least two introns are targeted in the cell and at least sixteen fluorescently labeled probes having different nucleotide sequences are complementary to each targeted intron;
   (vii) each of the fluorescently labeled oligonucleotides are coupled to an organic dye at their 3' end;
   (viii) each probe set utilizes a distinguishable color; and
   (ix) a fluorescent spot is discarded as background based at least on color.

2. The method of claim 1, wherein the probes are non-overlapping.

3. The method of claim 1, wherein probe hybridization occurs in the cell nucleus.

4. The method of claim 1, wherein the cell is a living cell.

5. The method of claim 4, wherein the at least one of the target sequences of transcribed RNA is endogenous RNA.

6. The method of claim 1, wherein the cell is a mammalian cell, an invertebrate cell, a yeast cell or a bacterium.

7. The method of claim 4, wherein the cell is a human cell.

8. The method of claim 4, wherein the cell is a cancer cell.

9. The method of claim 1, wherein at least one of the target transcribed RNAs encodes a protein.

10. The method of claim 1, wherein at least one of the target transcribed RNAs is non-coding RNA (ncRNA).

11. An assay for simultaneously determining the structural conformation of a chromosome in a cell and quantitatively measuring the level of gene expression at a chromosomal location, the assay comprising hybridizing a plurality of target sequences of more than one transcribed RNA in the cell with members of a plurality of fluorescently labeled oligonucleotide probe sets and counting fluorescent spots corresponding to single molecules of target transcribed RNAs to obtain a quantitative gene expression profile corresponding to the simultaneously determined, associated chromosomal conformation, wherein:

(i) each probe set utilizes a distinguishable color;

(ii) the plurality of targeted sequences of transcribed RNA are transcribed from portions of at least one chromosome;

(iii) the pattern of fluorescently labeled probes hybridized to the target sequences of transcribed RNA is indicative of the structural conformation of the chromosome;

(iv) each fluorescently labeled oligonucleotide probe set includes more than sixteen fluorescently labeled oligonucleotides;

(v) the locations of the hybridized probes are simultaneously indicative of the chromosomal locations of gene expression for the transcribed RNAs, and each of the fluorescently labeled oligonucleotides are coupled to an organic dye at their 3' end;

(vi) the number, the intensity, or both, of fluorescing probes is indicative of the level of gene expression at the chromosomal locations;

(vii) each fluorescently labeled probe targets an intron of the transcribed RNA sequence; thereby simultaneously determining the structural conformation of a chromosome in a cell and measuring the level of gene expression at a chromosomal location;

(viii) at least two introns are targeted in the cell and at least sixteen fluorescently labeled probes having different nucleotide sequences are complementary to each targeted intron; and (ix) a fluorescent spot is discarded as background based at least on color.

12. The assay of claim 11, wherein the probes are non-overlapping.

13. The assay of claim 10, wherein probe hybridization occurs in the cell nucleus.

14. The assay of claim 11, wherein the cell is a living cell.

15. The assay of claim 14, wherein the target sequences of at least one of the transcribed RNAs are transcribed from an endogenous gene.

16. The assay of claim 11, wherein the cell is a mammalian cell, an invertebrate cell, a yeast cell or a bacterium.

17. The assay of claim 11, wherein the cell is a human cell.

18. The assay of claim 11, wherein the cell is a cancer cell.

19. The assay of claim 11, wherein at least one of the target transcribed RNAs encodes a protein.

20. The method of claim 1, wherein a fluorescent spot is discarded as background if it is not multi-color.

21. The assay of claim 11, wherein a fluorescent spots is discarded as background if it is not multi-color.

22. The method of claim 1, wherein at least two target sequences are located in an RNA fusion transcript that is transcribed from a chromosomal region comprising a chromosomal translocation site; and wherein at least one probe targets one half of the fusion transcript and at least one probe targets the other half.

23. The assay of claim 11, wherein at least two target sequences are located in an RNA fusion transcript that is transcribed from a chromosomal region comprising a chromosomal translocation site; and wherein at least one probe targets one half of the fusion transcript and at least one probe targets the other half.

* * * * *